US009574191B2

(12) United States Patent
Corey et al.

(10) Patent No.: US 9,574,191 B2
(45) Date of Patent: Feb. 21, 2017

(54) SELECTIVE INHIBITION OF POLYGLUTAMINE PROTEIN EXPRESSION

(75) Inventors: David R. Corey, Dallas, TX (US); Jiaxin Hu, Dallas, TX (US); Dinah W. Y. Sah, Hopkinton, MA (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 284 days.

(21) Appl. No.: 13/575,842

(22) PCT Filed: Feb. 3, 2011

(86) PCT No.: PCT/US2011/023615
§ 371 (c)(1),
(2), (4) Date: Mar. 18, 2013

(87) PCT Pub. No.: WO2011/097388
PCT Pub. Date: Aug. 11, 2011

(65) Prior Publication Data
US 2013/0172399 A1 Jul. 4, 2013

Related U.S. Application Data

(60) Provisional application No. 61/417,048, filed on Nov. 24, 2010, provisional application No. 61/321,416, filed on Apr. 6, 2010, provisional application No. 61/301,067, filed on Feb. 3, 2010.

(51) Int. Cl.
*C12N 15/11* (2006.01)
*C12N 15/113* (2010.01)
*A61K 31/713* (2006.01)
*A61K 38/17* (2006.01)

(52) U.S. Cl.
CPC ........... *C12N 15/113* (2013.01); *A61K 31/713* (2013.01); *A61K 38/1709* (2013.01); *C12N 2310/14* (2013.01); *C12N 2310/315* (2013.01); *C12N 2310/321* (2013.01); *C12N 2310/332* (2013.01); *C12N 2310/346* (2013.01); *C12N 2310/533* (2013.01); *C12N 2320/34* (2013.01)

(58) Field of Classification Search
CPC .......................... C12N 15/113; C12N 2310/14
See application file for complete search history.

(56) References Cited

U.S. PATENT DOCUMENTS

| 8,901,095 B2 * | 12/2014 | Corey et al. ................. 514/44 A |
| 2008/0015158 A1 | 1/2008 | Ichiro ........................... 536/24.5 |
| 2009/0105169 A1 * | 4/2009 | Davidson et al. .............. 514/44 |
| 2009/0186410 A1 * | 7/2009 | Aronin et al. ................. 435/375 |

FOREIGN PATENT DOCUMENTS

| WO | WO 2004/058940 | 7/2004 |
| WO | WO 2007/051045 | 5/2007 |

OTHER PUBLICATIONS

Saxena et al. The Journal of Biological Chemistry 278, 44312-44319 2003.*
Aleman et al. RNA 13:385-395.*
Drouet et al. Ann. Neurol. 65: 276-285, 2009.*
Boudreau et al. Mol. Ther. 17:1053-1053, 2009.*
Wang et al. Nature 2008, 456: 921-926.*
Doench et al. (Genes & Development 17: 438-442, 2003.*
Hu et al. Chemistry & Biology 17: 1183-1188, Nov. 2010.*
Alves, et al., "Allele-Specific RNA Silencing of Mutant Ataxin-3 Mediates Neuroprotection in a Rat Model of Machado-Joseph Disease", PLoS One, 3(10):e3341, 2008.
Boado, et al., "Antisense-Mediated Down-Regulation of the Human Huntingtin Gene", J Pharmacol Exp Ther. 295:239-243, 2002.
Browne and Beal, "The Energetics of Huntington's Disease", Neurochem Res. 29(3):531-546, 2004.
Burnett, et al., "The polyglutamine neurodegenerative protein ataxin-3 binds polyubiquitylated proteins and has ubiquitin protease activity", Hum Mol Genet. 12(23):3195-3205, 2003.
Chai, et al., "Poly-ubiquitin Binding by the Polyglutamine Disease Protein Ataxin-3 Links Its Normal Function to Protein Surveillance Pathways", J Biol Chem. 279(5):3605-3611, 2004.
Denovan-Wright and Davidson, "RNAi: a potential therapy for the dominantly inherited nucleotide repeat diseases", Gene Therapy, 13:525-531, 2006.
DiFiglia et al., "Therapeutic silencing of mutant huntingtin with siRNA attenuates striatal and cortical neuropathology and bheavioral deficits", Proc. Natl. Acad. Sci. USA, 104:17204-17209, 2007.
Donaldson et al., "Ubiquitin Signals Protein Trafficking via Interaction with a Novel Ubiquitin Binding Domain in the Membrane Fusin Regulator, Vps9p", Curr. Biol., 13(3):258-262, 2003.
Dunah et al., "Sp1 and TAFII130 Transcriptional Activity Disrupted in Early Huntington's Disease", Science, 296(5576):2238-2243, 2002.
Filipowicz, et al., "Mechanisms of post-transcriptional regulation by microRNAs: are the answers in sight?", Nat Rev Genet. 9(2):102-14, 2008.
Gunawardena and Goldstein, "Polyglutamine Diseases and Transport Problems: Deadly Traffic James on Neuronal Highways", Arch. Neurol., 62(1):46-51, 2005.
Gusella and MacDonald, "Huntington's disease: seeing the pathogenic process through a genetic lens", Trends. Biochem. Sci., 31:533-540, 2006.
Harper et al., "RNA interference improves motor and neuropathological abnormalities in a Huntington's disease mouse model", Proc. Natl. Acad. USA, 102:5820-5825, 2005.

(Continued)

Primary Examiner — Brian Whiteman
(74) Attorney, Agent, or Firm — Norton Rose Fulbright US LLP

(57) ABSTRACT

The present invention relates to the selective inhibition of protein expression of CAG repeat-related disease proteins such as Huntingtin Disease Protein and Ataxin-3 using double-stranded RNAs and nucleic acid analogs. Chemically-modified RNAs having at least one mismatch as compared to the target CAG repeat sequence are specifically contemplated.

2 Claims, 37 Drawing Sheets

(56) References Cited

OTHER PUBLICATIONS

Hasholt et al., "Antisense downregulation of mutant huntingtin in a cell model", *J. Gene. Med.*, 5:528-538, 2003.
Hu et al., "Inhibiting Expression of Mutant Huntingtin and Ataxin-3 by Targeting Expanded CAG Repeat RNAs", *Nat. Biotech.*, 27:478, 2009.
Hu, et al., "Allele-Selective Inhibition of Mutant Huntingtin by Peptide Nucleic Acid-Peptide Conjugates, Locked Nucleic Acid, and Small Interfering RNA", *Ann NY Acad Sci.* 1175: 24-31, 2009.
Hu, et al., "Cellular localization and allele-selective inhibition of mutant Huntingtin protein by peptide nucleic acid oligomers containing the fluorescent nucleobase [bis-o-(aminoethoxy)phenyl]pyrrolocytosine", *Bioorg & Med Chem Lett.* 19: 6181-4, 2009.
Hughes, "Polyglutamine Disease: Acetyltransferases Awry", *Curr. Biol.*, 12(4): R141-143, 2002.
International Preliminary Report on Patentability in International application No. PCT/US2011/023615 mailed Aug. 16, 2012.
Irwin et al., "RNA association and nucleocytoplasmic shuttling by ataxin-1", *J. Cell Sci.*,118(Pt 1):233-242, 2005.
Kazantsev et al., "Insoluble detergent-resistant aggregates form between pathological and nonpathological lengths of polyglutamine in mammalian cells", *Proc. Natl. Acad. Sci. USA*, 96(20):11404-11409, 1999.
Klement et al., "Ataxin-1 Nuclear Localization and Aggression: Role in Polyglutamine-Induced Disease in SCA1 Transgenic Mice", *Cell*, 95(1):41-53, 1998.
Kurreck, "RNA Interference: From Basic Research to Therapeutic Applications", *Angew Chem Int Ed Engl.* 48(8):1378-98, 2009.
Li et al., "Huntingtin-associated Protein 1 Interacts with Hepatocyte Growth Factor-regulated Tyrosine Kinase Substrate and Functions in Endosomal Trafficking", *J Biol Chem.*, 277(31):28212-28221, 2002.
Liu et al., "Argonaute2 Is the Catalytic Engine of Mammalian RNAi", *Science.* 305(5689):1437-41, 2004.
Mao et al., "Deubiquitinating function of ataxin-3: Insights from the solution structure of the Josephin domain", *Proc. Natl. Acad. Sci. USA*, 102(36):12700-12705, 2005.
Miller, et al., "Allele-specific silencing of dominant disease genes", *PNAS.* 100(12):7195-7200, 2003.
Nasir et al., "Targeted Disruption of the Huntington's Disease Gene Results in Embryonic Lethality and Behavioral and Morphological Changes in Heterozygotes", *Cell*, 81:811-823, 1995.

Nicastro et aL., "The solution structure of the Josephin domain of ataxin-3: Structureal deterinants for molecular recognition", *Proc. Natl. Acad. Sci. USA*, 102(30):10493-10498, 2005.
Nucifora et al., "Interference by Huntingtin and Atrophin-1 with CBP-Mediated Transcription Leading to Cellular Toxicity", *Science*, 2923(5512):2423-2428, 2001.
Ohnishi et al., "Enhancement of Allele Discrimination by Introduction of Nucleotide Mismatches into siRNA in Allele-Specific Gene Silencing by RNAi", *PLoS ONE.* 3(5):e2248, 2008.
Rodriguez-Lebrón and Paulson, "Allele-specific RNA interference for neurological disease", *Gene Therapy*, 13:576-581, 2006.
Scheel et al., "Elucidation of ataxin-3 and ataxin-7 function by integrative bioinformatics", *Hum. Mol. Genet.*, 12(21):2845-2852, 2003.
Scholefield & Wood, "Therapeutic gene silencing strategies for polyglutamine disorders", *Trends Genetics*, 26(1):29-38, 2009.
Schwarz et al., "Designing siRNA That Distinguish between Genes That Differ by a Single Nucleotide", *PLOS Genetics*, 2:1307-1318, 2006.
Servadio et al., "Expression analysis of the ataxin-1 protein in tissues from normal and spinocerebellar ataxia type 1 individuals", *Nat. Genet.*, 10(1):94-98, 1995.
Steffan et al., "Histone deacetylase inhibitors arrest polyglutamine-dependent neurodegeneration in *Drosophila*", *Nature*, 413(6857):739-743, 2001.
van Bilsen et al., "Identification and Allele-Specific Silencing of the Mutant Huntingtin Allele in Huntington's Disease Pateint-Derived Fibroblasts", *Hum. Gene Ther.*, 19(7):710-9, 2008.
Wang, et al., "Mechanism of induction and suppression of antiviral immunity directed by small RNAs in *Drosophila*", *Cell Host Microbe.* 4(4):387-97, 2008.
Warrick et al., "Ataxin-3 Suppresses Polyglutamine Neurodegeneration in *Drosophila* by a Ubiquitin-Associated Mechanism", *Mol. Cell*, 18(1):37-48, 2005.
White et al., "Huntingtin is required for neurogenesis and is not impaired by the Huntington's disease CAG expansion", *Nat. Genetics*, 17:404-410, 1997.
Yue et al., "The spinocerebellar ataxia type 1 protein, ataxin-1, has RNA-binding activity that is inversely affected by the length of its polyglutamine tract", *Hum. Mol. Genet.*, 10(1):25-30, 2001.
Zhai et al., "In vitro Analysis of Huntingtin-Mediated Transcriptional Repression Reveals Multiple Transcription Factor Targets", *Cell*, 123(7):1241-53, 2005.
Zhang, et al., "Allele-specific silencing of mutant Huntington's disease gene", *J Neurochem.* (108):82-90, 2009.

* cited by examiner

| Name | Sequence (5'-3') |
|---|---|

*Parent fully complementary RNA*
REP      GCUGCUGCUGCUGCUGCUGTT

*Single-mismatch, different locations*
P4       GCU<u>A</u>CUGCUGCUGCUGCUGTT
P6       GCUGC<u>A</u>GCUGCUGCUGCUGTT
P7       GCUGCU<u>A</u>CUGCUGCUGCUGTT
P8       GCUGCUG<u>A</u>UGCUGCUGCUGTT
P9       GCUGCUGC<u>A</u>GCUGCUGCUGTT
P10      GCUGCUGCU<u>A</u>CUGCUGCUGTT
P10R     GCUGCUGCU<u>U</u>CUGCUGCUGTT
P11      GCUGCUGCUG<u>A</u>UGCUGCUGTT
P12      GCUGCUGCUGC<u>A</u>GCUGCUGTT
P13      GCUGCUGCUGCU<u>A</u>CUGCUGTT
P16      GCUGCUGCUGCUGCU<u>A</u>CUGTT

*Two or more mismatches*
P910     GCUGCUGC<u>AA</u>CUGCUGCUGTT
RM3      GCU<u>A</u>CUGCU<u>A</u>CUGCU<u>A</u>CUGTT
RM4      GC<u>A</u>GCUG<u>U</u>UGCU<u>A</u>CUG<u>U</u>UGTT

FIG. 1

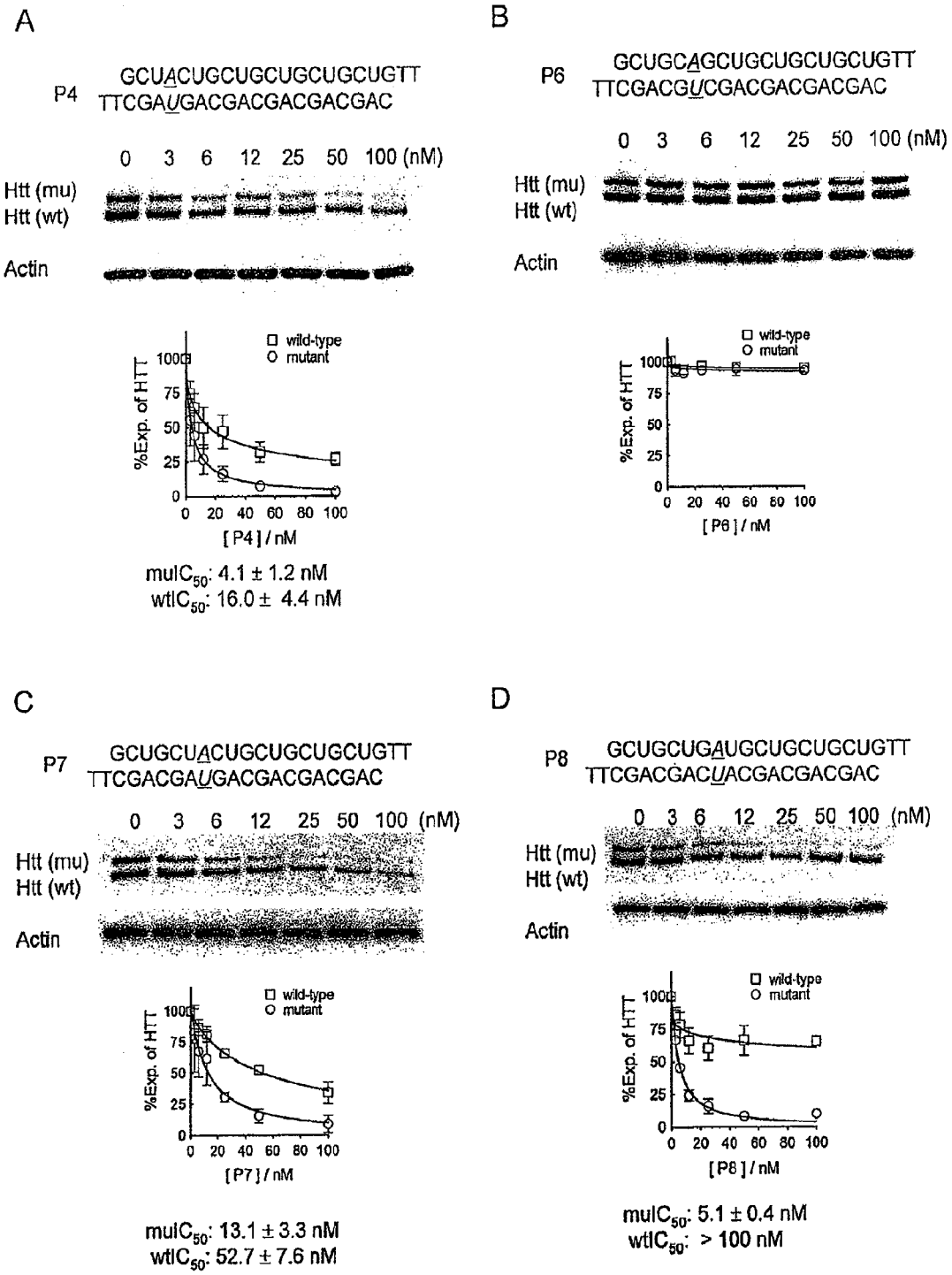
FIG. 2 A-D

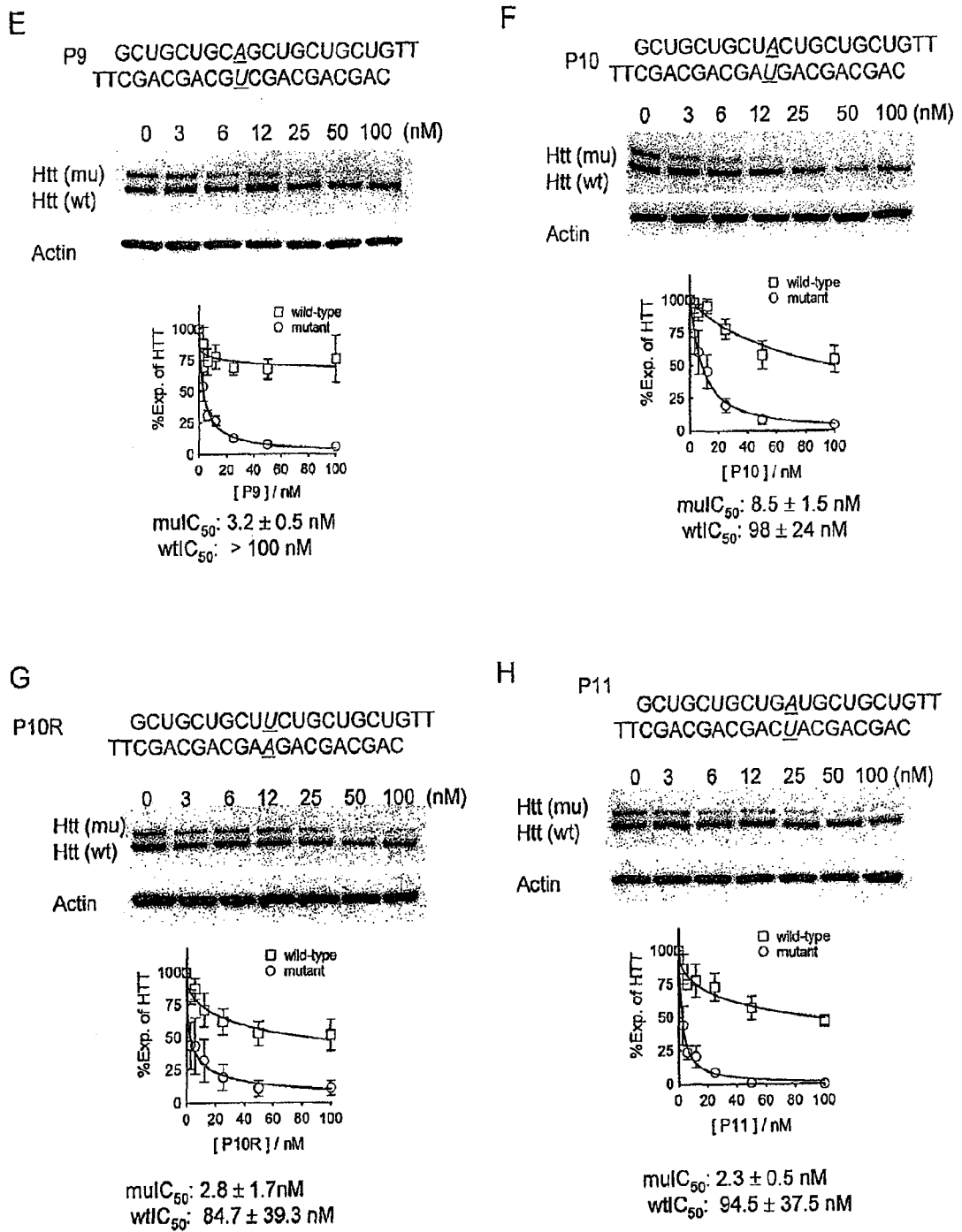
FIG. 2 E-H

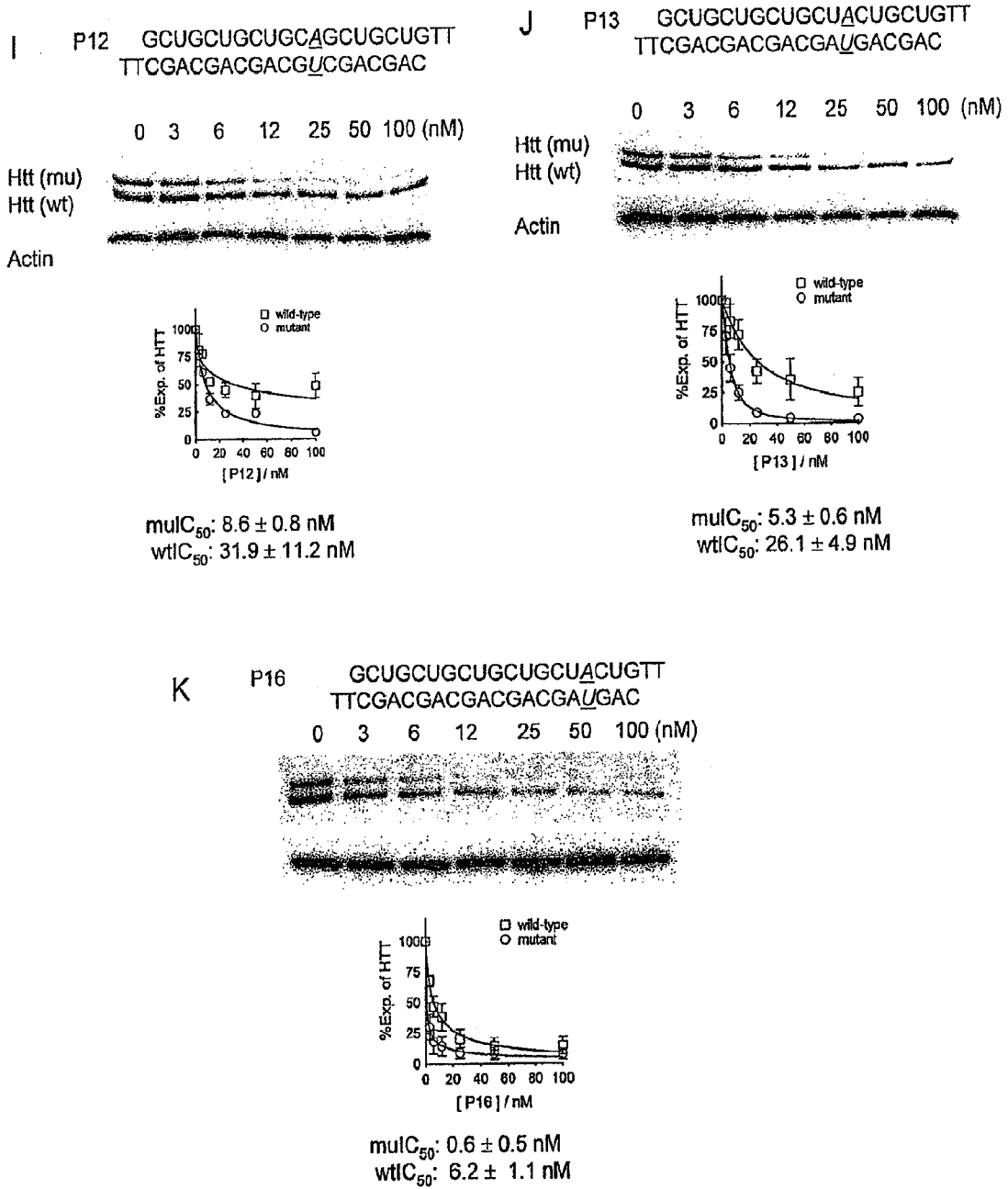
FIG. 2 I-K

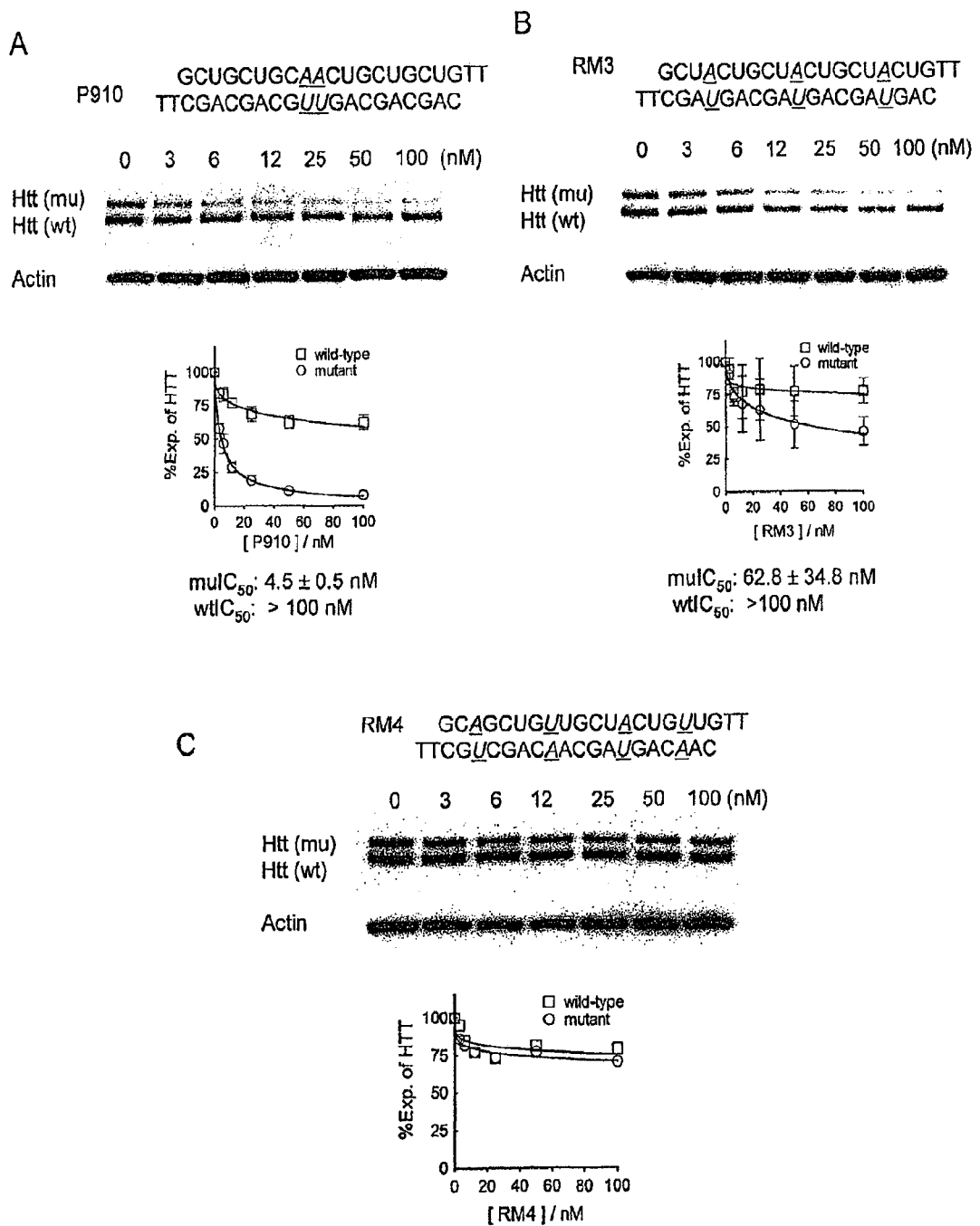
FIG. 3A-C

| siRNA | Sequence | Tm, °C | mut IC$_{50}$ (nM) | wt IC$_{50}$ (nM) |
|---|---|---|---|---|
| REP | GCUGCUGCUGCUGCUGCUGTT<br>TTCGACGACGACGACGACGAC | 86.8 | 5 ± 1.7 | 13 ± 2.2 |
| P4 | GCU*A*CUGCUGCUGCUGCUGTT<br>TTCGA*U*GACGACGACGACGAC | 84.0 | 4.1 ± 1.2 | 16.0 ± 4.4 |
| P6 | GCUGC*A*GCUGCUGCUGCUGTT<br>TTCGACG*U*CGACGACGACGAC | 85.1 | No inhibition | No inhibition |
| P7 | GCUGCU*A*CUGCUGCUGCUGTT<br>TTCGACGA*U*GACGACGACGAC | 82.7 | 13.1 ± 3.3 | 52.7 ± 7.6 |
| P8 | GCUGCUG*A*UGCUGCUGCUGTT<br>TTCGACGAC*U*ACGACGACGAC | 83.8 | 5.1 ± 0.4 | >100 |
| P9 | GCUGCUGC*A*GCUGCUGCUGTT<br>TTCGACGACG*U*CGACGACGAC | 86.7 | 3.2 ± 0.5 | >100 |
| P10 | GCUGCUGCU*A*CUGCUGCUGTT<br>TTCGACGACGA*U*GACGACGAC | 83.5 | 8.5 ± 1.5 | 98 ± 24 |
| P10R | GCUGCUGCU*U*CUGCUGCUGTT<br>TTCGACGACGA*A*GACGACGAC | 78.0 | 2.8 ± 1.7 | 84.7 ± 39.3 |
| P11 | GCUGCUGCUG*A*UGCUGCUGTT<br>TTCGACGACGAC*U*ACGACGAC | 83.7 | 2.3 ± 0.5 | 94.5 ± 37.5 |
| P12 | GCUGCUGCUGC*A*GCUGCUGTT<br>TTCGACGACGACG*U*CGACGAC | 85.6 | 8.6 ± 0.8 | 31.9 ± 11.2 |
| P13 | GCUGCUGCUGCU*A*CUGCUGTT<br>TTCGACGACGACGA*U*GACGAC | 82.8 | 5.3 ± 0.6 | 26.1 ± 4.9 |
| P16 | GCUGCUGCUGCUGCU*A*CUGTT<br>TTCGACGACGACGACGA*U*GAC | 76.4 | 0.6 ± 0.5 | 6.2 ± 1.1 |
| P910 | GCUGCUGC*AA*CUGCUGCUGTT<br>TTCGACGACG*UU*GACGACGAC | 83.5 | 4.5 ± 0.5 | >100 |
| RM3 | GCU*A*CUGCU*A*CUGCU*A*CUGTT<br>TTCGA*U*GACGA*U*GACGA*U*GAC | 83.0 | 62.8 ± 34.8 | >100 |
| RM4 | GC*A*GCUG*U*UGCU*A*CUGU*U*UGTT<br>TTCG*U*CGAC*A*ACGA*U*GAC*A*AC | 78.0 | No inhibition | No inhibition |

FIG. 4

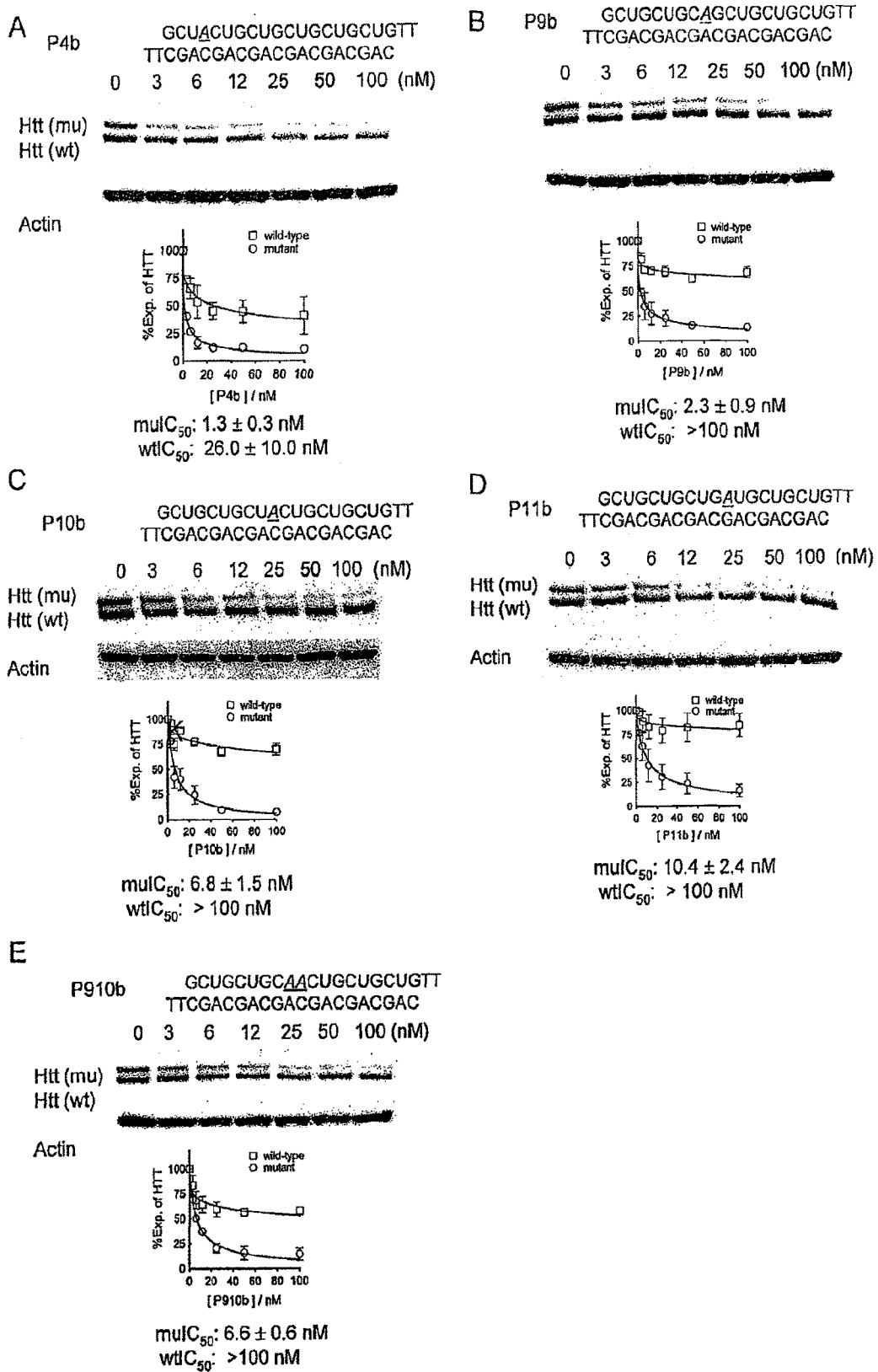
FIG. 5A-E

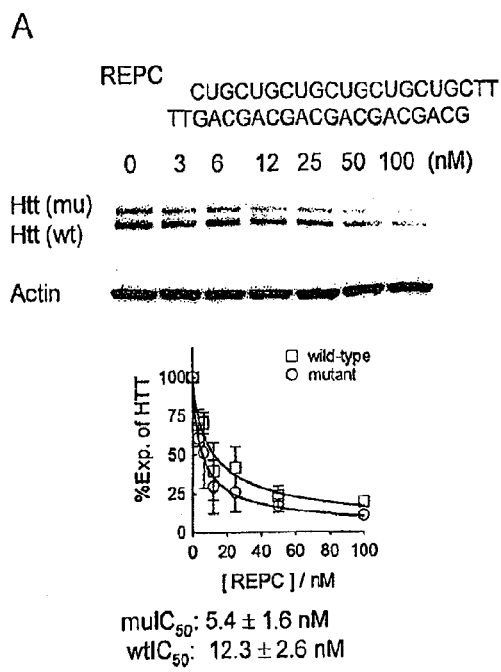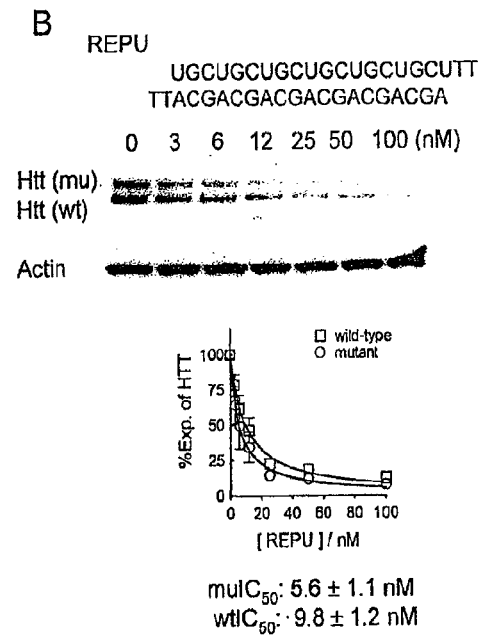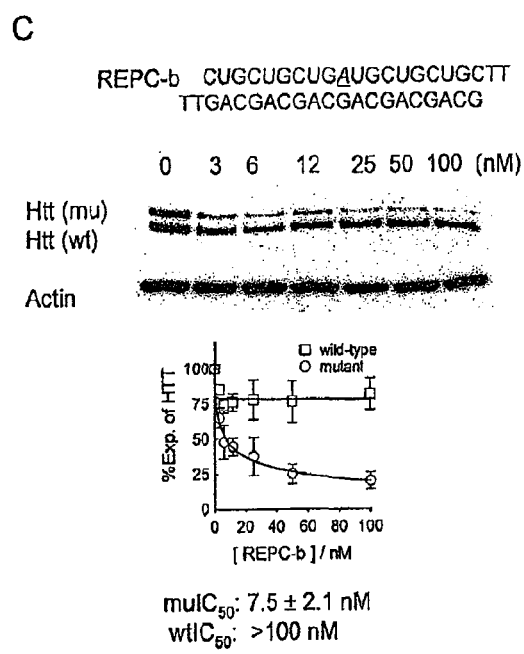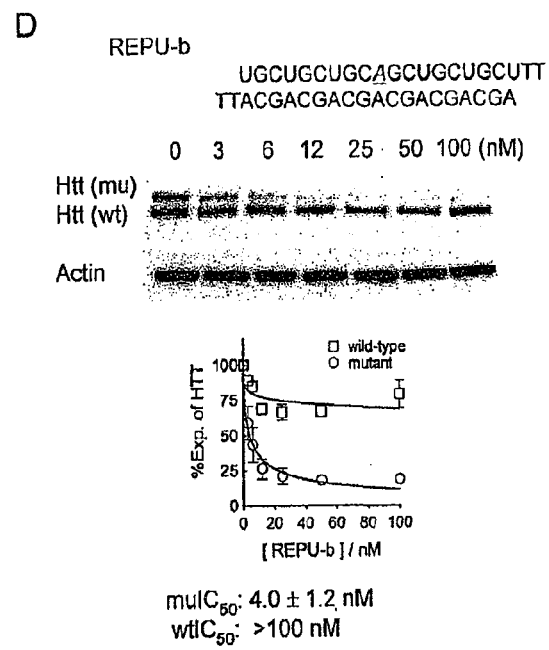
FIG. 6 A-D

A
P9  GCUGCUGC*A*GCUGCUGCUGTT
    TTCGACGACG*U*CGACGACGAC
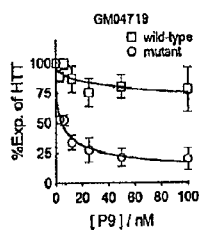
muIC$_{50}$: 4.5 ± 1.3 nM
wtIC$_{50}$: > 100 nM
B
P910  GCUGCUGC*AA*CUGCUGCUGTT
      TTCGACGACG*UU*GACGACGAC
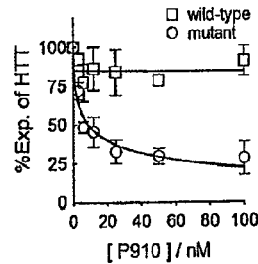
muIC$_{50}$: 8.9 ± 2.2 nM
wtIC$_{50}$: > 100 nM
FIG. 7A-B

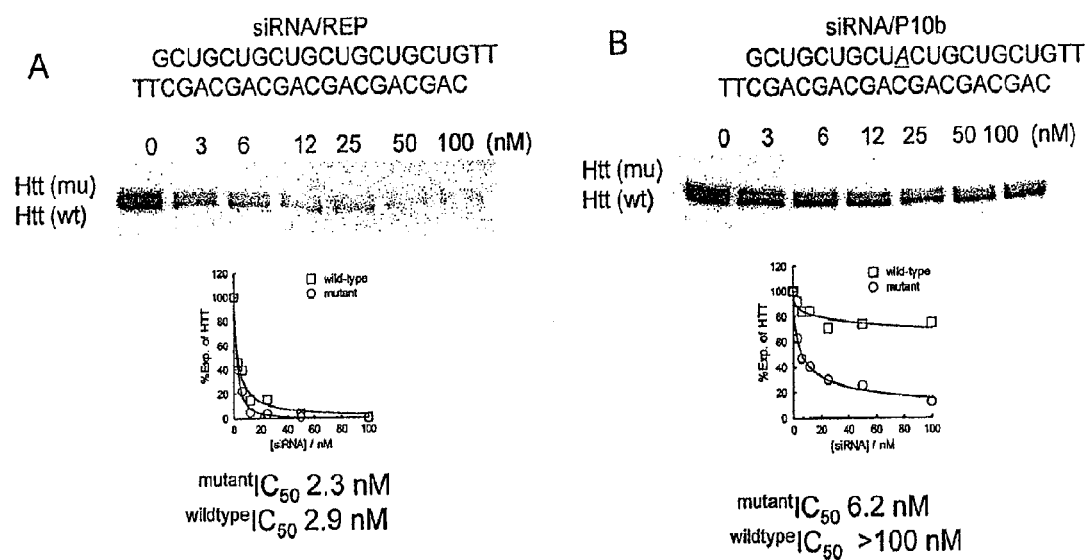
FIG. 8A-B

| siRNA ALNY name | Name on modification | Sequence | Tm, °C |
|---|---|---|---|
| AD26319-b1 | MP9 | GCUGCUGc*A*GCUGCUGCUGTsT TsTcGAcGAcG*uc*GAcGAcGAc | 89.2 |
| AD26320-b1 | MP910 | GCUGCUGc*AA*CUGCUGCUGTsT TsTcGAcGAcG*uu*GAcGAcGAc | 85.5 |
| AD26321-b1 | MP9b | GCUGCUGc*A*GCUGCUGCUGTsT TsTcGAcGAcGAcGAcGAcGAc | 81.1 |
| AD26322-b1 | MP10b | GCUGCUGCu*A*CUGCUGCUGTsT TsTcGAcGAcGAcGAcGAcGAc | 79.8 |
| AD26323-b1 | MP11b | GCUGCUGCUG*A*UGCUGCUGTsT TsTcGAcGAcGAcGAcGAcGAc | 78.4 |
| AD26324-b1 | MRC/b | CUGCUGCUG*A*UGCUGCUGCTsT TsTGAcGAcGAcGAcGAcGAcG | 78.2 |
| AD26325-b1 | MRU/b | UGCUGCUGc*A*GCUGCUGCUTsT TsTAcGAcGAcGAcGAcGAcGA | 80.2 |

FIG. 9

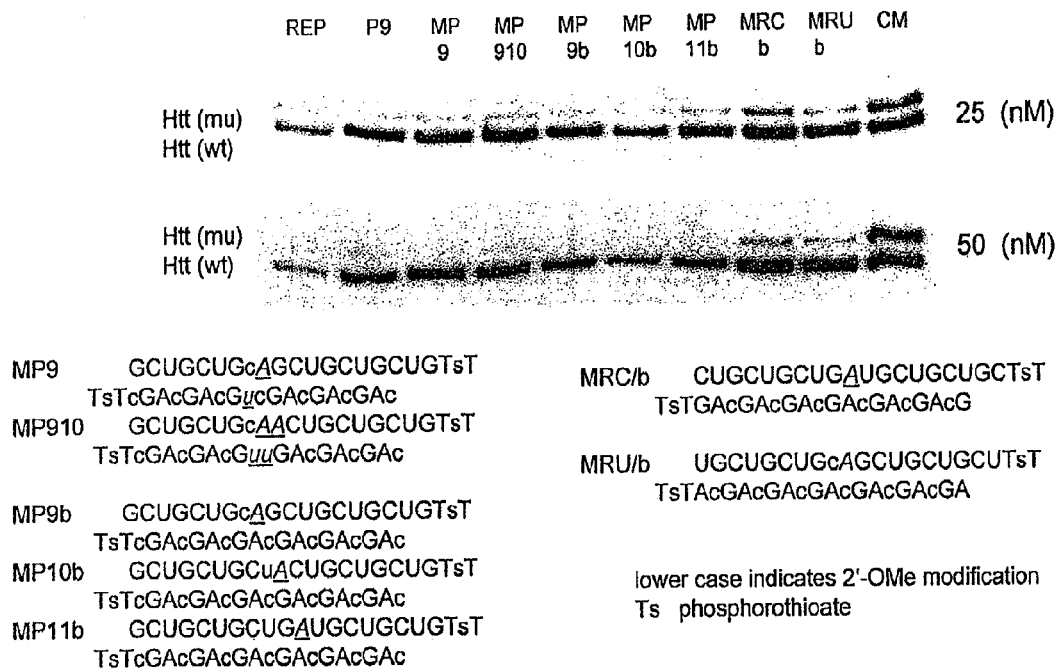

| | |
|---|---|
| MP9 | GCUGCUGc*A*GCUGCUGCUGTsT<br>TsTcGAcGAcG*u*cGAcGAcGAc |
| MP910 | GCUGCUGc*AA*CUGCUGCUGTsT<br>TsTcGAcGAcG*uu*GAcGAcGAc |
| MP9b | GCUGCUGc*A*GCUGCUGCUGTsT<br>TsTcGAcGAcGAcGAcGAcGAc |
| MP10b | GCUGCUGCu*A*CUGCUGCUGTsT<br>TsTcGAcGAcGAcGAcGAcGAc |
| MP11b | GCUGCUGCUG*A*UGCUGCUGTsT<br>TsTcGAcGAcGAcGAcGAcGAc |
| MRC/b | CUGCUGCUG*A*UGCUGCUGCTsT<br>TsTGAcGAcGAcGAcGAcGAcG |
| MRU/b | UGCUGCUGc*A*GCUGCUGCUTsT<br>TsTAcGAcGAcGAcGAcGAcGA | lower case indicates 2'-OMe modification
Ts phosphorothioate

FIG. 10

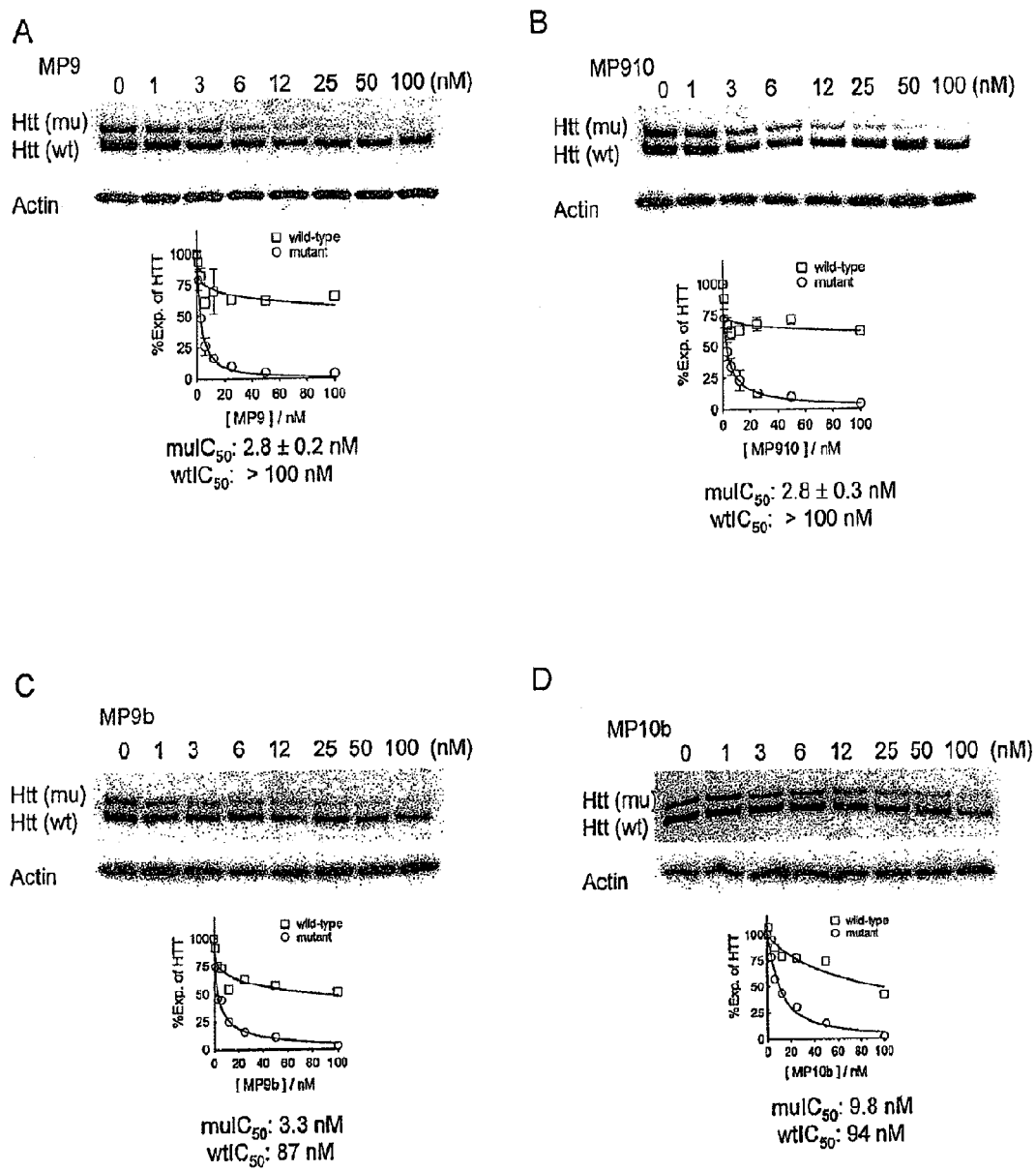
FIG. 11 A-D

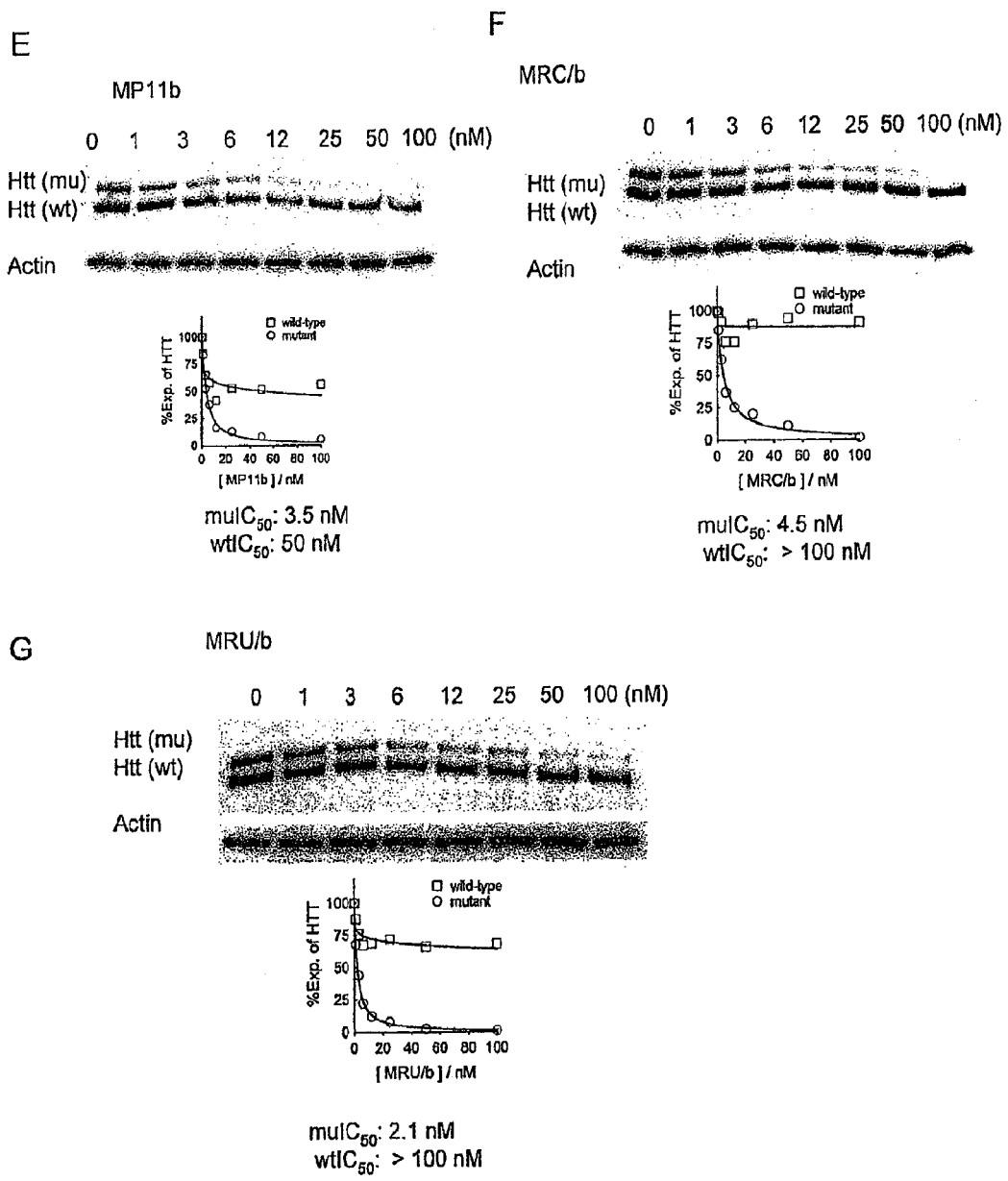
FIG. 11 E-G

A)
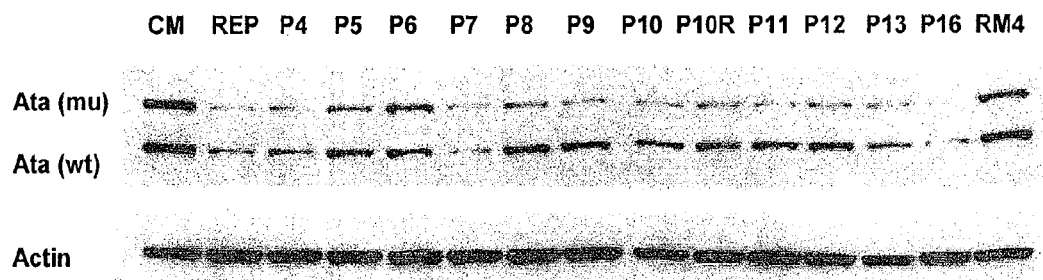
B)
C)
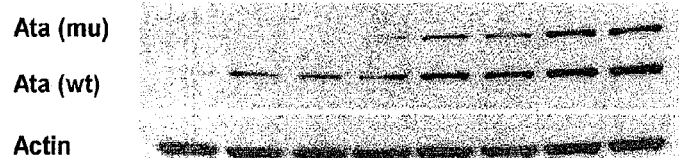
D)
FIG. 19A-D

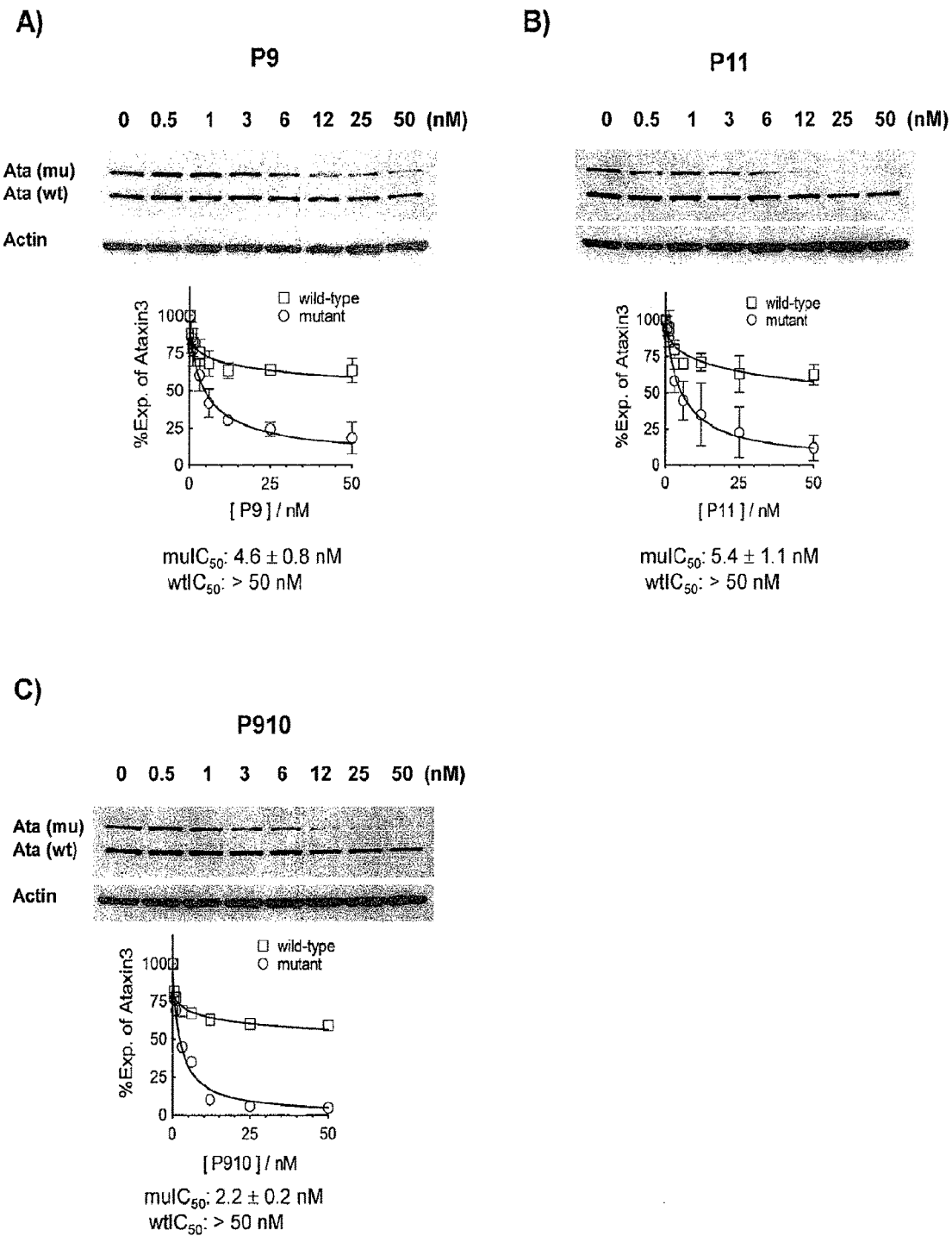
FIG. 20A-C

A)
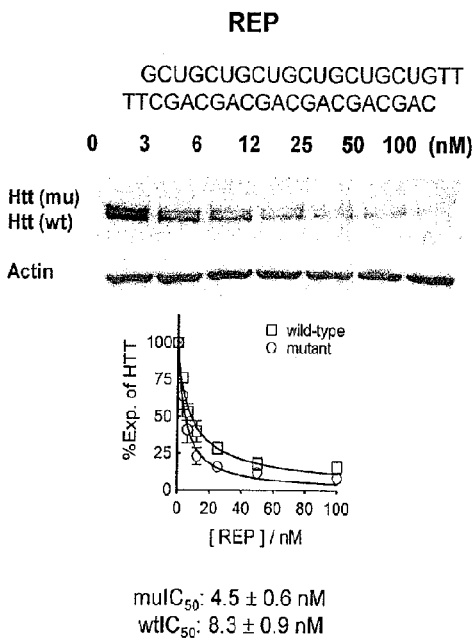
B)
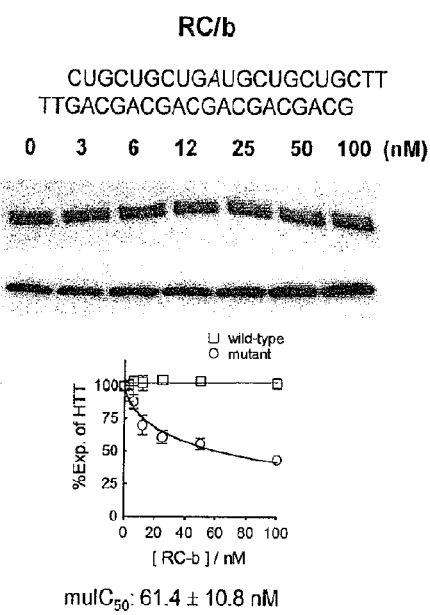
C)
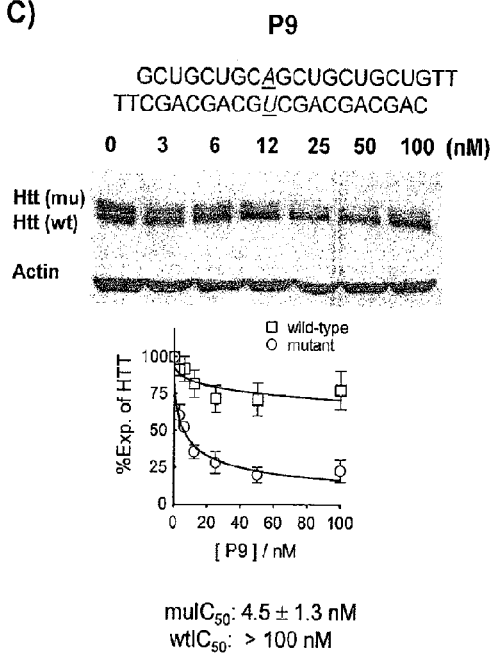
D)
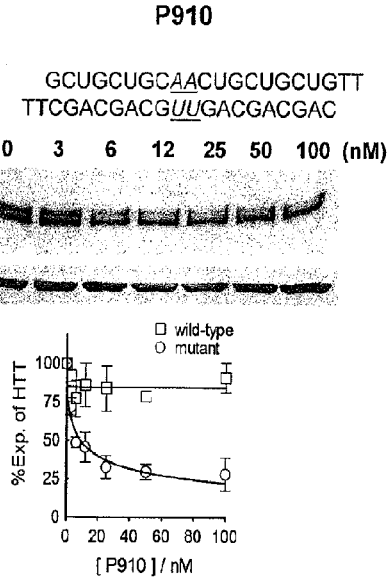
FIG. 21A-D

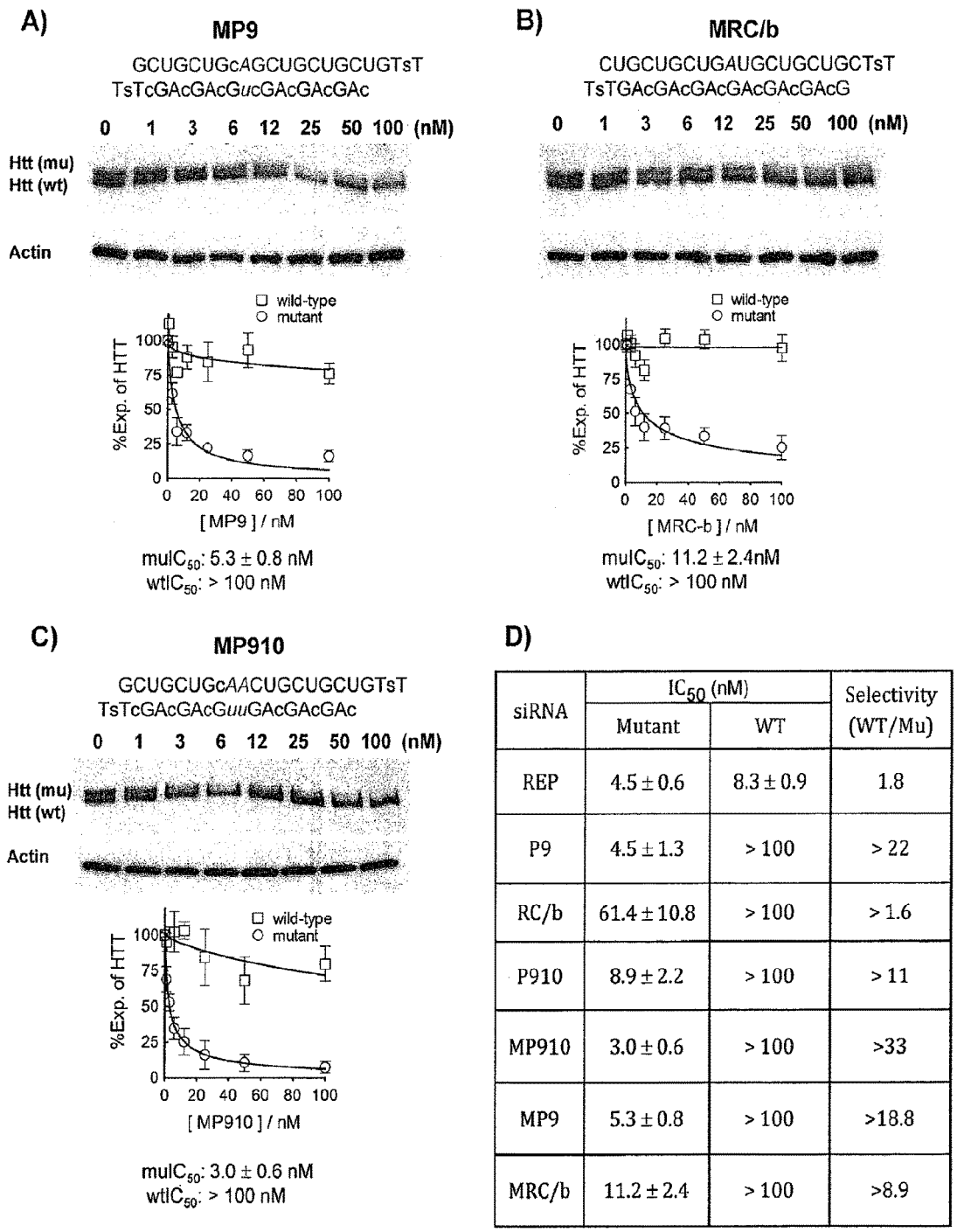
FIG. 22A-D

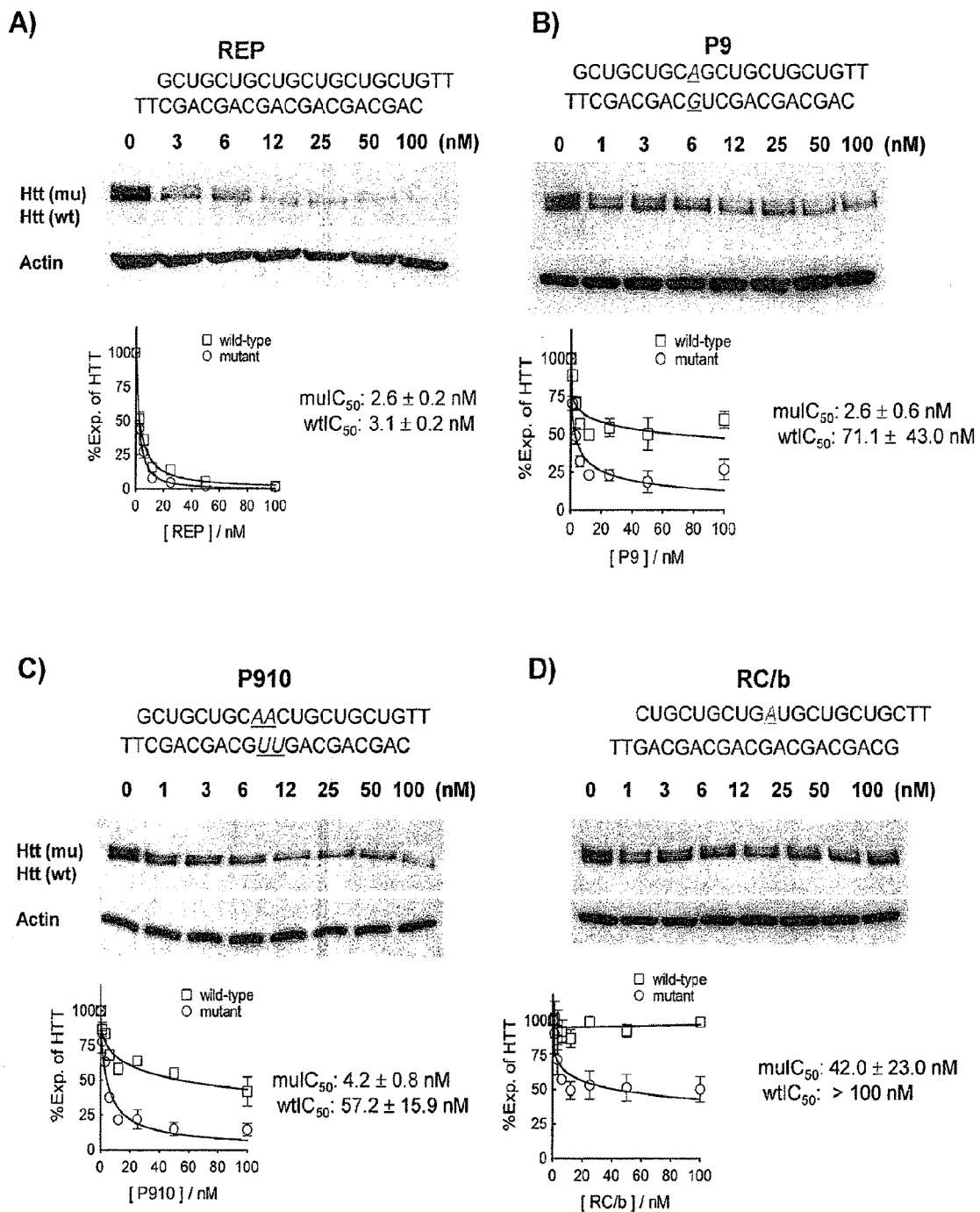
FIG. 23A-D

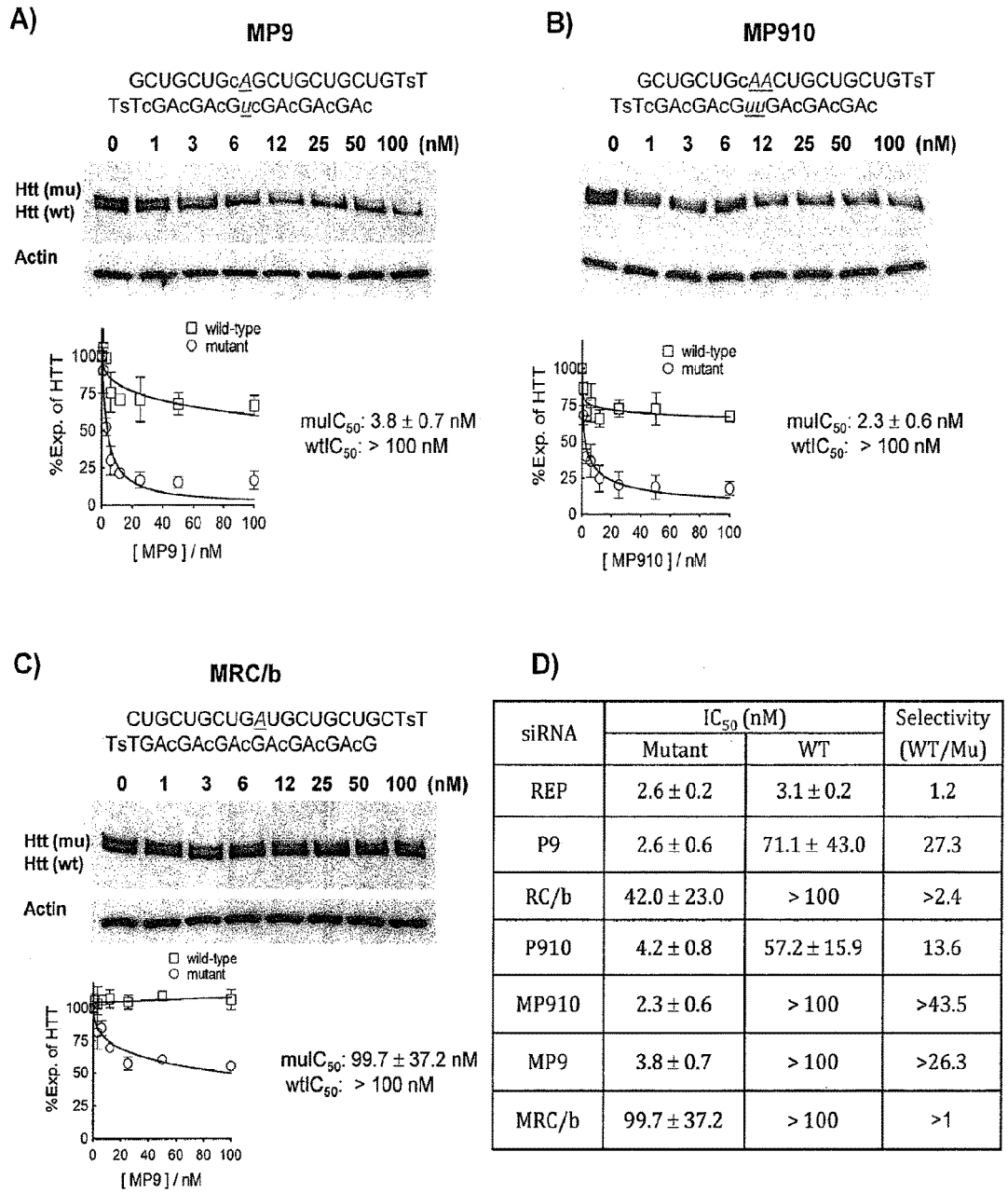
FIG. 24A-D a)
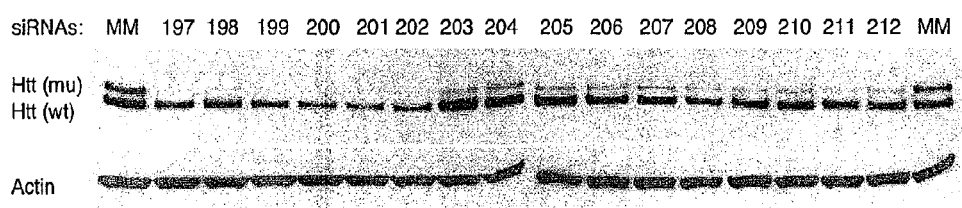
b)
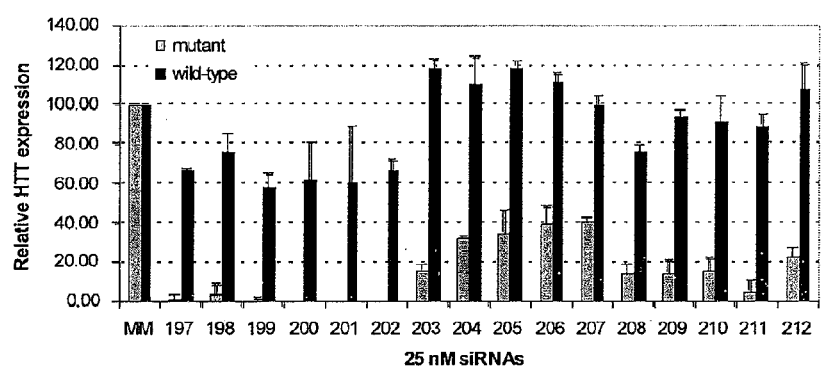
FIG. 26 a)
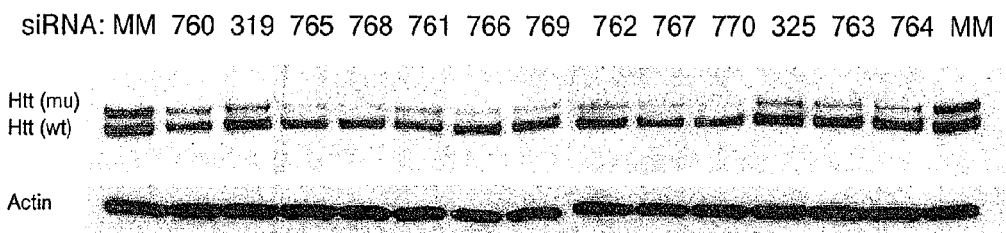
b)
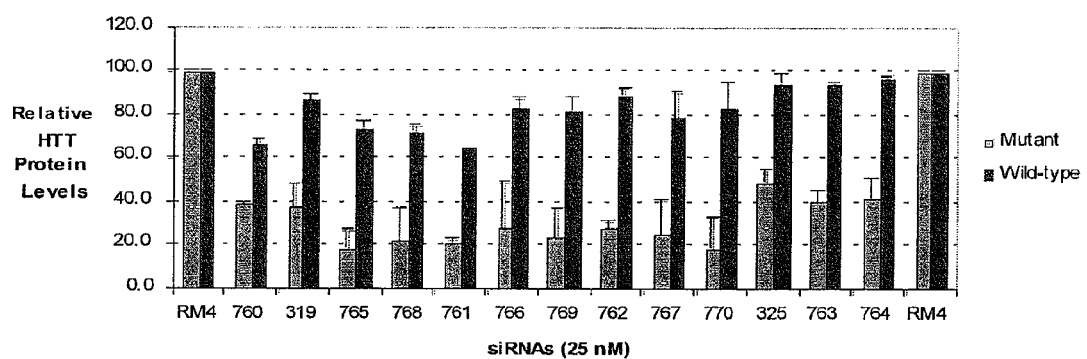
FIG. 28 a)
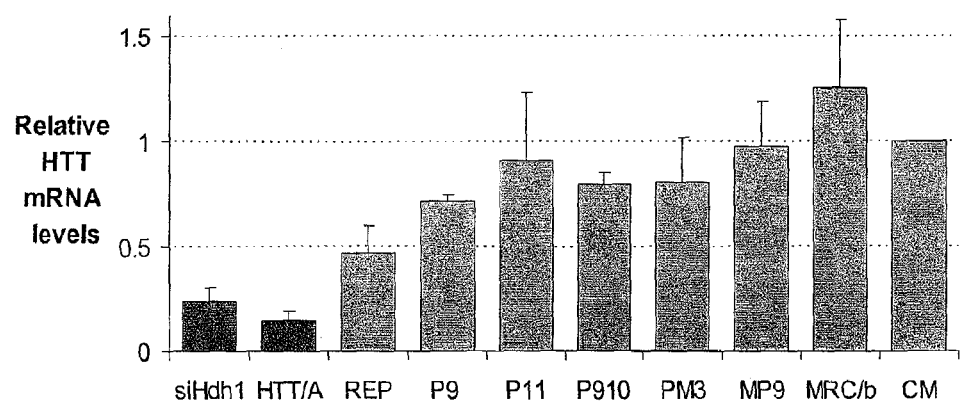
b)
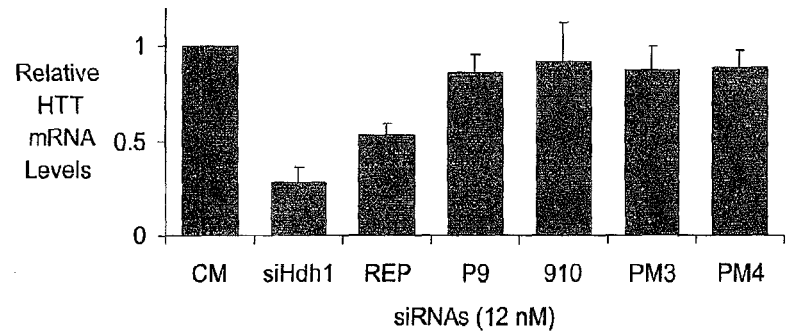
FIG. 30

SELECTIVE INHIBITION OF POLYGLUTAMINE PROTEIN EXPRESSION

This application is a national phase application under 35 U.S.C. §371 of International Application No. PCT/US2011/023615 filed Feb. 3, 2011, which claims benefit of priority to U.S. Provisional Application Ser. No. 61/417,048, filed Nov. 24, 2010, U.S. Provisional Application Ser. No. 61/321,416, filed Apr. 6, 2010, and U.S. Provisional Application Ser. No. 61/301,067, filed Feb. 3, 2010 the entire contents of each of these applications are hereby incorporated by reference.

STATEMENT REGARDING FEDERALLY SPONSORED RESEARCH OR DEVELOPMENT

This invention was made in part with government support under Grant No. GM073042 awarded by the National Institutes of Health. The United States Government has certain rights in the invention.

BACKGROUND OF THE INVENTION

A. Field of the Invention

The invention relates to the fields of biology and medicine. More particularly, the invention provides compositions and methods for the selective inhibition of expanded CAG-repeat containing disease proteins such as Huntingtin Disease (HTT) protein and Ataxin-3.

B. Related Art

Huntington's Disease (HD) is an autosomal dominant inherited disorder with an incidence of 5-10 per 100,000 individuals in Europe and North America (Borrell-Pages et al., 2004; Walker, 2007). HD is caused by the expansion of CAG trinucleotide repeats within the first exon of the huntingtin (HTT) gene, leading to disruption of protein function, and neurodegeneration (Gusella and MacDonald, 2006). Antisense oligonucleotides or siRNAs that reduce HTT expression have been proposed as a therapeutic strategy (Hasholt et al., 2003; Boado et al., 2002; Harper et al., 2005; Denovan-Wright and Davidson, 2006; DiFiglia et al., 2007) but most oligomers inhibit the mutant and wild-type protein expression indiscriminately. HTT is known to play an essential role in embryogenesis (Nasir et al., 1995), neurogenesis (White et al., 1997), and normal adult function in heterozygotes (Nasir et al., 1995), suggesting that agents inhibiting both mutant and wild-type HTT will induce significant side-effects. See Scholefield & Wood (2009) for a review.

One strategy for distinguishing mutant from wild-type alleles for HD and other neurological diseases uses siRNAs that target single nucleotide differences or deletions (Schwarz et al., 2006; Rodriguez-Lebron and Paulson, 2006; van Bilsen et al., 2008; Alves et al., 2008; Rodriguez-Lebron et al., 2009). These polymorphisms will often differ from patient to patient, complicating application of allele-specific RNAi in the clinic. Thus, there remains a need to identify agents that selectively inhibit mutant HTT production.

The inventors have previously demonstrated that single-stranded LNA or PNA oligomers that are fully-complementary to CAG repeat can inhibit expression of HTT or ataxin-3 in an allele-selective manner (Hu et al., 2009a; 2009b; 2009c). They also examined inhibition by fully-complementary duplex RNA, but observed little selectivity for inhibition of mutant versus wild-type HTT (Hu et al., 2009a).

SUMMARY OF THE INVENTION

Thus, in accordance with the present invention, there is provided a method for inhibiting expression of a disease protein encoded by an mRNA having expanded CAG repeat region comprising contacting a cell that produces said disease protein with a double-stranded RNA of 15-30 bases that targets said expanded CAG repeat region of a disease protein mRNA, and said double-stranded RNA further contains 1, 2, 3, 4 or 5 base mismatches as compared to the CAG repeat, wherein (i) inhibiting is selective for said disease protein expression over expression of a normal form of said disease protein, an mRNA for said normal form which lacks said expanded CAG repeat region, (ii) and said double-stranded RNA contains no more than one base mismatch in a seed sequence. Inhibiting may, in some cases, not substantially affect production of said disease protein mRNA. Selectivity may be on the order of 5-fold to 40-fold, 10-fold to 40-fold, 20-fold to 40-fold, or 30-fold to 40-fold.

The CAG repeat region may be about 125 repeats or less in size. The double-stranded RNA may be 19 to about 21 bases in length. The disease protein may be Huntingtin, ataxin-3, ataxin-1, ataxin-2 or atrophin1. The double-stranded RNA may comprise one or more chemically-modified bases, such as a 2'-O-methyl modified nucleotide, a nucleotide comprising a 5'-phosphorothioate group, and a terminal nucleotide linked to a cholesteryl derivative or dodecanoic acid bisdecylamide group, a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, or a non-natural base comprising nucleotide. The guide strand or the passenger strand may contain the chemically-modified base, or both the guide and passenger strands may contain at least one chemically-modified base. The double-stranded RNA may comprise a non-natural internucleotide linkage, such as a phosphorothioate linkage. The double-stranded RNA may further comprise an inserted base as compared to said CAG repeat. The inserted based may be in the guide strand.

The double-stranded RNA may further target a repeat region junction. The double-stranded RNA may comprise at least 15 bases and said first base mismatch maybe flanked by at least 7 bases on both the 5' and 3' ends of said double-stranded RNA. The first base mismatch may be in the guide strand. The double-stranded RNA may be further comprise a second base mismatch, such as in the passenger strand, or both base mismatches in the guide strand. The double-stranded RNA may comprise at least 16 bases and said first and second base mismatches may be adjacent and flanked by at least 7 bases on both the 5' and 3' ends of said double-stranded RNA. The double-stranded RNA may be at least 19 bases in length and said second base mismatch, or both said first and second base mismatches, may be located within base 9 to the 3' terminus. The double-stranded RNA may be at least 19 bases in length and may further comprises second and third base mismatches in the guide strand within base 9 to the 3' terminus, including where all of said, first, second and third base mismatches are located within base 9 to the 3' terminus. The double-stranded RNA may be at least 19 bases in length and further comprises second, third and fourth base mismatches in the guide strand within base 9 to the 3' terminus, such as where all of said first, second, third and fourth base mismatches are located within base 9 to the 3' terminus. The double-stranded RNA may be at least 19 bases in length and further comprises second, third, fourth and fifth base mismatches in the guide strand within base 9 to the 3' terminus, including where all of said first, second, third, fourth and fifth base mismatches are located within base 9 to the 3' terminus.

In another embodiment, there is provided a method for inhibiting expression, in a subject, of a disease protein encoded by an mRNA having expanded CAG repeat region comprising administering to said subject an amount of a double-stranded RNA of 15-30 bases that targets said expanded CAG repeat region of a disease protein mRNA, and said double-stranded RNA further contains 1, 2, 3, 4 or 5 base mismatches as compared to the CAG repeat, wherein (i) inhibiting is selective for said disease protein expression over expression of a normal form of said disease protein, an mRNA for said normal form which lacks said expanded CAG repeat region, (ii) and said double-stranded RNA contains no more than one base mismatch in a seed sequence. Inhibiting may, some cases, not substantially affect production of said disease protein mRNA. Selectivity may be on the order of 5-fold to 40-fold, 10-fold to 40-fold, 20-fold to 40-fold, or 30-fold to 40-fold. The double-stranded RNA may be administered more than once. The double-stranded RNA may be administered as a pharmaceutical composition by any means known in the art including, but not limited to oral or parenteral routes, including intracranial (including intraparenchymal and intraventricular), intrathecal, epidural, intravenous, intraarterial, intramuscular, intraperitoneal, subcutaneous, transdermal, airway (aerosol), nasal, rectal, vaginal and topical (including buccal and sublingual) administration. The double-stranded RNA may be administered in a lipid formulation or in a saline solution. The method may further comprise administering a second therapy to said subject.

The CAG repeat region may be about 125 repeats or less in size. The double-stranded RNA may be 19 to about 21 bases in length. The disease protein may be Huntingtin, ataxin-3, ataxin-1, ataxin-2 or atrophin1. The double-stranded RNA may comprise one or more chemically-modified bases, such as a 2'-O-methyl modified nucleotide, a nucleotide comprising a 5'-phosphorothioate group, a terminal nucleotide linked to a cholesteryl derivative or dodecanoic acid bisdecylamide group, a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, or a non-natural base comprising nucleotide. The guide strand or the passenger strand may contain the chemically-modified base, or both the guide and passenger strands may contain at least one chemically-modified base. The double-stranded RNA may comprise a non-natural internucleotide linkage, such as a phosphorothioate linkage. The double-stranded RNA may further comprise an inserted base as compared to said CAG repeat. The inserted based may be in the guide strand.

The double-stranded RNA may further target a repeat region junction. The double-stranded RNA may comprise at least 15 bases and said first base mismatch maybe flanked by at least 7 bases on both the 5' and 3' ends of said double-stranded RNA. The first base mismatch may be in the guide strand. The double-stranded RNA may be further comprise a second base mismatch, such as in the passenger strand, or both in the guide strand. The double-stranded RNA may comprise at least 16 bases and said first and second base mismatches may be adjacent and flanked by at least 7 bases on both the 5' and 3' ends of said double-stranded RNA. The double-stranded RNA may be at least 19 bases in length and said second base mismatch, or both said first and second base mismatches, may be located within base 9 to the 3' terminus. The double-stranded RNA may be at least 19 bases in length and may further comprises second and third base mismatches in the guide strand within base 9 to the 3' terminus, including where all of said, first, second and third base mismatches are located within base 9 to the 3' terminus. The double-stranded RNA may be at least 19 bases in length and further comprises second, third and fourth base mismatches in the guide strand within base 9 to the 3' terminus, such as where all of said first, second, third and fourth base mismatches are located within base 9 to the 3' terminus. The double-stranded RNA may be at least 19 bases in length and further comprises second, third, fourth and fifth base mismatches in the guide strand within base 9 to the 3' terminus, including where all of said first, second, third, fourth and fifth base mismatches are located within base 9 to the 3' terminus.

In yet another embodiment, there is provided a composition of matter comprising a double-stranded RNA of 15-30 bases that targets said expanded CAG repeat region of a disease protein mRNA, and said double-stranded RNA further contains 1, 2, 3, 4 or 5 base mismatches as compared to the CAG repeat, wherein said double-stranded RNA contains no more than one base mismatch in a seed sequence. The CAG repeat region may be about 125 repeats or less in size. The double-stranded RNA may be 19 to about 21 bases in length. The disease protein may be Huntingtin, ataxin-3, ataxin-1, ataxin-2 or atrophin1. The double-stranded RNA may be dispersed in a lipid vehicle or saline solution.

The double-stranded RNA may comprise one or more chemically-modified bases, such as a 2'-O-methyl modified nucleotide, a nucleotide comprising a 5'-phosphorothioate group, a terminal nucleotide linked to a cholesteryl derivative or dodecanoic acid bisdecylamide group, a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, or a non-natural base comprising nucleotide. The guide strand or the passenger strand may contain the chemically-modified base, or both the guide and passenger strands may contain at least one chemically-modified base. The double-stranded RNA may comprise a non-natural internucleotide linkage, such as a phosphorothioate linkage. The double-stranded RNA may further comprise an inserted base as compared to said CAG repeat. The inserted based may be in the guide strand.

The double-stranded RNA may further target a repeat region junction. The double-stranded RNA may comprise at least 15 bases and said first base mismatch maybe flanked by at least 7 bases on both the 5' and 3' ends of said double-stranded RNA. The first base mismatch may be in the guide strand. The double-stranded RNA may be further comprise a second base mismatch, such as in the passenger strand, or both in the guide strand. The double-stranded RNA may comprise at least 16 bases and said first and second base mismatches may be adjacent and flanked by at least 7 bases on both the 5' and 3' ends of said double-stranded RNA. The double-stranded RNA may be at least 19 bases in length and said second base mismatch, or both said first and second base mismatches, may be located within base 9 to the 3' terminus. The double-stranded RNA may be at least 19 bases in length and may further comprises second and third base mismatches in the guide strand within base 9 to the 3' terminus, including where all of said, first, second and third base mismatches are located within base 9 to the 3' terminus. The double-stranded RNA may be at least 19 bases in length and further comprises second, third and fourth base mismatches in the guide strand within base 9 to the 3' terminus, such as where all of said first, second, third and fourth base mismatches are located within base 9 to the 3' terminus. The double-stranded RNA may be at least 19 bases in length and further comprises second, third, fourth and fifth base mismatches in the guide strand within base 9 to the 3' terminus, including where all of said first, second, third, fourth and fifth base mismatches are located within base 9 to the 3' terminus.

The double-stranded RNA may, in particular, comprise a double-stranded RNA selected from the group consisting of P8, P9, P10, P10R, P11, P910, P4b, P9b, P10b, P11b, P910b, RepC-b, RebU-b, MP9, MP910, MP9b, MP10b, MP11b, MRC/b and MRU/b, MP9/b-34, MP10-34, MP11-34, MP9/b-33, MP10-33, MP11-33, G8911, G91911, G891011, G8910, C891011, U8910, U8911, U91011, U891011, siPM3 and siPM4.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to these drawings and the detailed description presented below.

FIG. 1. Table of RNA sequences used in the studies. REP is the parent compound with full 19 base complementarity to the CAG repeat within HTT mRNA. The other RNAs have mismatched bases relative to the CAG repeat within HTT mRNA (shown italicized and underlined). The strand shown is the antisense or guide strand. The sense or passenger strands of the RNA duplexes are not shown. The identity of the duplexes is described in the data figures. (SEQ ID NOS: 180, 181, 183, 184, 1, 3, 5, 7, 9, 185, 186, 187, 11, 190, 188)

FIGS. 2 A-K. Western analysis of potency and selectivity for inhibition of HTT expression by duplex RNAs. (FIG. 2A) P4, (FIG. 2B) P6, (FIG. 2C) P7, (FIG. 2D) P8, (FIG. 2E) P9, (FIG. 2F) P10, (FIG. 2G) P10R, (FIG. 2H) P11, (FIG. 2I) P12, (FIG. 2J) 13, and (FIG. 2K) P16. RNAs were added to GM04281 cells (69/17 repeats). Mismatched bases relative to the CAG repeat within HTT mRNA are shown italicized and underlined. (SEQ ID NOS: 181, 195, 183, 196, 184, 197, 1, 2, 3, 4, 5, 6, 7, 8, 9, 10, 185, 198, 186, 199, 187, 200)

FIGS. 3A-C. Western analysis on the effect of different patterns of mismatched bases. (FIG. 3A) P910, (FIG. 3B) RM3, (FIG. 3C) RM4. RNAs were added to GM04281 cells (69/17 repeats). Mismatched bases relative to the CAG repeat within HTT mRNA are shown italicized and underlined. (SEQ ID NOS: 11, 12, 190, 201, 188, 202)

FIG. 4. Summary of melting temperatures and $IC_{50}$ values for duplexes tested in FIGS. 1-3C. Mismatched bases relative to the CAG repeat within HTT mRNA are shown italicized and underlined. (SEQ ID NOS: 180, 20, 181, 195, 183, 196, 184, 197, 1, 2, 3, 4, 5, 6, 7, 8, 9, 10, 185, 198, 186, 199, 187, 200, 11, 12, 190, 201, 188, 202)

FIGS. 5A-E. Western analysis of effect of mismatched bases only on guide strand. (FIG. 5A) P4b, (FIG. 5B) P9b, (FIG. 5C) P10b, (FIG. 5D) P11b, and (FIG. 5E) P910b. RNAs were added to GM04281 cells (69/17 repeats). Mismatched bases relative to the CAG repeat within HTT mRNA are shown italicized and underlined. (SEQ ID NOS: 191, 18, 13, 14, 15, 16, 19, 20, 21, 22)

FIGS. 6A-D. Western analysis showing the effect of changing the register of the duplex RNA by shifting the first base over one nucleotide. RNAs were added to GM04281 cells (69/17 repeats). (FIG. 6A) REPC (no mismatched bases), (FIG. 6B) REPU (no mismatched bases), (FIG. 6C) REBC-b, and (FIG. 6D) REP-U-b. Mismatched bases relative to the CAG repeat within HTT mRNA are shown italicized and underlined. (SEQ ID NOS: 192, 24, 193, 26, 23, 24, 25, 26)

FIGS. 7A-B. Western analysis of effect of mismatch-containing RNAs in cell line GM04719 with 44 repeats. (FIG. 7A) P9 and (FIG. 7B) P910. Mismatched bases relative to the CAG repeat within HTT mRNA are shown italicized and underlined. (SEQ ID NOS: 3, 4, 11, 12)

FIGS. 8A-B. Western analysis of effect of fully complementary and mismatch-containing RNAs in a cell line with 41 repeats (GM04717, 41 mut/20 wt). (FIG. 8A) Fully complementary RNA REP, (FIG. 8B) P10b. Mismatched bases relative to the CAG repeat within HTT mRNA are shown italicized and underlined. (SEQ ID NOS: 180, 107, 15, 16)

FIG. 9. Chemically-modified duplexes. Lower case=2'-O-methyl RNA base. Mismatched bases relative to the CAG repeat with HTT mRNA target are shown italicized and underlined. s=phosphorothioate linkage between the bases. (SEQ ID NOS: 27-40)

FIG. 10. Effect on HTT expression of adding chemically-modified duplexes to GM04281 cells (69/17 repeats). Top: Duplex RNAs added at 25 nM. Bottom: Duplex RNAs added at 50 nM. Lower case=2'-O-methyl RNA base. Mismatched bases relative to the CAG repeat with HTT mRNA target are shown italicized and underlined. s=phosphorothioate linkage between the bases. (SEQ ID NOS: 27-40)

FIGS. 11A-G. Western analysis of potency and selectivity for inhibition of HTT expression by chemically-modified duplex RNAs. (FIG. 11A) MP9, (FIG. 11B) MP910, (FIG. 11C) MP9b, (FIG. 11D) MP10b, (FIG. 11E) MP11b, (FIG. 11F) MRC/b, and (FIG. 11G) MRU/b. RNAs were added to GM04281 cells (69/17 repeats). Mismatched bases relative to the CAG repeat within HTT mRNA are shown italicized and underlined.

FIG. 19A-D. Western analysis of effects of 25 nM siRNAs on ataxin-3 expression in fibroblasts GM06151(CAG 74 mut/24 wt). (FIGS. 19A-B) CM, RM4 are negative control siRNAs; REP is duplex RNA which is fully complementary to CAG repeat. P4-16 are siRNAs with one mismatched base relative to CAG repeat. P910, PM3 are siRNAs with two or three mismatched bases. (FIG. 19C) Effects of hetero-duplex siRNAs with mismatched base on their guild strand. (FIG. 19D) Effects of chemically modified siRNAs on ataxin-3 expression. Chemically-modified siRNAs are shown italicized and underlined.

FIGS. 20A-C. Western analysis of the typical siRNAs with mismatched bases on ataxin-3 expression in fibroblasts GM06151(CAG 74 mut/24 wt). siRNAs selectively inhibit mutant ataxin-3 expression at increasing concentrations. (FIG. 20A) P9, (FIG. 20B) P11, (FIG. 20C) P910.

FIG. 21A-D. Western analysis of siRNAs on HTT expression in fibroblasts with shorter CAG repeats (GM04719, CAG 44 mut/15 wt). (FIG. 21A) REP, (FIG. 21B) RC/b, (FIG. 21C) P9, (FIG. 21D) P910. Mismatched bases relative to the CAG repeat within HTT mRNA are shown italicized and underlined. $IC_{50}$ values are averages of duplicate or triplicate determinations and the western data shown is representative. (SEQ ID NOS: 180, 22, 194, 24, 3, 4, 11, 12)

FIGS. 22A-D. Western analysis of chemically modified siRNAs on HTT expression in fibroblast cells GM04719 (CAG 44 mut/15 wt). (FIG. 22A) MP9, (FIG. 22B) MRC/b, (FIG. 22C) P910, (FIG. 22D) table of siRNAs $IC_{50}$ value and selectivity. Mismatched bases relative to the CAG repeat within HTT mRNA are shown italicized and underlined. Lower case=2'-O-methyl RNA base. s=phosphorothioate linkage between the bases. $IC_{50}$ values are averages of duplicate or triplicate determinations and the western data shown is representative. (SEQ ID NOS: 27, 28, 37, 38, 29, 30)

FIGS. 23A-D. Western analysis of effect of siRNAs in fibroblast cells GM04717 (CAG 41 mut/20 wt). (FIG. 23A) REP, (FIG. 23B) P9, (FIG. 23C) P910, (FIG. 23D) RC/b. Mismatched bases relative to the CAG repeat within HTT mRNA are shown italicized and underlined. $IC_{50}$ values are averages of duplicate or triplicate determinations and the western data shown is representative. (SEQ ID NOS: 180, 22, 3, 4, 11, 12, 194, 24)

FIGS. 24A-D. Western analysis of chemically modified siRNAs on HTT expression in fibroblast cells GM04719 (CAG 41 mut/20 wt). (FIG. 24A) MP9, (FIG. 24B) MP910, (FIG. 24C) MRC/b, (FIG. 24D) table of siRNAs $IC_{50}$ value and selectivity. Mismatched bases relative to the CAG repeat within HTT mRNA are shown italicized and underlined. Lower case=2'-O-methyl RNA base. s=phosphorothioate linkage between the bases. $IC_{50}$ values are averages of duplicate or triplicate determinations and the western data shown is representative. (SEQ ID NOS: 27, 28, 29, 30, 37, 38)

FIGS. 26A-B. Chemically-modified siRNAs with multiple mismatched bases on HTT expression. (GM04281, CAG 69/17) (FIG. 26A) Representative western blot images of siRNAs tested at 25 nM concentration. (FIG. 26B) Averaged HTT protein levels after treatment of 25 nM siRNAs.

FIGS. 28A-B. Chemically-modified siRNAs with abasic bases on HTT expression. (GM04281, CAG 69/17) (FIG. 28A) Representative western blot images of siRNAs tested at 25 nM concentration. (FIG. 28B) Averaged HTT protein levels after treatment of 25 nM siRNAs.

FIGS. 30A-B. qPCR analysis of HTT mRNA levels after treatment of siRNAs. (FIG. 30A) 25 nM of siRNAs tested in HD patient fibroblasts (GM04719, CAG 44/15). (FIG. 30B) 12 nM of siRNAs tested in HD patient fibroblasts (GM04281, CAG 69/17). siHdh1 is an unmodified siRNA targeting the outside region from CAG repeat. HTT/A is a chemically modified positive control siRNA which is provided by Alnylam Pharmaceuticals.

(FIG. 36A) Effects of 25 nM siRNAs on ataxin-3 expression. (FIG. 36B) Comparison of 25 nM siRNAs with central mismatched bases on ataxin-3 expression. (FIG. 36C) siRNAs P9, P11 P910, PM3, and PM4 selectively inhibit mutant ataxin-3 expression. Representative gel images are presented. Quantification and a nonlinear fitting curve of ataxin-3 expression is plotted from multiple experiments. Error bars are SEM.

DETAILED DESCRIPTION OF THE INVENTION

Figure 12:
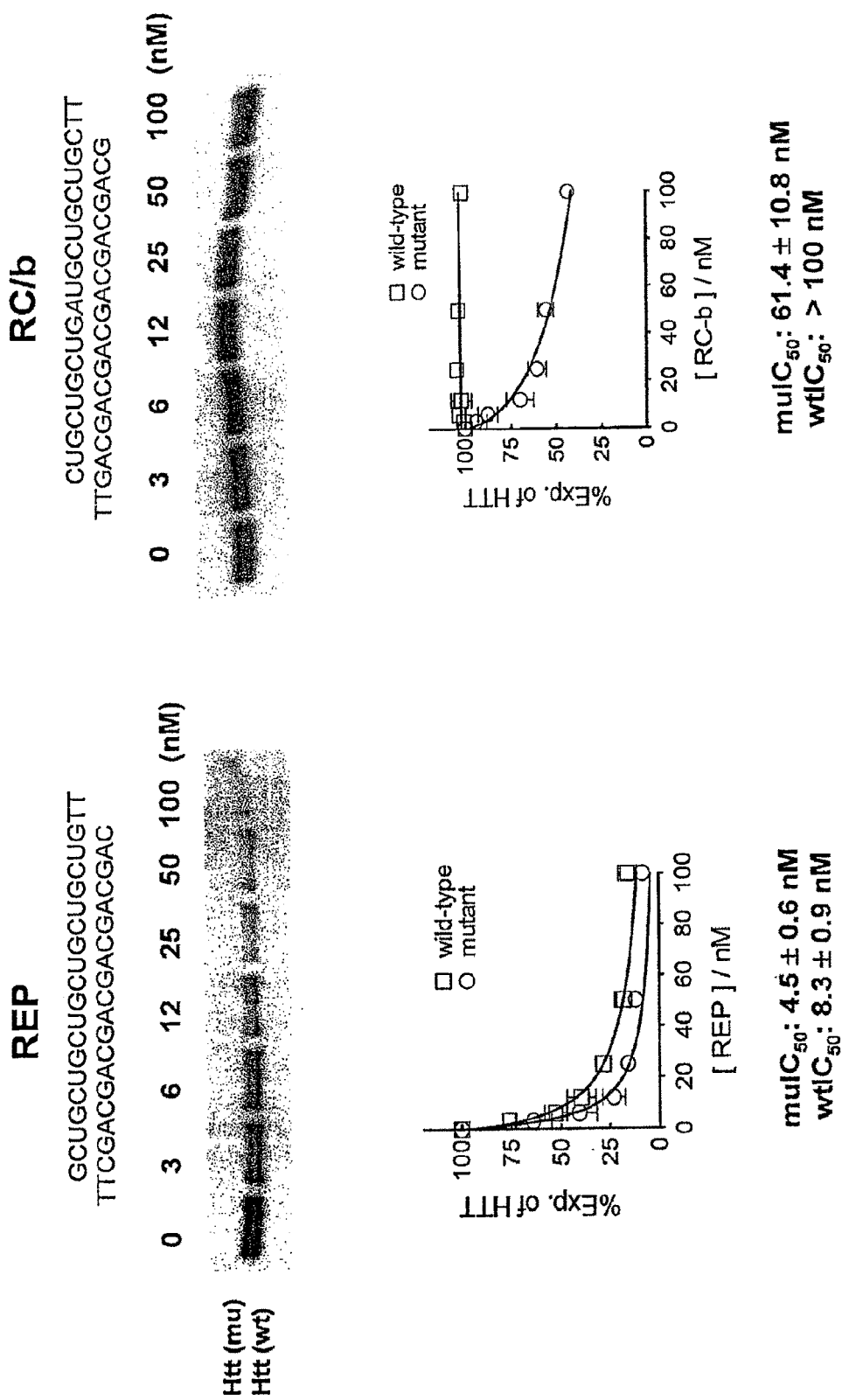
FIG. 12. Effects of siRNA targeting CAG repeat on HTT expression in GM04719 fibroblasts with shorter repeats (CAG 44/15). Left hand panel is siRNA REP; right hand panel is siRNA RC/b. Mismatched bases relative to the CAG repeat with HTT mRNA target are shown italicized and underlined. (SEQ ID NOS: 180, 18, 194, 24)

As discussed above, CAG-repeat-related diseases present significant obstacles with respect to the selective inhibition of disease versus normal protein production. As shown in the data here presented by the inventors, double-stranded RNAs can exploit differences in the number of triplet repeats and can achieve allele-selective inhibition of expression of polyglutamine containing proteins such as HTT or ataxin-3. While selectivity is generally achieved even though attacking complementary target sequences, it surprisingly turns out that introducing a mismatch greatly improves the ability of double-stranded RNAs to selectively inhibit mutant protein expression versus wild-type. The target can be within the CAG repeat or at the 5' or 3' junction between the repeat and the rest of the mRNA coding sequence. Further, chemically-modified RNAs (in one or both strands) also retain selective inhibitory activity. These and other aspects of the invention are described in detail below.

I. POLYGLUTAMINE REPEAT DISEASES

The polyglutamine disorders include nine neurodegenerative disorders that are inherited gain-of-function diseases caused by expansion of a translated CAG repeat. Even though the disease-causing proteins are widely expressed, specific collections of neurons are more susceptible in each disease. There is substantial evidence linking the function of the polyglutamine disease-associated proteins with the regulation of gene transcription, and a variety of mechanisms have been suggested by which the polyglutamine proteins impact upon transcription, including altering the function of a very specific DNA-binding factor like the AR (SBMA), general DNA-binding proteins like TBP (SCA17), Sp1, TFIID and TFIIF (HD), chromatin structure (SCAT), coregulators (HD, SCAT, and DRPLA), and possibly the ubiquitin-proteasome system (SCA3). There also is evidence they impact other biological processes important for neuronal function, for example, intracellular trafficking (Gunawardena and Goldstein, 2005) and the mitochondrial/energy metabolism (Browne and Beal, 2004). Some of these disorders are discussed in greater detail below.

A. Huntington Disease

Huntington disease, also called Huntington's chorea, chorea major, or HD, is a genetic neurological disorder characterized by abnormal body movements called chorea and a lack of coordination; it also affects a number of mental abilities and some aspects of behavior. In 1993, the gene causing HD was found, making it one of the first inherited genetic disorders for which an accurate test could be performed. The accession number for Huntingtin is NM_002111.

The gene causing the disorder is dominant and may, therefore, be inherited from a single parent. Global incidence varies, from 3 to 7 per 100,000 people of Western European descent, down to 1 per 1,000,000 of Asian and African descent. The onset of physical symptoms in HD occur in a large range around a mean of a person's late forties to early fifties. If symptoms become noticeable before a person is the age of twenty, then their condition is known as Juvenile HD.

A trinucleotide repeat expansion occurs in the Huntingtin gene, which produces mutant Huntingtin protein. The presence of this protein increases the rate of neuron cell death in select areas of the brain, affecting certain neurological functions. The loss of neurons isn't fatal, but complications caused by symptoms reduce life expectancy. There is currently no proven cure, so symptoms are managed with a range of medications and supportive services.

Symptoms increase in severity progressively, but are not often recognised until they reach certain stages. Physical symptoms are usually the first to cause problems and be noticed, but these are accompanied by cognitive and psychiatric ones which aren't often recognized. Almost everyone with HD eventually exhibits all physical symptoms, but cognitive symptoms vary, and so any psychopathological problems caused by these, also vary per individual. The symptoms of juvenile HD differ in that they generally progress faster and are more likely to exhibit rigidity and bradykinesia instead of chorea and often include seizures.

The most characteristic symptoms are jerky, random, and uncontrollable movements called chorea, although sometimes very slow movement and stiffness (bradykinesia, dystonia) can occur instead or in later stages. These abnormal movements are initially exhibited as general lack of coordination, an unsteady gait and slurring of speech. As the disease progresses, any function that requires muscle control is affected, this causes reduced physical stability, abnormal facial expression, impaired speech comprehensibility, and difficulties chewing and swallowing. Eating difficulties commonly cause weight loss. HD has been associated with sleep cycle disturbances, including insomnia and rapid eye movement sleep alterations.

Selective cognitive abilities are progressively impaired, including executive function (planning, cognitive flexibility, abstract thinking, rule acquisition, initiating appropriate actions and inhibiting inappropriate actions), psychomotor function (slowing of thought processes to control muscles), perceptual and spatial skills of self and surrounding environment, selection of correct methods of remembering information (but not actual memory itself), short-term memory, and ability to learn new skills, depending on the pathology of the individual.

Psychopathological symptoms vary more than cognitive and physical ones, and may include anxiety, depression, a reduced display of emotions (blunted affect) and decreased ability to recognize negative expressions like anger, disgust, fear or sadness in others, egocentrism, aggression, and compulsive behavior. The latter can cause, or worsen, hypersexuality and addictions such as alcoholism and gambling.

HD is autosomal dominant, needing only one affected allele from either parent to inherit the disease. Although this generally means there is a one in two chance of inheriting the disorder from an affected parent, the inheritance of HD is more complex due to potential dynamic mutations, where DNA replication does not produce an exact copy of itself. This can cause the number of repeats to change in successive generations. This can mean that a parent with a count close to the threshold, may pass on a gene with a count either side of the threshold. Repeat counts maternally inherited are usually similar, whereas paternally inherited ones tend to increase. This potential increase in repeats in successive generations is known as anticipation. In families where neither parent has HD, new mutations account for truly sporadic cases of the disease. The frequency of these de novo mutations is extremely low.

Homozygous individuals, who carry two mutated genes because both parents passed on one, are rare. While HD seemed to be the first disease for which homozygotes did not differ in clinical expression or course from typical heterozygotes, more recent analysis suggest that homozygosity affects the phenotype and the rate of disease progression though it does not alter the age of onset suggesting that the mechanisms underlying the onset and the progression are different.

Huntingtin protein is variable in its structure as there are many polymorphisms of the gene which can lead to variable numbers of glutamine residues present in the protein. In its wild-type (normal) form, it contains 6-35 glutamine residues; however, in individuals affected by HD, it contains between 36-155 glutamine residues. Huntingtin has a predicted mass of ~350 kDa, however, this varies and is largely dependent on the number of glutamine residues in the protein. Normal huntingtin is generally accepted to be 3144 amino acids in size.

Two transcriptional pathways are more extensively implicated in HD—the CBP/p300 and Sp1 pathways—and these are transcription factors whose functions are vital for the expression of many genes. The postulated relationship between CBP and HD stems from studies showing that CBP is found in polyglutamine aggregates (see Kazantsev et al., 1999). Consequently, it was demonstrated that huntingtin and CBP interact via their polyglutamine stretches, that huntingtin with an expanded polyglutamine tract interferes with CBP-activated gene expression, and that overexpression of CBP rescued polyglutamine-induced toxicity in cultured cells (Nucifora et al., 2001; Steffan et al., 2001). Mutant huntingtin was also shown to interact with the acetyltransferase domain of CBP and inhibit the acetyltransferase activity of CBP, p300, and the p300/CBP-associated factor P/CAF (Steffan et al., 2001).

These observations prompted a hypothesis whereby the pathogenic process was linked to the state of histone acetylation; specifically, mutant huntingtin induced a state of decreased histone acetylation and thus altered gene expression. Support for this hypothesis was obtained in a *Drosophila* HD model expressing an N-terminal fragment of huntingtin with an expanded polyglutamine tract in the eye. Administration of inhibitors of histone deacetylase arrested the neurodegeneration and lethality (Steffan et al., 2001). Protective effects of HDAC inhibitors have been reported for other polyglutamine disorders, prompting the concept that at least some of the observed effects in polyglutamine disorders are due to alterations in histone acetylation (Hughes 2002). Studies published in 2002 revealed that the N-terminal fragment of huntingtin and intact huntingtin interact with Sp1 (Dunah et al., 2002; Li et al., 2002), a transcriptional activator that binds to upstream GC-rich elements in certain promoters. It is the glutamine-rich transactivation domain of Sp1 that selectively binds and directs core components of the general transcriptional complex such as TFIID, TBP and other TBP-associated factors to Sp1-dependent sites of transcription. In vitro transcription studies have gone on to show that in addition to targeting Sp1, mutant huntingtin targets TFIID and TFIIF, members of the core transcriptional complex (Zhai et al. 2005). Mutant huntingtin was shown to interact with the RAP30 subunit of TFIIF. Notably, overexpression of RAP30 alleviated both mutant huntingtin-induced toxicity and transcriptional repression of the dopamine D2 receptor gene. These results indicate that mutant huntingtin may interfere with multiple components of the transcription machinery.

There is no treatment to fully arrest the progression of the disease, but symptoms can be reduced or alleviated through the use of medication and care methods. Huntington mice models exposed to better husbandry techniques, especially better access to food and water, lived much longer than mice that were not well cared for.

Standard treatments to alleviate emotional symptoms include the use of antidepressants and sedatives, with antipsychotics (in low doses) for psychotic symptoms. Speech therapy helps by improving speech and swallowing methods; this therapy is more effective if started early on, as the ability to learn is reduced as the disease progresses. A two-year pilot study, of intensive speech, pyschiatric and physical therapy, applied to inpatient rehabilitation, showed motor decline was greatly reduced.

Nutrition is an important part of treatment; most third and fourth stage HD sufferers need two to three times the calories of the average person to maintain body weight. Healthier foods in pre-symptomatic and earlier stages may slow down the onset and progression of the disease. High calorie intake in pre-symptomatic and earlier stages has been shown to speed up the onset and reduce IQ level. Thickening agent can be added to drinks as swallowing becomes more difficult, as thicker fluids are easier and safer to swallow. The option of using a stomach PEG is available when eating becomes too hazardous or uncomfortable; this greatly reduces the chances of aspiration of food, and the subsequent increased risk of pneumonia, and increases the amount of nutrients and calories that can be ingested.

EPA, an Omega-3 fatty acid, may slow and possibly reverse the progression of the disease. As of April 2008, it is in FDA clinical trial as ethyl-EPA, (brand name Miraxion), for prescription use. Clinical trials utilise 2 grams per day of EPA. In the United States, it is available over the counter in lower concentrations in Omega-3 and fish oil supplements.

B. Spinocerebellar Ataxias

Spinocerebellar ataxia (SCA) is one of a group of genetic disorders characterized by slowly progressive incoordination of gait and often associated with poor coordination of hands, speech, and eye movements. Frequently, atrophy of the cerebellum occurs. As with other forms of ataxia, SCA results in unsteady and clumsy motion of the body due to a failure of the fine coordination of muscle movements, along with other symptoms. The symptoms of the condition vary with the specific type (there are several), and with the individual patient. Generally, a person with ataxia retains full mental capacity but may progressively lose physical control.

There is no known cure for spinocerebellar ataxia, which is a progressive disease (it gets worse with time), although not all types cause equally severe disability. Treatments are generally limited to softening symptoms, not the disease itself. The condition can be irreversible. A person with this disease will usually end up needing to use a wheelchair, and eventually they may need assistance to perform daily tasks. The treatment of incoordination or ataxia, then mostly involves the use of adaptive devices to allow the ataxia individual to maintain as much independence as possible. Such devices may include a cane, crutches, walker, or wheelchair for those with impaired gait; devices to assist with writing, feeding, and self care if hand and arm coordination are impaired; and communication devices for those with impaired speech.

Many patients with hereditary or idiopathic forms of ataxia have other symptoms in addition to ataxia. Medications or other therapies might be appropriate for some of these symptoms, which could include tremor, stiffness, depression, spasticity, and sleep disorders, among others. Both onset of initial symptoms and duration of disease can be subject to variation, and it can be easily misdiagnosed as another neurological condition, such as multiple sclerosis (MS).

Spinocerebellar ataxia type 1 (SCAT) is an autosomal dominant ataxia that results in gait ataxia, dysarthria, and bulbar dysfunction, with death usually between 10 and 15 years after the onset of symptoms. The average age of onset is in the $4^{th}$ decade of life. Despite the protein ataxin-1 being widely expressed in the central nervous system, the most frequently seen and most severe pathological alterations are restricted to loss of Purkinje cells in the cerebellar cortex, as well as loss of neurons in the inferior olivary nuclei, the cerebellar dentate nuclei and the red nuclei.

Normally ataxin-1, the product of the SCA1 gene, is prominently located in the nuclei of neurons (Servadio et al., 1995). Indication that SCA1 pathogenesis was due to alterations in nuclear function began with the observation that for mutant ataxin-1 to cause disease, it had to enter the nucleus of Purkinje cells (Klement et al., 1998). Consequent studies revealed that wild-type ataxin-1 has properties consistent with a role in the regulation of gene expression in the nucleus. These include the ability to bind RNA (Yue et al., 2001) and to shuttle between the nucleus and cytoplasm (Irwin et al., 2005).

Spinocerebellar ataxia type 2 (SCA2) is characterized by progressive cerebellar ataxia, including nystagmus, slow saccadic eye movements and, in some individuals, ophthalmoparesis. Pyramidal findings are present; deep tendon reflexes are brisk early on and are absent later in the course. Age of onset is typically in the $3^{rd}$ to $4^{th}$ decade with a 10-15-year disease duration.

The diagnosis of SCA2 rests upon the use of molecular genetic testing to detect an abnormal CAG trinucleotide repeat expansion of the ATXN2 gene. Affected individuals have alleles with greater than 32 CAG trinucleotide repeats. Such testing detects nearly 100% of cases and is available in clinical laboratories.

Management of individuals with SCA2 is supportive. Affected individuals should maintain activity. Canes and walkers help prevent falls; grab bars, raised toilet seats, and ramps to accommodate motorized chairs may be necessary. Speech therapy and communication devices such as writing pads and computer-based devices may benefit those with dysarthria. Weighted eating utensils and dressing hooks help maintain a sense of independence. When dysphagia becomes troublesome, video esophagrams can identify the consistency of food least likely to trigger aspiration. Vitamin supplements are recommended; weight control prevents difficulties with ambulation and mobility. Affected individuals should avoid alcohol and medications known to affect cerebellar function.

Spinocerebellar ataxia type 3 (SCA3), also known as Machado Joseph disease (MJD), is the most common of the autosomal dominantly inherited ataxias with several genetic features that distinguish it from many of the other polyglutamine disorders. In contrast to HD and SCAT, where the repeat threshold for mutant alleles is <40, in SCA3 the repeat threshold for the mutant alleles is >50 repeats. Moreover, although other polyglutamine disorders behave as pure dominant diseases, SCA3/MJD homozygous patients have a more severe disease presentation than individuals having only a single mutant allele. Onset is normally in the $4^{th}$ decade, and duration averages about 10 years.

Ataxin-3 contains an N-terminal Josephin domain (JD) with recently ascribed ubiquitin protease activity (Burnett et al., 2003; Scheel et al., 2003), two ubiquitin interacting motifs (UIMs) capable of binding ubiquitin (Chai et al., 2004; Burnett et al., 2003; Donaldson et al., 2003) followed by a polyglutamine stretch, and a C-terminal variable domain. The crystal structure of the ataxin-3 JD provided insight into the potential function of ataxin-3 as a polyubiquitin chain editing protein by demonstrating a tight connection between polyubiquitin binding and the deubiquitylating activity of ataxin-3 (Mao et al., 2005; Nicastro et al., 2005). Thus, there are considerable structural data indicating that ataxin-3 has a role in the ubiquitin and/or the ubiquitin-proteasome system. Ataxin-3 is unique from the other polyglutamine diseases in that wild-type ataxin-3 expression in *Drosophila* protects neurons from toxicity initiated by other polyglutamine-expanded proteins (Warrick et al., 2005). This protection afforded by wild-type ataxin-3 was dependent on active proteasomes and both the UIM and ubiquitin protease domains of ataxin-3.

The accession numbers for these genes are as follows: Ataxin1 (NM_000332), ataxin2 (NM 002973), and ataxin3 (NM 004993).

C. Dentatorubral and Pallidoluysian Atrophy (DRPLA)

Dentatorubral-pallidoluysian atrophy (DRPLA) is an autosomal dominant spinocerebellar degeneration caused by an expansion of a CAG repeat encoding a polyglutamine tract in the atrophin-1 protein. It is also known as Haw River Syndrome and Naito-Oyanagi disease. Several sporadic cases have been reported from Western countries, but this disorder seems to be very rare except in Japan.

DRPLA can be juvenile-onset (<20 years), early adult-onset (20-40 years), or late adult-onset (>40 years). Late adult-onset DRPLA is characterized by ataxia, choreoathetosis and dementia. Early adult-onset DRPLA also includes seizures and myoclonus. Juvenile-onset DRPLA presents with ataxia and symptoms consistent with progressive myoclonus epilepsy.

Atrophin-1 (ATN1) encodes a hydrophilic 1184 amino acid protein with several repetitive motifs including a serine-rich region, a variable length polyglutamine tract, a polyproline tract, and a region of alternating acidic and basic residues. It contains a putative nuclear localization signal in the N-terminus of the protein and a putative nuclear export signal in the C-terminus. ATN1 is ubiquitously expressed in all tissues, but proteolytically cleaved in neuronal cells. The function of ATN1 is not clear, however it is believed to be a transcriptional co-repressor. ATN1 and atrophin-2 can be co-immunoprecipitated, indicating that they may carry out some functions together in a molecular complex. Atrophin-1 may be a dispensable or redundant protein as mice bred with a null allele for atrophin-1 produce viable and fertile offspring and show no compensatory upregulation of atrophin-2. The accession number for atrophin1 is NM_001940.

DRPLA is characterized by marked, generalized brain atrophy and the accumulation of atrophin-1 with expanded glutamine stretches. Mutant atrophin-1 proteins have been found in neuronal intranuclear inclusions (NII) and diffusely accumulated in the neuronal nuclei. While the role of NIIs (pathologic or protective) is unclear, the diffuse accumulation of mutant protein is regarded as toxic.

There is significant reduction in CNS tissue throughout the brain and spinal cord, with brain weights of DRPLA patients often becoming less than 1000 g. In regions lacking obvious neuronal depletion, atrophy of the neuropil is noted.

The globus pallidus (lateral greater than medial segment) and subthalamic nucleus demonstrate consistent neuronal loss and astrocytic gliosis. The dentate nucleus shows neuronal loss with the remaining atrophic neurons exhibiting grumose degeneration. In general, the pallidoluysian degeneration is more severe than the dentatorubral degeneration in juvenile-onset and the reverse is true for the late adult-onset.

Transgenic DRPLA mice demonstrated several neuronal abnormalities including a reduction in the number and size of dendritic spines as well as in the area of perikarya and diameter of dendrites. Spine morphology and density have been linked to learning and memory functions as well as epilepsy. The stubby-type spines seen in DRPLA mice are morphologically different from the thin and mushroom-type spines seen in Huntington's mice.

Morphometric analysis of DRPLA mouse brains has shown a loss of normal inter-microtubule spacing in neuronal axons. The microtubules were relatively compacted, suggesting abnormalities in protein transport may play a role in neuronal degeneration. In humans, atrophin-1 interacts with IRSp53, which interacts with Rho GTPases to regulate the organization of the actin cytoskeleton and the pathways that regulate lamellipodia and filopodia.

NIIs are not exclusive to DRPLA; they have been found in a variety of neurodegenerative disorders. In DRPLA, NIIs have been demonstrated in both neurons and glial cells in the striatum, pontine nuclei, inferior olive, cerebellar cortex and dentate nucleus, though the incidence of neurons with NIIs is low, roughly 1-3%. In DRPLA, the NIIs are spherical, eosinophilic structures of various sizes. They are non-membrane-bound and are composed of both granular and filamentous structures. They are ubiquitinated and may be paired or in doublet form within the nucleus.

NIIs have also been demonstrated to alter the distribution of the intranuclear structures, such as promyelocytic leukemia protein (PML) nuclear bodies. Although the role of PML bodies is unclear, they are believed to be involved in apoptosis. In neurons with NII, PML bodies in DRPLA patients form a shell or ring around the ubiquitinated core. In similar polyQ diseases, the association of this PML shell has been shown to be size-dependent with larger NIIs being PML negative. This has led to two models, one in which PML bodies represent sites for NII formation and a second in which PML bodies are involved in degradation and proteolysis of NIIs.

Filementous, atrophin-1 positive, inclusions are also observed exclusively in the cytoplasm of the dentate nucleus, which are extremely similar to the inclusions observed in the motor neurons in amyotrophic lateral sclerosis.

In DRPLA, diffuse accumulation of mutant ATN1 occurs far more extensively than NII formation. The extent and frequency of neurons showing the diffuse nuclear accumulations changes depending on CAG repeat length. It is believed that the diffuse nuclear accumulations contribute to the clinical features such as dementia and epilepsy. ATN1 contains both a nuclear localization sequence and a nuclear export sequence. Cleavage of ATN1 to an N-terminal fragment relieves ATN1 of its nuclear export signal and concentrates it in the nucleus. Increased nuclear concentrations have been demonstrated via transfection assay to enhance cellular toxicity.

In both the juvenile and adult forms, regions in which more than 40% of neurons became immunoreactive to 1C2 (a monoclonal antibody against expanded polyglutamine stretches) included: the nucleus basalis of Meynert, large striatal neurons, globus pallidus, subthalamic nucleus, thalamic intralaminar nucleus, lateral geniculate body, oculomotor nucleus, red nucleus, substantia nigra, trigeminal motor nucleus, nucleus raphe pontis, pontine nuclei, vestibular nucleus, inferior olive and the cerebellar dentate nucleus. The juvenile type also shows reactivity in the cerebral cortex, hippocampal CA1 area, and the reticular formation of the brainstem. Nuclei containing accumulations of mutant atrophin-1 are deformed with nuclear membrane indentations.

Diagnosis of DRPLA rests of positive family history, clinical findings, and genetic testing. Family history can be difficult to obtain if a relative was misdiagnosed, died young, or experiences late onset of symptoms. Other diseases in the differential diagnosis of adult-onset DRPLA include Huntington's and the spinocerebellar ataxias. For juvenile-onset, familial essential myoclonus and epilepsy (FEME), Lafora, Unverricht-Lundborg, Neuroaxonal dystrophy, Gaucher's disease, Sialidosis, and Galactosialidosis. To quantify the extent of the disease, an MRI, EEG and neuropsychological testing are recommended. Seizures are treated with anticonvulsants and psychiatric disturbances with psychotropic medications.

II. NUCLEIC ACID ANALOGS

A. Analogs

The present invention contemplates the use of double-stranded RNAs that hybridize to expanded CAG repeats. The double-stranded RNAs may contain non-natural bases and also may contain non-natural backbone linkages.

A locked nucleic acid (LNA), often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in the oligonucleotide whenever desired. Such oligomers are commercially available. The locked ribose conformation enhances base stacking and backbone pre-organization. This significantly increases the thermal stability (melting temperature) of oligonucleotides (Kaur et al., 2006).

LNA nucleotides are used to increase the sensitivity and specificity of expression in DNA microarrays, FISH probes, real-time PCR probes and other molecular biology techniques based on oligonucleotides. For the in situ detection of miRNA, the use of LNA was as of 2005 the only efficient method. A triplet of LNA nucleotides surrounding a single-base mismatch site maximizes LNA probe specificity unless the probe contains the guanine base of G-T mismatch (You et al., 2006).

Other oligonucleotide modifications can be made to produce the RNAs of the present invention. For example, stability against nuclease degradation has been achieved by introducing a phosphorothioate (P=S) backbone linkage at the 3' end for exonuclease resistance and 2' modifications (2'-OMe, 2'-F and related) for endonuclease resistance (WO 2005115481; Li et al., 2005; Choung et al., 2006). A motif having entirely of 2'-O-methyl and 2'-fluoro nucleotides has shown enhanced plasma stability and increased in vitro potency (Allerson et al., 2005). The incorporation of 2'-O-Me and 2'-O-MOE does not have a notable effect on activity (Prakash et al., 2005).

Sequences containing a 4'-thioribose modification have been shown to have a stability 600 times greater than that of natural RNA (Hoshika et al, 2004). Crystal structure studies reveal that 4'-thioriboses adopt conformations very similar to the C3'-endo pucker observed for unmodified sugars in the native duplex (Haeberli et al., 2005). Stretches of 4'-thio-RNA were well tolerated in both the guide and nonguide strands. However, optimization of both the number and the placement of 4'-thioribonucleosides is necessary for maximal potency.

In the boranophosphate linkage, a non-bridging phosphodiester oxygen is replaced by an isoelectronic borane ($BH_3—$) moiety. Boranophosphate siRNAs have been synthesized by enzymatic routes using T7 RNA polymerase and a boranophosphate ribonucleoside triphosphate in the transcription reaction. Boranophosphate siRNAs are more active than native siRNAs if the center of the guide strand is not modified, and they may be at least ten times more nuclease resistant than unmodified siRNAs (Hall et al., 2004; Hall et al., 2006).

Certain terminal conjugates have been reported to improve or direct cellular uptake. For example, nucleic acid analogs conjugated with cholesterol improve in vitro and in vivo cell permeation in liver cells (Rand et al., 2005). Soutschek et al. (2004) have reported on the use of chemically-stabilized and cholesterol-conjugated siRNAs have markedly improved pharmacological properties in vitro and in vivo. Chemically-stabilized siRNAs with partial phosphorothioate backbone and 2'-O-methyl sugar modifications on the sense and antisense strands (discussed above) showed significantly enhanced resistance towards degradation by exo- and endonucleases in serum and in tissue homogenates, and the conjugation of cholesterol to the 3' end of the sense strand of an NAA by means of a pyrrolidine linker does not result in a significant loss of gene-silencing activity in cell culture. These studies demonstrates that cholesterol conjugation significantly improves in vivo pharmacological properties of NAAs.

LNA bases may be included in a RNA backbone, but they can also be in a backbone of 2'-O-methyl RNA, 2'-methoxyethyl RNA, or 2'-fluoro RNA. These molecules may utilize either a phosphodiester or phosphorothioate backbone.

U.S. Patent Publication 2008/0015162, incorporated herein by reference, provide additional examples of nucleic acid analogs useful in the present invention. The following excerpts are derived from that document and are exemplary in nature only:

In certain embodiments, oligomeric compounds comprise one or more modified monomers, including 2'-modified sugars, such as nucleosides and nucleotides, with 2'-substituents such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_m)$, or O—$CH_2$—C(=O)—N$(R_m)(R_n)$, where each $R_m$ and $R_n$ is, independently, H or substituted or unsubstituted $C_1$-$C_{10}$ alkyl.

Oligomeric compounds provided herein may comprise one or more monomer, including a nucleoside or nucleotide, having a modified sugar moiety. For example, the furanosyl sugar ring of a nucleoside can be modified in a number of ways including, but not limited to, addition of a substituent group, bridging of two non-geminal ring atoms to form a bicyclic nucleic acid (BNA). Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,531,584; and 6,600,032; and WO 2005/121371.

In certain embodiments, oligomeric compounds comprise one or more monomers that is a BNA. In certain such embodiments, BNAs include, but are not limited to, (A) α-L-Methyleneoxy (4'-$CH_2$—O-2') BNA, (B) β-D-Methyleneoxy (4'-$CH_2$—O-2') BNA, (C) Ethyleneoxy (4'-$(CH_2)_2$—O-2') BNA, (D) Aminooxy (4'-$CH_2$—O—N(R)-2') BNA and (E) Oxyamino (4'-$CH_2$—N(R)—O-2') BNA.

In certain embodiments, BNA compounds include, but are not limited to, compounds having at least one bridge between the 4' and the 2' position of the sugar wherein each of the bridges independently comprises 1 or from 2 to 4 linked groups independently selected from —[C($R_1$)($R_2$)]$_n$—, —C($R_1$)=C($R_2$)—, —C($R_1$)=N—, —C(=N$R_1$)—, —C(=O)—, —C(=S)—, —O—, —Si($R_1$)$_2$—, —S(=O)$_x$— and —N($R_1$)—; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl; substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In one embodiment, each of the bridges of the BNA compounds is, independently, —[C($R_1$)($R_2$)]$_n$—, —[C($R_1$)($R_2$)]$_n$—O—, —C($R_1R_2$)—N($R_1$)—O— or —C($R_1R_2$)—N($R_1$)—. In another embodiment, each of said bridges is, independently, 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N($R_1$)-2' and 4'-$CH_2$—N($R_1$)—O-2'- wherein each $R_1$ is, independently, H, a protecting group or $C_1$-$C_{12}$ alkyl.

Certain BNA's have been prepared and disclosed in the patent literature as well as in scientific literature (Singh et al., 1998; Koshkin et al., 1998; Wahlestedt et al., 2000; Kumar et al., 1998; WO 94/14226; WO 2005/021570; Singh et al., 1998. Examples of issued US patents and published applications that disclose BNAs include, for example, U.S. Pat. Nos. 7,053,207; 6,268,490; 6,770,748; 6,794,499; 7,034,133; and 6,525,191; and U.S. Patent Publication Nos. 2004/0171570; 2004/0219565; 2004/0014959; 2003/0207841; 2004/0143114; and 2003/0082807.

Also provided herein are BNAs in which the 2'-hydroxyl group of the ribosyl sugar ring is linked to the 4' carbon atom of the sugar ring thereby forming a methyleneoxy (4'-$CH_2$—O-2) linkage to form the bicyclic sugar moiety (reviewed in Elayadi et al., 2001; Braasch et al., 2001; and Orum et al., 2001; see also U.S. Pat. Nos. 6,268,490 and 6,670,461). The linkage can be a methylene (—$CH_2$—) group bridging the 2' oxygen atom and the 4' carbon atom, for which the term methyleneoxy (4'-$CH_2$—O-2') BNA is used for the bicyclic moiety; in the case of an ethylene group in this position, the term ethyleneoxy (4'-$CH_2CH_2$—O-2') BNA is used (Singh et al., 1998; Morita et al., 2003). Methyleneoxy (4'-$CH_2$—O-2') BNA and other bicyclic sugar analogs display very high duplex thermal stabilities with complementary DNA and RNA (Tm=+3 to +10° C.), stability towards 3'-exonucleolytic degradation and good solubility properties. Potent and nontoxic antisense oligonucleotides comprising BNAs have been described (Wahlestedt et al., 2000).

An isomer of methyleneoxy (4'-CH$_2$—O-2') BNA that has also been discussed is α-L-methyleneoxy (4'-CH$_2$—O-2) BNA which has been shown to have superior stability against a 3'-exonuclease. The α-L-methyleneoxy (4'-CH$_2$—O-2') BNA's were incorporated into antisense gapmers and chimeras that showed potent antisense activity (Frieden et al., 2003).

The synthesis and preparation of the methyleneoxy (4'-CH$_2$—O-2') BNA monomers adenine, cytosine, guanine, 5-methyl-cytosine, thymine and uracil, along with their oligomerization, and nucleic acid recognition properties have been described (Koshkin et al., 1998). BNAs and preparation thereof are also described in WO 98/39352 and WO 99/14226.

Analogs of methyleneoxy (4'-CH$_2$—O-2') BNA, phosphorothioate-methyleneoxy (4'-CH$_2$—O-2') BNA and 2'-thio-BNAs, have also been prepared (Kumar et al., 1998). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., 1998). In addition, 2'-amino- and 2'-methylamino-BNA's have been prepared and the thermal stability of their duplexes with complementary RNA and DNA strands has been previously reported.

In certain embodiments, the oligomeric compounds comprise one or more high affinity monomers provided that the oligomeric compound does not comprise a nucleotide comprising a 2'-O(CH$_2$)—H, wherein n is one to six. In certain embodiments, the oligomeric compounds including, but no limited to short antisense compounds of the present invention, comprise one or more high affinity monomer provided that the oligomeric compound does not comprise a nucleotide comprising a 2'-OCH$_3$ or a 2'-O(CH$_2$)$_2$OCH$_3$. In certain embodiments, the oligomeric compounds including, but not limited to short antisense compounds of the present invention, comprise one or more high affinity monomer provided that the oligomeric compound does not comprise a α-L-Methyleneoxy (4'-CH$_2$—O-2') BNA. In certain embodiments, the oligomeric compounds including, but no limited to short antisense compounds of the present invention, comprise one or more high affinity monomer provided that the oligomeric compound does not comprise a β-D-Methyleneoxy (4'-CH$_2$—O-2') BNA. In certain embodiments, the oligomeric compounds including, but no limited to short antisense compounds of the present invention, comprise one or more high affinity monomer provided that the oligomeric compound does not comprise a α-L-Methyleneoxy (4'-CH$_2$—O-2') BNA or a β-D-Methyleneoxy (4'-CH$_2$—O-2') BNA.

The naturally occurring base portion of a nucleoside is typically a heterocyclic base. The two most common classes of such heterocyclic bases are the purines and the pyrimidines. For those nucleosides that include a pentofuranosyl sugar, a phosphate group can be linked to the 2', 3' or 5' hydroxyl moiety of the sugar. In forming oligonucleotides, those phosphate groups covalently link adjacent nucleosides to one another to form a linear polymeric compound. Within oligonucleotides, the phosphate groups are commonly referred to as forming the internucleotide backbone of the oligonucleotide. The naturally-occurring linkage or backbone of RNA is a 3' to 5' phosphodiester linkage.

In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

In one embodiment, each of the substituted groups, is, independently, mono- or poly-substituted with optionally protected substituent groups independently selected from halogen, oxo, hydroxyl, OJ$_1$, NJ$_1$J$_2$, SJ$_1$, N$_3$, OC(=X)J$_1$, OC(=X)NJ$_1$J$_2$, NJ$_3$C(=X)NJ$_1$J$_2$ and CN, wherein each J$_1$, J$_2$ and J$_3$ is, independently, H or C$_1$-C$_6$ alkyl, and X is O, S or NJ$_1$.

In certain such embodiments, each of the substituted groups, is, independently, mono- or poly-substituted with substituent groups independently selected from halogen, oxo, hydroxyl, OJ$_1$, NJ$_1$J$_2$, SJ$_1$, N$_3$, OC(=X)J$_1$, and NJ$_3$C(=X)NJ$_1$J$_2$, wherein each J$_1$, J$_2$ and J$_3$ is, independently, H, C$_1$-C$_6$ alkyl, or substituted C$_1$-C$_6$ alkyl and X is O or NJ$_1$.

In one embodiment, each of the substituted groups, is, independently, mono or poly substituted with optionally protected substituent groups independently selected from halogen, oxo, hydroxyl, OJ$_1$, NJ$_1$J$_2$, SJ$_1$, N$_3$, OC(=X)J$_1$, OC(=X)NJ$_1$J$_2$, NJ$_3$C(=X)NJ$_1$J$_2$ and CN, wherein each J$_1$, J$_2$ and J$_3$ is, independently, H or C$_1$-C$_6$ alkyl, and X is O, S or NJ$_1$.

In one embodiment, each of the substituted groups, is, independently, mono- or poly-substituted with substituent groups independently selected from halogen, oxo, hydroxyl, OJ$_1$, NJ$_1$J$_2$, SJ$_1$, N$_3$, OC(=X)J$_1$, and NJ$_3$C(=X)NJ$_1$J$_2$, wherein each J$_1$, J$_2$ and J$_3$ is, independently, H or C$_1$-C$_6$ alkyl, and X is O or NJ$_1$.

Described herein are linking groups that link monomers (including, but not limited to, modified and unmodified nucleosides and nucleotides) together, thereby forming an oligomeric compound. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N (CH$_3$)—). Oligomeric compounds having non-phosphorus linking groups are referred to as oligonucleosides. Modified linkages, compared to natural phosphodiester linkages, can be used to alter, typically increase, nuclease resistance of the oligomeric compound. In certain embodiments, linkages having a chiral atom can be prepared a racemic mixtures, as separate enantiomers. Representative chiral linkages include, but are not limited to, alkylphosphonates and phosphorothioates. Methods of preparation of phosphorous-containing and non-phosphorous-containing linkages are well known to those skilled in the art.

The oligomeric compounds described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids et al. Included in the antisense compounds provided herein are all such possible isomers, as well as their racemic and optically pure forms.

In certain embodiments, provided herein are oligomeric compounds having reactive phosphorus groups useful for forming linkages including for example phosphodiester and phosphorothioate internucleoside linkages. Methods of preparation and/or purification of precursors or oligomeric compounds are not a limitation of the compositions or methods provided herein. Methods for synthesis and purification of oligomeric compounds including DNA, RNA, oligonucleotides, oligonucleosides, and antisense compounds are well known to those skilled in the art.

Generally, oligomeric compounds comprise a plurality of monomeric subunits linked together by linking groups. Nonlimiting examples of oligomeric compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

In certain embodiments, the present invention provides chimeric oligomeric compounds. In certain such embodiments, chimeric oligomeric compounds are chimeric oligonucleotides. In certain such embodiments, the chimeric oligonucleotides comprise differently modified nucleotides. In certain embodiments, chimeric oligonucleotides are mixed-backbone antisense oligonucleotides. In general, a chimeric oligomeric compound will have modified nucleosides that can be in isolated positions or grouped together in regions that will define a particular motif. Any combination of modifications and/or mimetic groups can comprise a chimeric oligomeric compound as described herein. In certain embodiments, chimeric oligomeric compounds typically comprise at least one region modified so as to confer increased resistance to nuclease degradation, increased cellular uptake, and/or increased binding affinity for the target nucleic acid. In certain embodiments, an additional region of the oligomeric compound may serve as a substrate for enzymes capable of cleaving RNA:DNA or RNA:RNA hybrids. By way of example, RNase H is a cellular endonuclease that cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

B. Design Considerations

The present invention contemplates the production of inhibitory double-stranded RNAs targeting CAG repeats of various disease-related genes and messages. In general, the RNAs will comprise a segment of about 7-30 bases that hybridizes to a CAG/CUG repeat, or to both a repeat and a portion of a region flanking a CAG/CUG repeat, defined as "a repeat junction." The length may be 7, 8, 9, 10, 11, 12, 13, 14, 15, 16, 17, 18, 19, 20, 21, 22, 23, 24, 25, 26, 27, 28, 29 or 30 bases in length.

Another design consideration is the placement of 1, 2, 3, 4 or 5 "mismatches" in the double-stranded RNA as compared to the target sequence. In one embodiment, the mismatches are generally "centrally located" in the RNA, i.e., not located within the first two or last two bases of the RNA. A more restrictive definition of centrally located would be the center 3-4 bases, or in the center base (for an odd number of bases) or one or both of the center bases (for an even number of bases). More particularly, on a nucleic acid of at least 15 residues in length, there should be at least 7 residues flanking each side of the mismatch base, or on a nucleic acid of at least 16 residues in length, there should be at least 7 residues flanking two adjacent mismatched bases. For each of the following molecules, the "central" bases are indicated in bold, or bold/underlined:

```
ATGCATG

ATGCATGC

ATGCATGCA

ATGCATGCAT                          (SEQ ID NO: 41)

ATGCATGCATG                         (SEQ ID NO: 42)

ATGCATGCATGC                        (SEQ ID NO: 43)

ATGCATGCATGCA                       (SEQ ID NO: 44)

ATGCATGCATGCAT                      (SEQ ID NO: 45)

ATGCATGCATGCATG                     (SEQ ID NO: 46)

ATGCATGCATGCATGC                    (SEQ ID NO: 47)

ATGCATGCATGCATGCA                   (SEQ ID NO: 48)

ATGCATGCATGCATGCAT                  (SEQ ID NO: 49)

ATGCATGCATGCATGCATG                 (SEQ ID NO: 50)

ATGCATGCATGCATGCATGC                (SEQ ID NO: 51)
```

Though any mismatch is useful, of particular interest are purine mismatches, such as introducing an adenosine base into the guide strand.

Another consideration is to avoid multiple changes in the "seed" sequence of the double-stranded RNA, i.e., the first 8 bases. Thus, in a double-stranded RNA of at least 19 bases, there would no or one mismatches in the first 8 bases, and 1-5 mismatches in bases 9-19, or in bases 9 to the 3'-terminus if the molecule is longer than 19 bases. In other words, with respect to multiple mismatches, these can be either in the guide strand, or in both strands, and only one mismatch should occur in the seed region.

In addition, to mismatches, it is contemplated that the guide strand may contain a base insertion with respect to the passenger strand.

III. TREATMENT OF REPEAT-ASSOCIATED DISEASES

The present invention also involves the treatment of polyglutamine neurodegenerative diseases, discussed above. By treatment, it is not necessary that all symptoms of the disease be addressed, or that any degree of "cure" be achieved. Rather, to accomplish a meaningful treatment, all that is required is that one or more symptoms of the disease be ameliorated to some degree, an advantageous effect be provided in combination with another therapy, or that the disease progression be slowed.

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals. One will generally desire to employ appropriate salts, buffers, and lipids to render delivery of the oligonucleotides to allow for uptake by target cells. Such methods an compositions are well known in the art, for example, as disclosed in U.S. Pat. Nos. 6,747,014 and 6,753,423. Compositions of the present invention comprise an effective amount of the oligonucleotide to cells, dissolved or dispersed in a pharmaceutically acceptable carrier or medium.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents, liposomes, cationic lipid formulations, microbubble nanoparticles, and the like. The use of such media and agents for pharmaceutically active substances is well-known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral or parenteral routes, including intracranial (including intraparenchymal and intraventricular), intrathecal, epidural, intravenous, intraarterial, intramuscular, intraperitoneal, subcutaneous, transdermal, airway (aerosol), nasal, rectal, vaginal and topical (including buccal and sublingual) administration. Compositions would normally be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, lipids, nanoparticles, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the NAAs of the present invention may be incorporated with excipients. The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intraarterial, intramuscular, subcutaneous, intraperitoneal, intrathecal, epidural and intracranial (including intraparenchymal and intraventricular) administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Lipid vehicles encompass micelles, microemulsions, macroemulsions, liposomes, and similar carriers. The term micelles refers to colloidal aggregates of amphipathic (surfactant) molecules that are formed at a well-defined concentration known as the critical micelle concentration. Micelles are oriented with the nonpolar portions at the interior and the polar portions at the exterior surface, exposed to water. The typical number of aggregated molecules in a micelle (aggregation number) is 50 to 100. Microemulsions are essentially swollen micelles, although not all micellar solutions can be swollen to form microemulsions. Microemulsions are thermodynamically stable, are formed spontaneously, and contain particles that are extremely small. Droplet diameters in microemulsions typically range from 10 100 nm. In contrast, the term macroemulsions refers to droplets with diameters greater than 100 nm. Liposomes are closed lipid vesicles comprising lipid bilayers that encircle aqueous interiors. Liposomes typically have diameters of 25 nm to 1 µm (see, e.g., Shah, 1998; Janoff, 1999).

In one embodiment of a liposome formulation, the principal lipid of the vehicle may be phosphatidylcholine. Other useful lipids include various natural (e.g., tissue derived L-α-phosphatidyl: egg yolk, heart, brain, liver, soybean) and/or synthetic (e.g., saturated and unsaturated 1,2-diacyl-SN-glycero-3-phosphocholines, 1-acyl-2-acyl-SN-glycero-3-phosphocholines, 1,2-diheptanoyl-SN-glycero-3-phosphocholine) derivatives of the same. Such lipids can be used alone, or in combination with a secondary lipid. Such secondary helper lipids may be non-ionic or uncharged at physiological pH, including non-ionic lipids such as cholesterol and DOPE (1,2-dioleolylglyceryl phosphatidylethanolamine). The molar ratio of a phospholipid to helper lipid can range from about 3:1 to about 1:1, from about 1.5:1 to about 1:1, and about 1:1.

Another specific lipid formulation comprises the SNALP formulation, containing the lipids 3-N-[(ω methoxypoly (ethylene glycol)$_{2000}$)carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar % ratio. See Zimmerman et al. (2006).

A liposome is, in simplest form, composed of two lipid layers. The lipid layer may be a monolayer, or may be multilamellar and include multiple layers. Constituents of the liposome may include, for example, phosphatidylcholine, cholesterol, phosphatidylethanolamine, etc. Phosphatidic acid, which imparts an electric charge, may also be added. Exemplary amounts of these constituents used for the production of the liposome include, for instance, 0.3 to 1 mol, 0.4 to 0.6 mol of cholesterol; 0.01 to 0.2 mol, 0.02 to 0.1 mol of phosphatidylethanolamine; 0.0 to 0.4 mol, or 0-0.15 mol of phosphatidic acid per 1 mol of phosphatidylcholine.

Liposomes can be constructed by well-known techniques (see, e.g., Gregoriadis (1993). Lipids are typically dissolved in chloroform and spread in a thin film over the surface of a tube or flask by rotary evaporation. If liposomes comprised of a mixture of lipids are desired, the individual components are mixed in the original chloroform solution. After the organic solvent has been eliminated, a phase consisting of water optionally containing buffer and/or electrolyte is added and the vessel agitated to suspend the lipid. Optionally, the suspension is then subjected to ultrasound, either in an ultrasonic bath or with a probe sonicator, until the particles are reduced in size and the suspension is of the desired clarity. For transfection, the aqueous phase is typically distilled water and the suspension is sonicated until nearly clear, which requires several minutes depending upon conditions, kind, and quality of the sonicator. Commonly, lipid concentrations are 1 mg/ml of aqueous phase, but could be higher or lower by about a factor of ten.

Lipids, from which the solvents have been removed, can be emulsified by the use of a homogenizer, lyophilized, and melted to obtain multilamellar liposomes. Alternatively, unilamellar liposomes can be produced by the reverse phase evaporation method (Szoka and Papahadjopoulos, 1978). Unilamellar vesicles can also be prepared by sonication or extrusion. Sonication is generally performed with a bath-type sonifier, such as a Branson tip sonifier (G. Heinemann Ultrashall and Labortechnik, Schwabisch Gmund, Germany) at a controlled temperature as determined by the melting point of the lipid. Extrusion may be carried out by biomembrane extruders, such as the Lipex Biomembrane Extruder (Northern Lipids Inc, Vancouver, British Columbia, Canada). Defined pore size in the extrusion filters may generate unilamellar liposomal vesicles of specific sizes. The liposomes can also be formed by extrusion through an asymmetric ceramic filter, such as a Ceraflow Microfilter (commercially available from the Norton Company, Worcester, Mass.).

Following liposome preparation, the liposomes that have not been sized during formation may be sized by extrusion to achieve a desired size range and relatively narrow distribution of liposome sizes. A size range of about 0.2-0.4 microns will allow the liposome suspension to be sterilized by filtration through a conventional filter (e.g., a 0.22 micron filter). The filter sterilization method can be carried out on a high throughput basis.

Several techniques are available for sizing liposomes to a desired size, including, ultrasonication, high-speed homogenization, and pressure filtration (Hope et al., 1985; U.S. Pat. Nos. 4,529,561 and 4,737,323). Sonicating a liposome suspension either by bath or probe sonication produces a progressive size reduction down to small unilamellar vesicles less than about 0.05 microns in size. Multilamellar vesicles can be recirculated through a standard emulsion homogenizer until selected liposome sizes, typically between about 0.1 and 0.5 microns. The size of the liposomal vesicles may be determined by quasi-elastic light scattering (QELS) (see Bloomfield, 1981). Average liposome diameter may be reduced by sonication of formed liposomes. Intermittent sonication cycles may be alternated with QELS assessment to guide efficient liposome synthesis.

Liposomes can be extruded through a small-pore polycarbonate membrane or an asymmetric ceramic membrane to yield a well-defined size distribution. Typically, a suspension is cycled through the membrane one or more times until the desired liposome size distribution is achieved. The liposomes may be extruded through successively smaller-pore membranes, to achieve a gradual reduction in liposome size. For use in the present invention, liposomes have a size of about 0.05 microns to about 0.5 microns, or having a size of about 0.05 to about 0.2 microns.

It is common in many fields of medicine to treat a disease with multiple therapeutic modalities, often called "combination therapies." Therapies would be provided in a combined amount effective to achieve a reduction in one or more disease parameter. This process may involve contacting subjects with the both agents/therapies at the same time, e.g., using a single composition or pharmacological formulation that includes both agents, or by contacting the subject with two distinct compositions or formulations, at the same time, wherein one composition includes the double-stranded RNAs of the present invention and the other includes the other agent.

Alternatively, the double-stranded RNA therapy may precede or follow the other treatment by intervals ranging from minutes to weeks. One would generally ensure that a significant period of time did not expire between the time of each delivery, such that the therapies would still be able to exert an advantageously combined effect on the subject. In such instances, it is contemplated that one would contact the subject with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the double-stranded RNA therapy or the other therapy will be desired. Various combinations may be employed, where the double-stranded RNA is "A," and the other therapy is "B," as exemplified below:

A/B/A  B/A/B  B/B/A  A/A/B  B/A/A  A/B/B  B/B/B/A  B/B/A/B

A/A/B/B  A/B/A/B  A/B/B/A  B/B/A/A  B/A/B/A  B/A/A/B

B/B/B/A  A/A/A/B  B/A/A/A  A/B/A/A  A/A/B/A  A/B/B/B

B/A/B/B  B/B/A/B

Other combinations are contemplated. Agents or factors suitable for use in a combined therapy include those described above for the various polyglutamine repeat diseases.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating polyglutamine diseases.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods siRNAs and PNAs.

siRNAs were purchased from Integrated DNA Technologies (IDT, Coralville, Iowa). Chemically-modified siRNAs were provided by Alnylam Pharmaceuticals. The melting temperature for the siRNAs was measured in a Cary 100 Bio UV-Visible Spectrophotometer. Absorbance was monitored at 260 nm a 1 cm quartz cuvette. siRNA (2 µM) in 0.1 M phosphate buffer (pH 704) was annealed and denatured 7 times from 4° C. to 95° C. at a ramp rate of 1° C./min. PNA-peptide conjugates were synthesized on an Expedite 8909 synthesizer (Applied Biosystems, Foster City, Calif.) and purified by C-18 reversed phase HPLC. Peptoid residue was manually synthesized first on the resins according to the published protocol (Hernando et al., 2002). The resins were loaded on the machine to continue synthesize the PNA conjugate.

Cell Culture and Transfection.

Patient-derived fibroblast cell lines GM04281, G04719, GM04717 were obtained from the Coriell Institute (Camden, N.J.). Cells were maintained at 37° C. and 5% $CO_2$ in Minimal Essential Media Eagle (MEM) (Sigma, M4655) supplemented with 10% heat inactivated fetal bovine serum (Sigma) and 0.5% MEM nonessential amino acids (Sigma). Cells were plated in 6-well plates at 60,000 cells/well in supplemented MEM two days prior to transfection. siRNAs were transfected to cells using RNAiMAX (Invitrogen) according to the manufacturer's instructions. The appropriate amount of the lipid (3 µL for 100 nM oligonucleotides) were added to OptiMEM containing siRNAs, and the mixture (250 µL total) were incubated for 20 min in dark. OptiMEM was added to the mixture to a final volume of 1.25 mL and then added to cells. The siRNA-containing media were exchanged 24 h later with fresh supplemented MEM. Cells were typically harvested 4 days after transfection for protein assay.

Analysis of HTT Expression.

Cells were harvested with trypsin-EDTA solution (Invitrogen) and lysed. The protein concentration in each sample was quantified with BCA assay (Thermo Scientific, Waltham, Mass.). SDS-PAGE (separating gel: 5% acrylamide-bisacrylamide/34.7:1, 450 mM Tris-acetate pH 8.8; stacking gel: 4% acrylamide-bisacrylamide/34.7:1, 150 mM Tris-acetate pH 6.8) (XT Tricine Running Buffer, Bio-Rad, Hercules, Calif.) was used to separate wild-type and mutant HTT proteins. Gels were run at 70V for 15 min followed by 100V for 4-5 h. For separation of HTT variants containing shorter CAG repeats, gels were run at 70 V for 15 min, then 110 V for 6 h. The electrophoresis apparatus was placed in ice-water bath to prevent overheating of the running buffer. Actin protein expression was monitored to ensure even loading on protein in each lane. In parallel with analysis for HTT expression, portions of each protein lysate sample were analyzed for β-actin expression by SDS-PAGE (7.5% acrylamide pre-cast gels; Bio-Rad). These gels were run at 70V for 15 min followed by 100V for 1 h. After gel electrophoresis, proteins were transferred to membrane (Hybond-C Extra; GE Healthcare Bio-Sciences, Piscataway, N.J.). Primary antibodies specific for each protein were obtained and used at the indicated dilution ratio: anti-HTT antibody (MAB2166. 1:10000; Chemicon), anti-β-actin antibody (1:10,000; Sigma).

HRP conjugate anti-mouse or anti-rabbit secondary antibody (1:10000 and 1:5000, respectively; Jackson ImmunoResearch Laboratories, West Grove Pa.) was used for visualizing proteins using SuperSignal West Pico Chemiluminescent Substrate (Thermo Scientific). Protein bands were quantified using ImageJ software (Rasband, W. S., ImageJ, U.S. National Institutes of Health, Bethesda, Md., USA, rsb.info.nih.gov/ij/, 1997-2007). The percentage of inhibition was calculated as a relative value to a control or no treatment sample. For dose-response experiments, the $IC_{50}$ value was generated with GraphPad Prism program. Each data plot was fit into the following model equation, $y = 100(1-x^m/(n^m+x^m))$, where y is percent inhibition of protein and x is concentration of siRNAs, m and n are fitting parameters, where n is taken as the $IC_{50}$ value. Usually three independent experiments data were averaged and the error bar was calculated using standard deviation from the mean.

Analysis of Ataxin-3 Expression.

Cells were harvested with trypsin-EDTA solution (Invitrogen). The protein concentration was quantified with BCA assay (Thermo Scientific, Waltham, Mass.). SDS-PAGE (7.5% acrylamide pre-cast gels; Bio-Rad) was used to separate the mutant and wild-type ataxin-3 protein. Primary antibodies for ataxin-3 (MAB5360; 1:10000; Chemicon), anti-β-actin antibody (1:10000; Sigma), HRP conjugate anti-mouse secondary antibody (1:10000; Jackson ImmunoResearch Laboratories, West Grove Pa.) were used for visualizing proteins by SuperSignal West Pico Chemiluminescent Substrate (Thermo Scientific). Protein bands were quantified using ImageJ (Rasband, W. S., ImageJ, U. S. National Institutes of Health, Bethesda, Md., USA, rsb.info.nih.gov/ij/, 1997-2007). The percentage of inhibition was calculated as a relative value to a control sample. The GraphPad Prism 4 program was used to generate the fitting curves for inhibition of ataxin-3. The following equation was used for fitting, $y=100(1-x^m/(n^m+x^m))$, where y is percentage of inhibition and x is the oligomer concentration, m and n are fitting parameters, where n is taken as the $IC_{50}$ value. The error of $IC_{50}$ is standard deviation, which is calculated from each individual dose curve.

Total RNA was extracted using TRIzol (Invitrogen) 3 days after transfection. After DNase I treatment, reverse transcription reactions were done using High Capacity Reverse Transcription Kit (Applied Biosystems) according to the manufacturer's protocol. Quantitative PCR was performed on a 7500 real-time PCR system (Applied Biosystems) using iTaq SYBR Green Supermix (Bio-rad). Data was normalized relative to levels of 18S mRNA. Primer sequences specific for ataxin-3 are as follows:

```
forward primer,
                                  (SEQ ID NO: 110)
5'-GGAAATATGGATGACAGTGG-3';

reverse primer,
                                  (SEQ ID NO: 111)
5'-ATCCTGAGCCTCTGATACTC-3'.
```

Primers specific for 18S were obtained from Applied Biosystems.

Example 2

Results

Design of Mismatch-Containing RNAs.

The inventors have previously shown that RNA duplexes that are fully complementary to CAG repeats show little selectivity for inhibiting expression of the mutant form of huntingtin (HTT) relative to the wild-type form. They hypothesized that introducing mismatched bases into RNA duplexes might alter recognition of HTT mRNA and increase selectivity. To test this hypothesis, they synthesized several different RNAs with mismatched bases relative to the CAG repeat in different positions (FIG. 1). The mismatches were designed to test alterations from position 4 (RNA P4) to position 16 (RNA P16) relative to the 5' terminus of the antisense strand of the duplex RNA.

Allele-Selective Inhibition by Mismatch-Containing RNAs.

Duplex RNAs were transfected into GM04281 cells using cationic lipid. GM04281 is a patient-derived fibroblast cell line with a mutant allele containing 69 CAG repeats and a wild-type allele with 17 repeats. The inventors observed that several mismatch-containing RNA duplexes exhibited striking selectivity (FIGS. 2A-K, FIG. 4). For example, RNAs P8, P9, P10R, P10, P11 all had selectivities of 19-fold or higher (selectivities are calculated by dividing the $IC_{50}$ value for inhibition of wild-type HTT expression by the $IC_{50}$ value for inhibition of mutant HTT expression. These highly selective RNAs also possessed good potencies for inhibition of HTT expression, with $IC_{50}$ values under 10 nM.

The inventors also tested three duplex RNAs with multiple mismatches (FIGS. 3A-C). P910 with two mismatches in the central region at positions 9 and 10 exhibited good potency (4.5 nM) and excellent selectivity (>22 fold). Duplex RNAs with 3 (RM3) or 4 (RM4) mismatches showed greatly decreased potencies. RM3 and RM4 have mismatches within the critical "seed sequence" (bases 2-8) necessary for efficient RNA, so the reduced potencies are not surprising. miRNAs with multiple mismatches outside the seed sequence can be effective inhibitors of gene expression, and thus CAG-targeted duplex RNAs with more than two mismatches outside the seed might also be good candidates for potent and allele-selective inhibition.

Effect of Mismatch Containing Bases on the Guide Strand.

Duplex RNAs consist of a guide strand and a passenger strand. The guide strand is complementary to the target mRNA and should be more sensitive to the introduction of mutations. To test this possibility, the inventors tested duplex RNAs with one or two mutations on the guide strand and passenger strand containing an unbroken CAG repeat (FIGS. 5A-E). All of these duplexes showed greater than 9-fold selectivity and potencies of 1.3 to 10.4 nM. These data demonstrate that allele-selective inhibition can be achieved by introducing mutations in the guide strand while leaving the passenger strand unchanged.

Effect of Changing the Register of CAG Recognition.

An RNA duplex complementary to a CAG repeat can begin with either G, U, or C. All the duplexes tested above began with G. The inventors tested whether beginning with U or C and changing the register of mRNA recognition would affect potency or selectivity (FIGS. 6A-D).

The inventors observed that duplexes REPC or REPU that were fully complementary to the CAG repeat showed little selectivity (1.75- to 2.3-fold). Duplex RNAs that contained one mismatch and begin with C (REPC-b) or U (REPU-b) each showed greater that 13-fold selectivity and potencies of under 10 nM. These data demonstrate that allele-selective inhibition can be achieved regardless of the register of recognition of the CAG repeat within HTT mRNA.

Effect of Mismatch-Containing Duplexes in Cell Lines with Fewer Repeats.

Most Huntington's Disease (HD) patients have 45 or fewer repeats in their mutant alleles. To determine whether the present strategy for allele-selective inhibition might succeed with a broad range of HD patients the inventors tested mismatch-containing duplex RNAs in GM04719 (44 repeats) (FIGS. 7A-B) and GM04717 (41 repeats) cells. The inventors observed good selectivities (greater than 11-fold) and good potencies (less than 10 nM) in both cell lines. By contrast, a fully complementary duplex exhibited no selectivity in GM04717 cells (FIG. 8A).

Effect of Chemical Modifications of Allele-Selective Inhibition.

Therapeutic application of duplex RNAs may require that the duplexes be chemically-modified to improve their properties in vivo. To determine whether chemical modification would be compatible with allele-selective inhibition, the inventors tested several chemically-modified duplex RNAs (FIG. 9). The modified strands contained 0-8 2'-O-methyl bases. One phosphorothioate (PS) linkage was included between the terminal thymidines. An initial screen at 25 and 50 nM demonstrated that all of the modified duplexes were active and allele selective inhibitors of mutant HTT expression (FIG. 10). Analysis over a broader range of concentrations revealed that all modified duplexes were potent and selective inhibitors of HTT expression, with $IC_{50}$ values 2.8 to 9.8 nM and selectivities ranging from 14- to greater than 45-fold (FIGS. 11A-G).

Additional Data on Inhibition of HTT Expression in Cell Lines with 44 or 41 Mutant Repeats.

Figure 13:
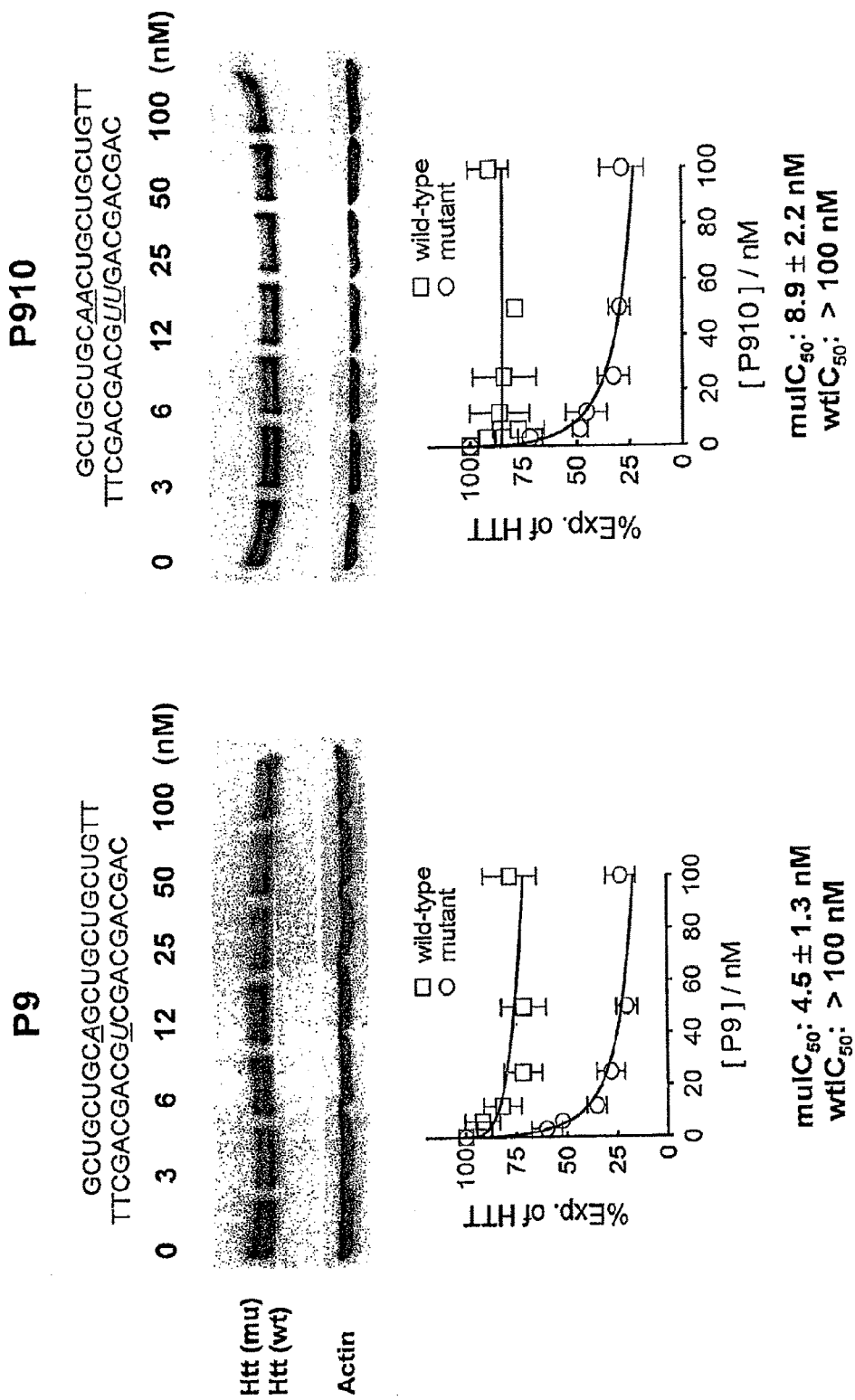
FIG. 13. Effects of siRNA targeting CAG repeat on HTT expression in GM04719 fibroblasts with shorter repeats (CAG 44/15). Left hand panel is siRNA P9; right hand panel is siRNA P910. Mismatched bases relative to the CAG repeat with HTT mRNA target are shown italicized and underlined. (SEQ ID NOS: 3, 4, 11, 12)
Figure 14:
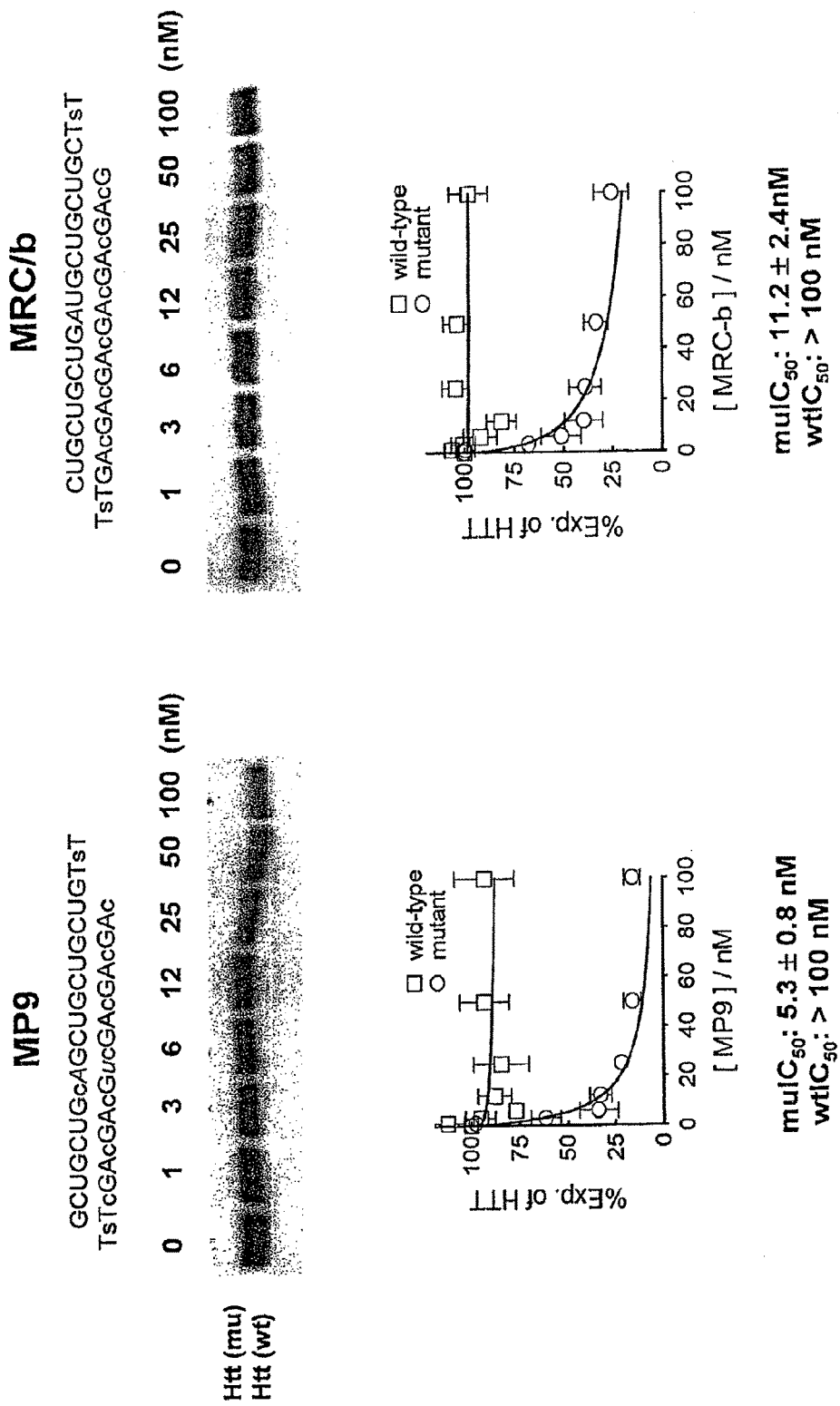
FIG. 14. Chemically-modified siRNA effects on HTT expression in GM04719 fibroblasts with shorter repeats (CAG 44/15). Left hand panel is siRNA MP9; right hand panel is siRNA MRC/b. Lower case=2'-O-methyl RNA base. Mismatched bases relative to the CAG repeat with HTT mRNA target are shown italicized. s=phosphorothioate linkage between the bases. (SEQ ID NOS: 27, 28, 37, 38)
Figure 15:
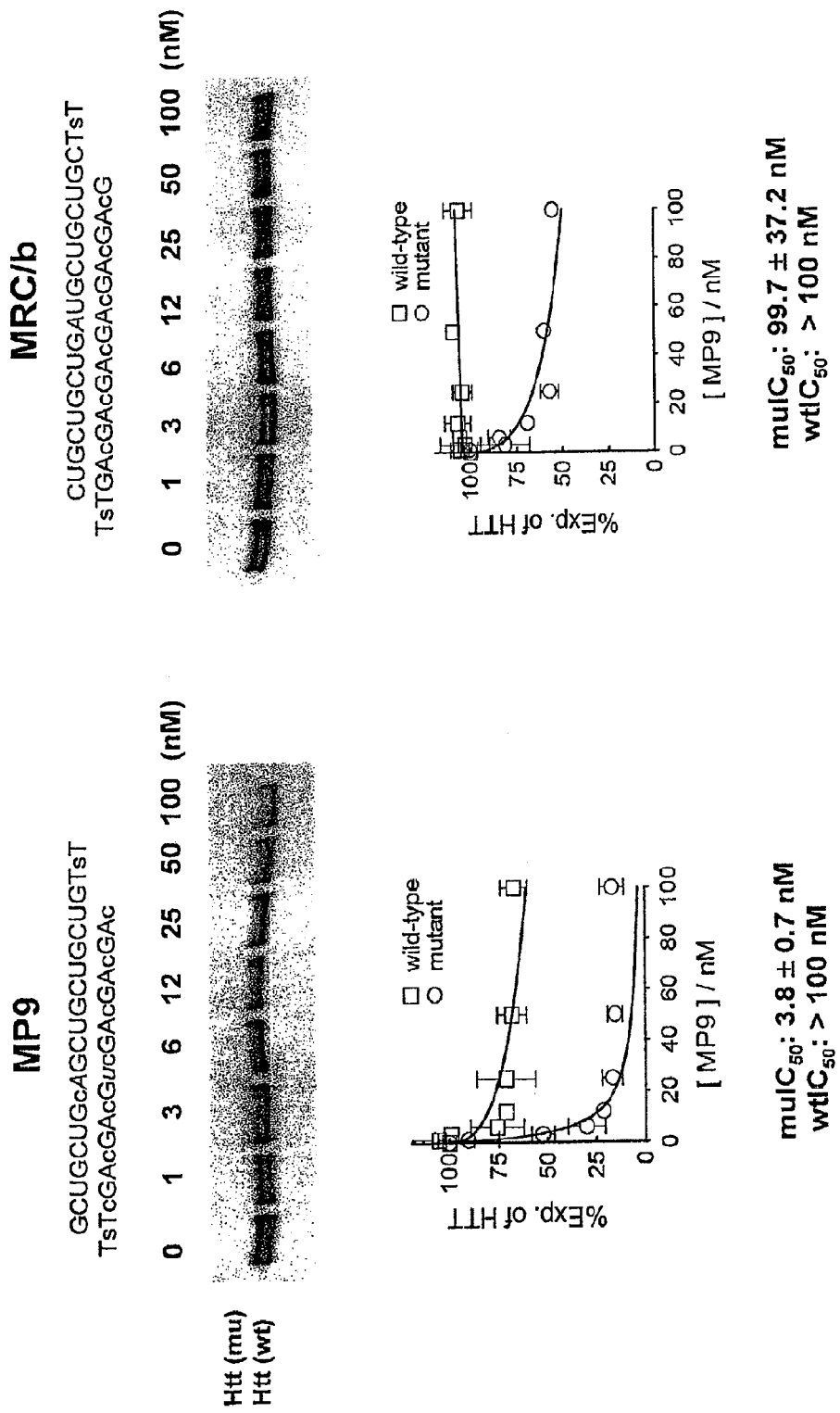
FIG. 15. Chemically-modified siRNA effects on Htt expression in GM04717 (CAG 41/20) fibroblasts. Left hand panel is siRNA MP9; right hand panel is siRNA MRC/b. Lower case=2'-O-methyl RNA base. Mismatched bases relative to the CAG repeat with HTT mRNA target are shown italicized. s=phosphorothioate linkage between the bases. (SEQ ID NOS: 27, 28, 37, 38)
Figure 16:
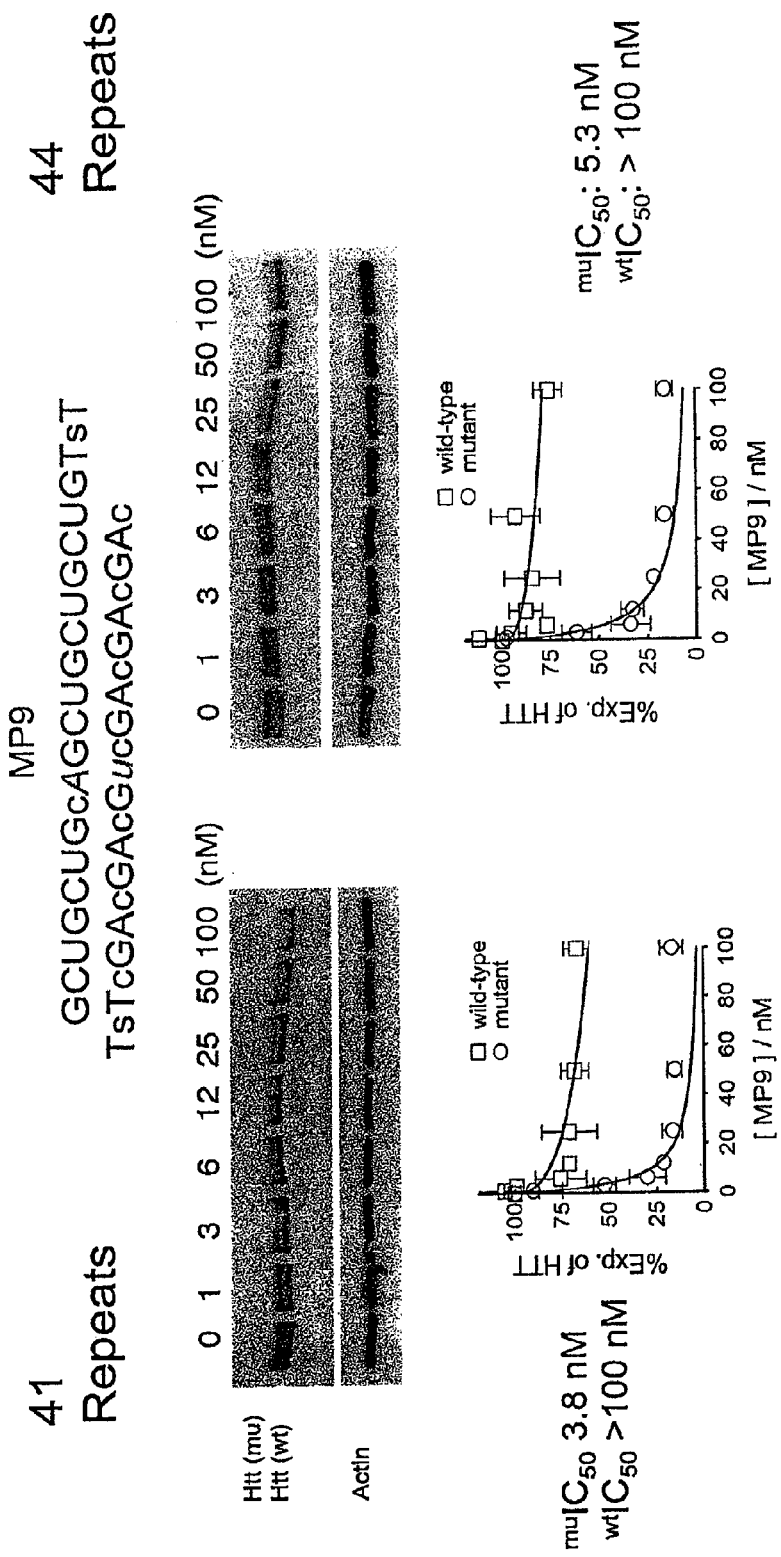
FIG. 16. Chemically-modified siRNA are selective in cell lines with shorter CAG repeats (41/44). Left hand panel is treatment of a 41 repeat cell line (GM04717) with siRNA MP9; right hand panel is treatment of a 44 repeat cell (GM04719) line with siRNA MP9. Lower case=2'-O-methyl RNA base. Mismatched bases relative to the CAG repeat with HTT mRNA target are shown italicized. s=phosphorothioate linkage between the bases. (SEQ ID NOS: 27, 28)

To further investigate inhibition of HTT expression in cell lines with relatively few mutant repeats, the inventors tested mismatch-containing duplexes (either with or without chemical modifications) in cell lines GM04719 (44 mutant/15 wild-type repeats) or GM04717 (41 mutant/15 wild-type repeats). They observed that fully complementary duplex RNA REP exhibited less than two-fold selectivity in GM04719 cells (FIG. 12, left panel). Mismatch containing RNA RC/b showed a reduced potency of 61 nM and >1.6-fold selectivity (FIG. 12, right panel). Mismatch containing duplexes P9 and P910 showed more striking results, with good potencies (4.1 and 8.9 nM respectively) and good selectivities (>11-fold) in GM04719 cells (FIG. 13). Chemically-modified RNAs MP9 and MRC/b also yielded promising results, with potencies of 5.3 and 11.2 nM respectively and selectivities of 10-20 fold (FIG. 14). Similar experiments in GM04717 cells yielded good potency and selectivity using chemically modified RNA MP9 (3.8 nM, >25-fold), but reduced potency with MRC/b (FIG. 15). Experiments in cells with 44 repeats (GM04719) also yielded allele-selective inhibition (FIG. 16).

Introducing Additional Mutations in the Central Region.

Figure 17:
FIG. 17. Three Central Mismatches are Tolerated. Mismatched bases relative to the CAG repeat with HTT mRNA target are shown italicized and underlined. The experiment was performed in GM04281 cells (69/17 repeats) (SEQ ID NOS: 106, 107)
Figure 18:
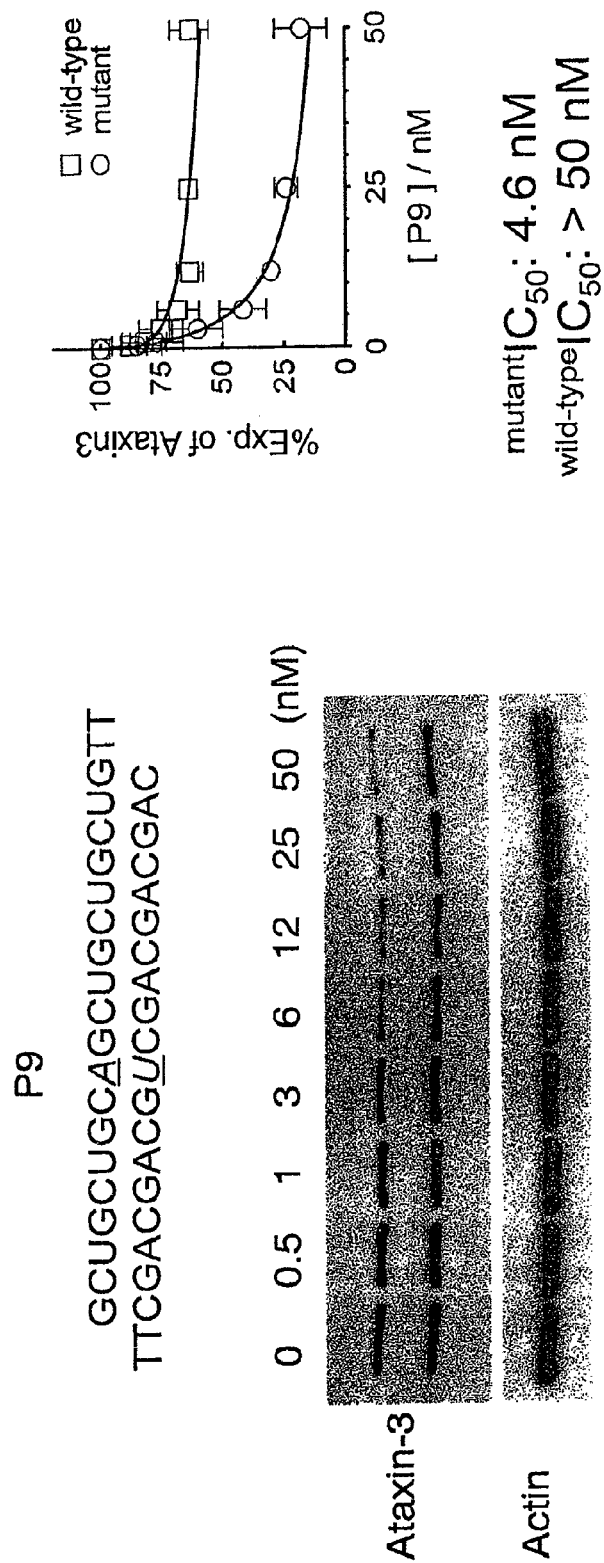
FIG. 18. Inhibition Ataxin-3 (GM06151, CAG72/24). Treatment of cell line GM06151 with siRNA P9. Mismatched bases relative to the CAG repeat with Ataxin-3 mRNA target are shown italicized and underlined. (SEQ ID NOS: 3, 4)

These results suggested that mutations in the central region of the RNA duplex would yield the best allele-selectivities. The inventors chose, therefore, to introduce additional mutations and observed that a duplex with three central mismatches showed excellent selectivity (FIG. 17). This result is significant because it suggests that several mismatches can be tolerated, increasing the pool of duplex RNA sequences that can be tested for optimal properties in vivo.

Selective Inhibition of Ataxin-3.

The inventors examined whether mismatch-containing duplex RNAs can inhibit a second triplet repeat gene, Ataxin-3. Experiments were done in GM06151 cells with 74 mutant repeats, towards the middle of the patient range. They observed allele-selective inhibition (FIG. 18, FIGS. 19A-D, FIGS. 20A-C). These data demonstrate that our strategy can succeed with triplet-repeat containing genes other than HTT.

Further Data and Data Summaries for Experiments in Cell Lines with 44 or 41 Repeats.

Fully complementary RNA REP shows little selectivity in cell line GM04719 containing 44 mutant repeats (FIG. 21A). By contrast, several mismatch-containing RNA duplexes show good allele selectivities (FIGS. 21B-D, FIGS. 22A-C, summarized in FIG. 22D). RNA REP also showed little or no selectivity in cell line GM04717 containing 41 CAG repeats in the mutant allele (FIG. 23A). Mismatch containing RNAs again showed good selectivities (FIGS. 23B-D, FIGS. 24A-C, summarized in FIG. 24D). These data further demonstrate that mismatch-containing RNAs can achieved allele-selective inhibition of HTT in a variety of human cell lines representing CAG repeat numbers found in most of the human patient population.

Effects on HTT Expression of Duplex RNAs with Mismatched Bases at Different Positions.

Figure 25:
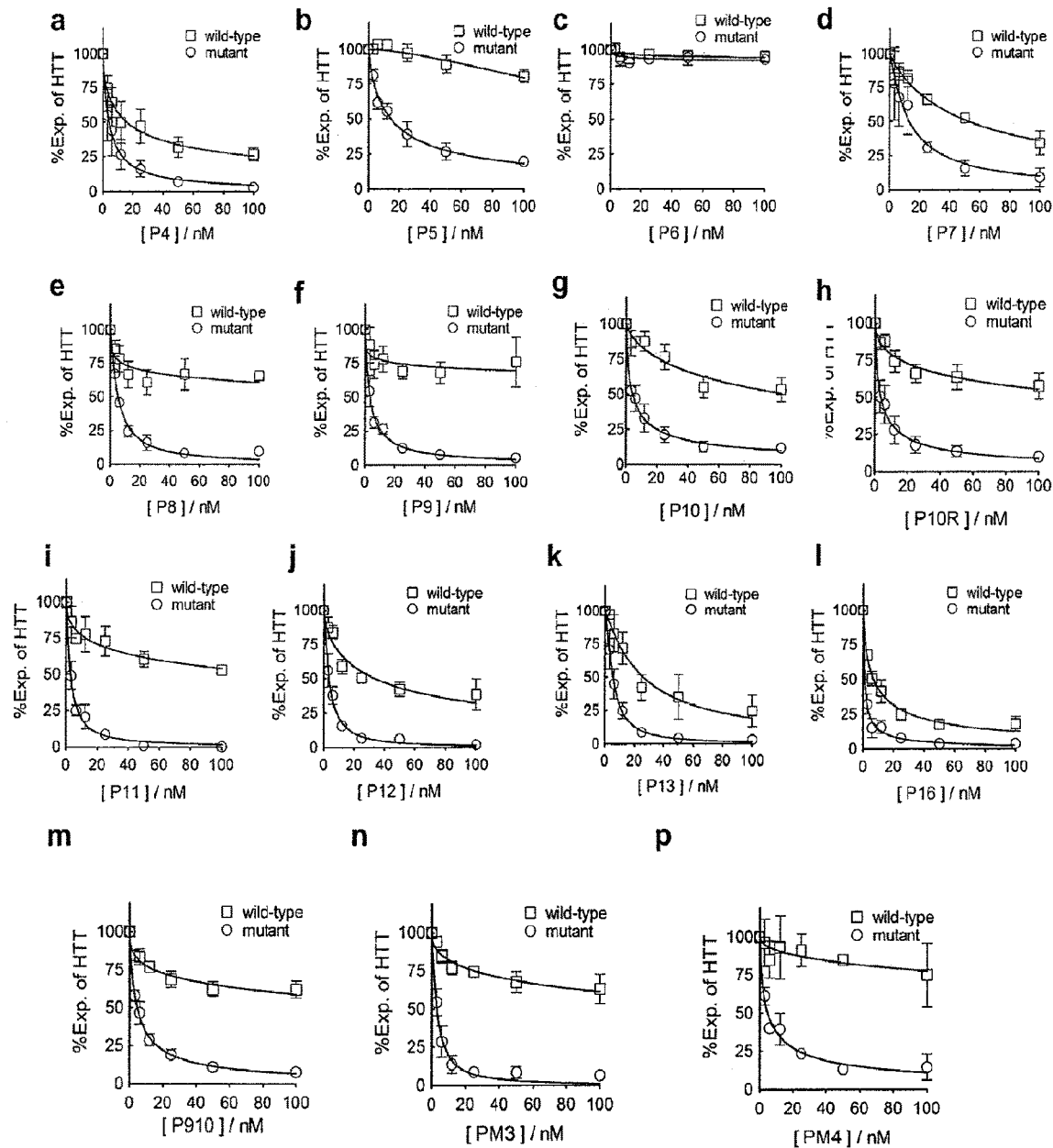
FIGS. 25A-P. Effects on HTT expression of duplex RNAs with mismatched bases at different positions Inhibition of HTT expression by siRNAs (FIG. 25A) P4, (FIG. 25B) P5, (FIG. 25C) P6, (FIG. 25D) P7, (FIG. 25E) P8, (FIG. 25F) P9, (FIG. 25G) P10, (FIG. 25H) P10R, (FIG. 25I) P11, (FIG. 25J) P12, (FIG. 25K) P13 (FIG. 25L) P16, (FIG. 25M) P910, (FIG. 25N) PM3, and (FIG. 25P) PM4. The dose curves are averaged data from at least three independent experiments. siRNAs were tested in HD patient fibroblasts (GM04281, mutant allele/69 CAG, wild type/17 CAG repeats).

The inventors determined $IC_{50}$ values to characterize the potency of inhibition of HTT expression by various mismatch-containing duplexes (FIGS. 25A-P). Values were determined from at least three independent experiments. With the exception of duplex P6, all duplexes inhibited HTT expression.

Effect of Multiple Mismatched Bases.

Figure 27:
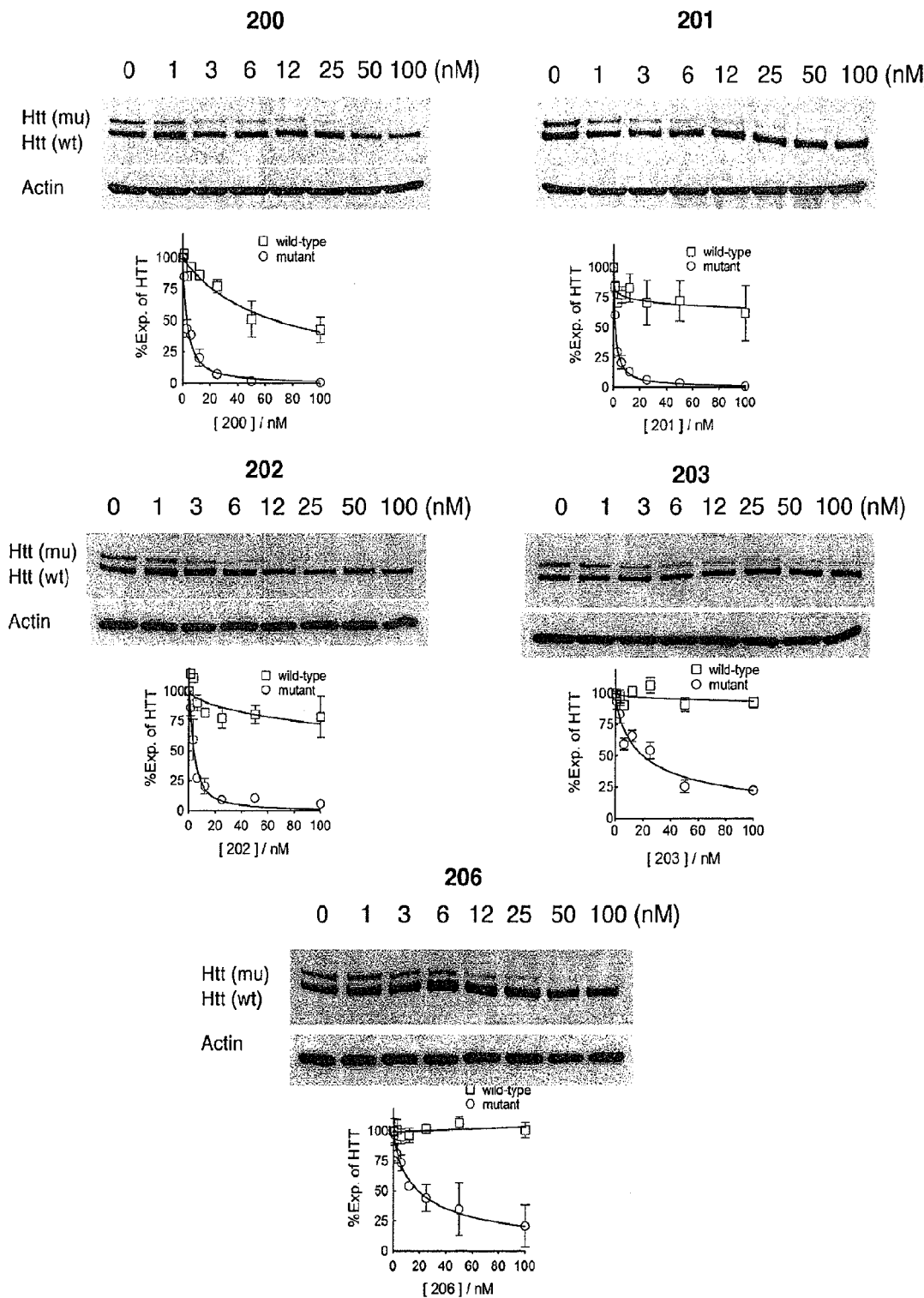
FIG. 27. Dose curves of chemically-modified siRNAs on Htt expression. (GM04281, CAG 69/17) Representative western blot images are presented. The figures below are averaged data from three independent experiments.
Figure 27:
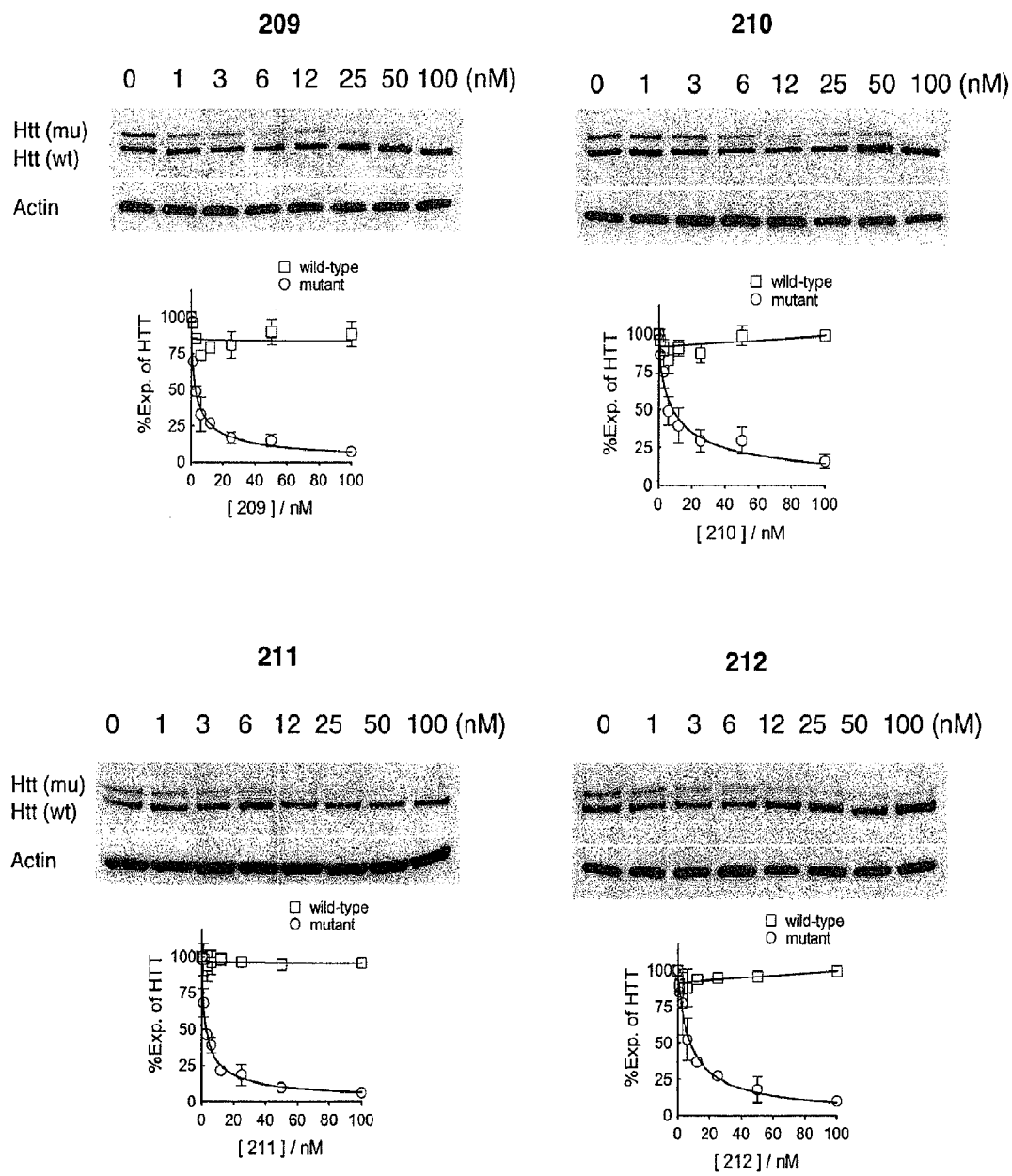

Additional mismatch-containing RNAs were designed and tested (FIG. 26A-B). These RNAs were chosen to have multiple mismatches relative to the CAG target and minimal complementarity to other sequences within the genome. Duplexes had chemical modifications that improve in vivo properties. These duplexes were potent and selective inhibitors of HTT expression (FIGS. 26A-B and 27).

Effect of Introducing Abasic Sites on Inhibition of HTT Expression.

Figure 29:
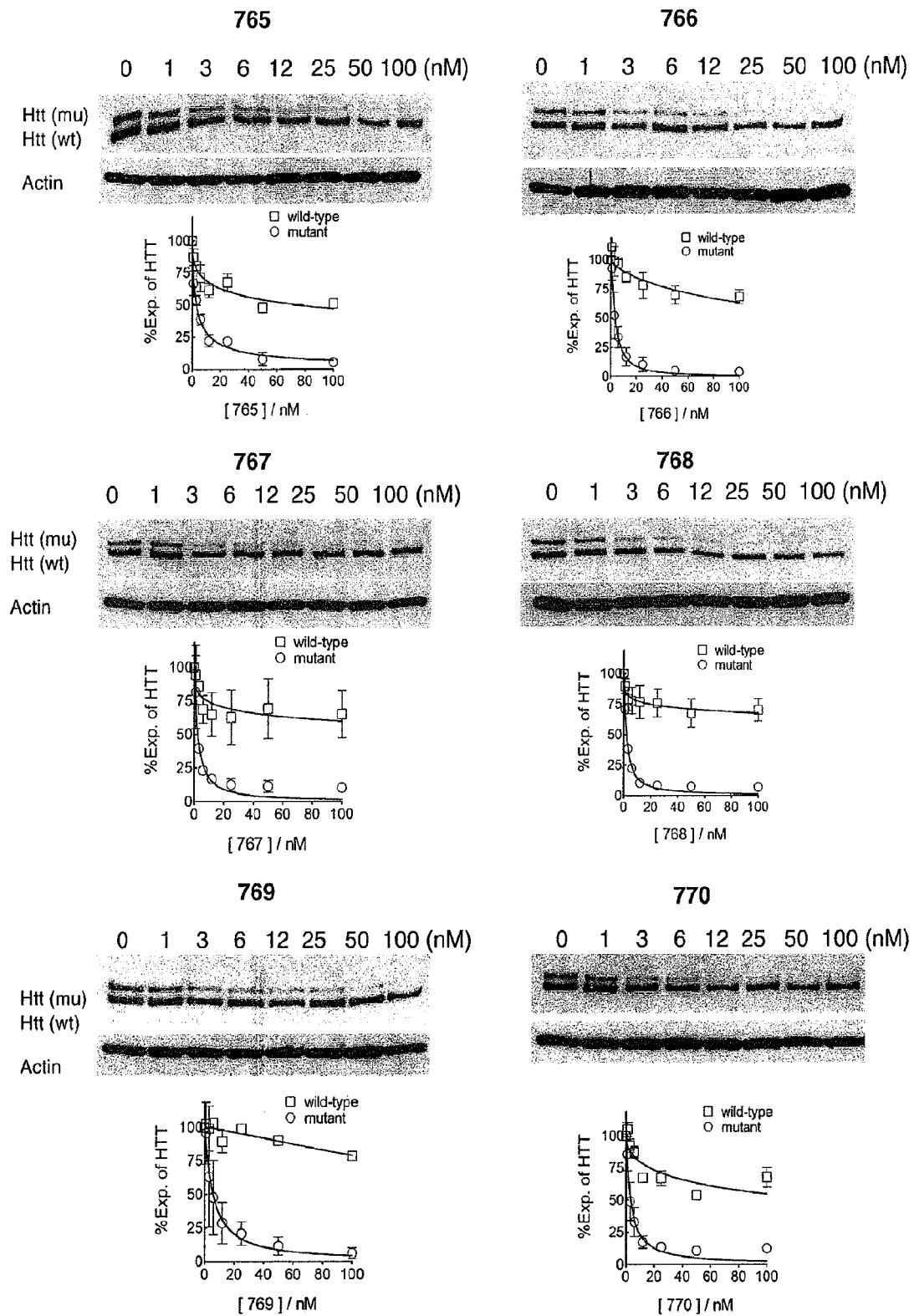
FIG. 29. Dose curves of chemically modified siRNAs with abasic bases on Htt expression. (GM04281, CAG 69/17) Representative western blot images are presented. The figures below are averaged data from three independent experiments.

The introduction of abasic sites allows us to ask whether mismatches are necessary to achieve selectivity. Abasic monomers were introduced at various sites within the anti-CAG duplex (Table 2). The resulting duplexes were potent and selective inhibitors of HTT expression (FIGS. 28A-B and 29).

Effect of Mismatch-Containing RNAs on Levels of HTT mRNA.

The inventors used qPCR to evaluate levels of HTT mRNA. They observed that addition of mismatch-containing duplex RNAs had little effect on HTT mRNA (FIGS. 30A-B). Duplex RNAs that are fully complementary sequences outside of HTT CAG-repeat mRNA reduce HTT mRNA, as ould be expected from the standard mechanism of RNAi by fully complementary duplexes.

siRNAs Inhibit Gene Expression in Striatal Progenitor Cells.

Figure 31:
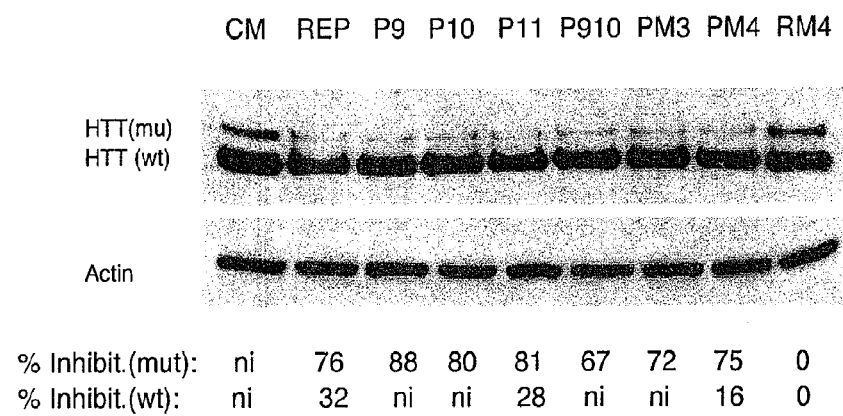
FIG. 31. siRNAs with mismatched bases selectively inhibit mutant HTT in striatal neuron progenitor cells CH00096 (CAG 111/7). siRNAs were tested in 50 nM concentrations.

Striatal cells are heavily affected in HD patients. To test whether selective inhibition could also be achieved in striatal cells, the inventors tested inhibition in CH00096 cells (111 repeats in the mutant allele). Efficient inhibition was achieved by several different mismatch-containing duplex RNAs (FIG. 31).

Experimental Design.

Experiments employed patient-derived fibroblast cell line GM06151 that is heterozygous for mutant ATX3. The wild-type allele contains 24 repeats and a mutant allele has 74 repeats. The 74 repeats within the mutant allele are typical of the repeat number found in SCA3 patients (Sasaki et al., 1995) and GM06151 cells offer a good test for the applicability of the approach to most patients. Cationic peptides were used to efficiently deliver PNAs into cells and several different peptide or peptoid conjugates were tested. Single-stranded bridged nucleic acid (BNA) oligonucleotides were introduced using PepMute, a peptide-based transfection reagent. Duplex RNAs were transfected into cells using cationic lipid using standard protocols (Janowski et al., 2006).

Allele-Selective Inhibition by Duplex RNAs.

Double-stranded RNA provides an alternate approach to gene silencing. The inventors had previously shown that duplex RNAs that were fully complementary to the CAG repeat tract were potent but non-selective inhibitors of ATX3 expression (Hu et al., 2009). Double-stranded RNA, however, can silence gene expression through two distinct mechanisms (Filipowicz et al., 2008; Kurreck et al., 2009). When duplex RNA is fully complementary to its mRNA target it is likely that the mRNA will be cleaved by the protein Argonaute 2 (AGO2) (Liu et al., 2004). However, if the RNA is imperfectly complementary, interactions at the AGO2 active site are disrupted (Du et al., 2005; Wang et al., 2008) and cleavage of the RNA is less likely and reduced levels of protein will be due to inhibition of translation or increased degradation of mRNA.

Figure 32:
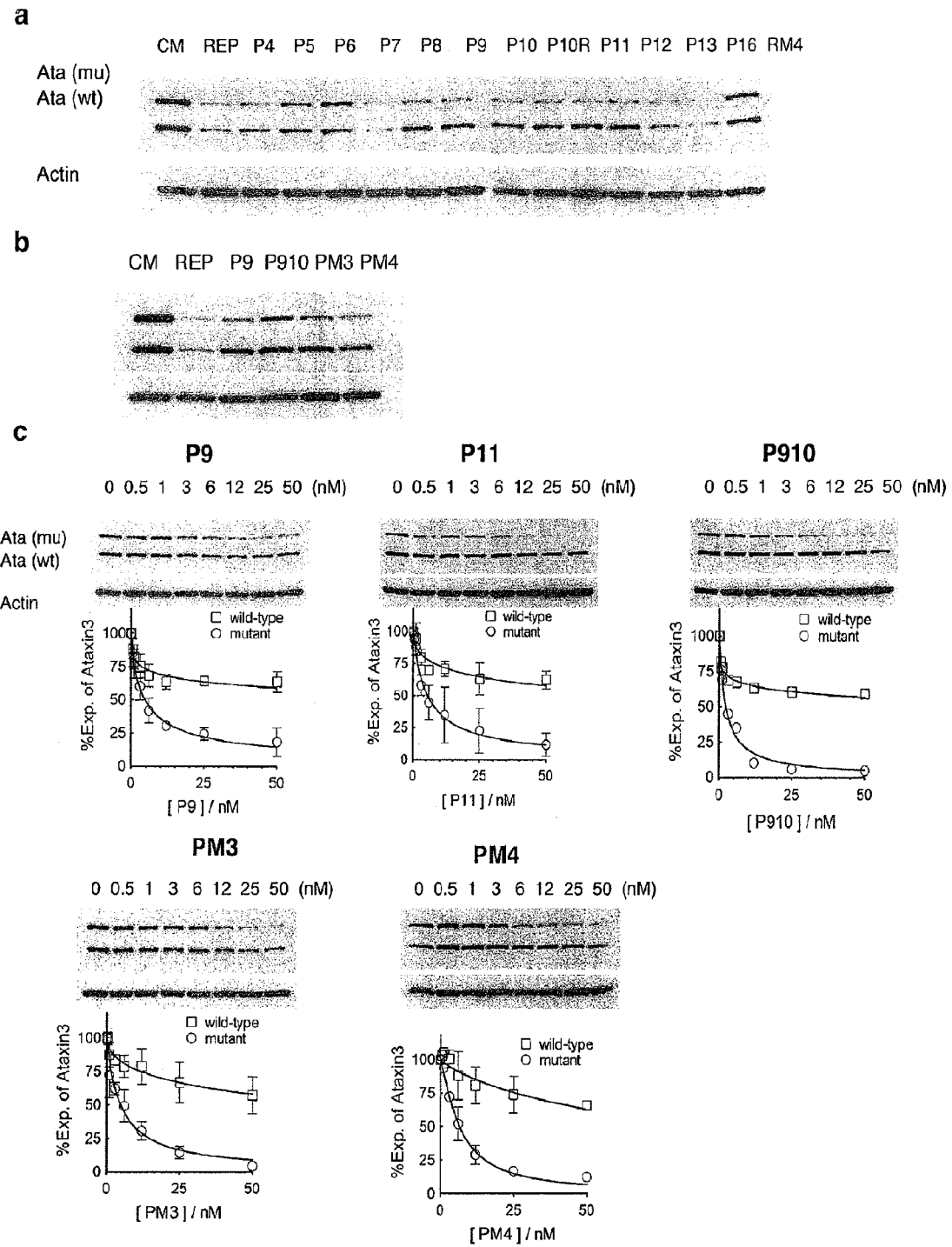
FIGS. 32A-C. Western analysis of ataxin-3 expression in fibroblasts GM06151(CAG 74 mut/24 wt) after treating with siRNAs.

To test whether discouraging cleavage of the target mRNA through introduction of mismatched bases might enhance allele-selectivity, the inventors tested anti-CAG duplexes containing mismatches at positions 4-13 and 16 (FIG. 32A). With the exception of duplex RNA P6 (mutated at position 6), all of the tested duplex RNAs inhibited expression of ATX3. Duplex RNAs P8, P9, P10, p910, P10R, P11, and P12 appeared to be selective for inhibition of the mutant allele. P10R has a mismatch on the guide strand (or antisense strand) that is complementary to HTT mRNA but does not contain a mismatch on the passenger strand. This result is consistent with a mismatch-containing guide strand being necessary for allele-selective inhibition.

The inventors also examined RNA duplexes that had two, three or four mismatched bases (FIG. 32B). $IC_{50}$ values and selectivities for duplexes with one, two, three, or four mismatched bases were similar (FIG. 32C). Potent and selective inhibition by such a wide variety of mismatch-containing duplexes suggests that many different compounds can serve as leads for further development. If one compound is toxic or has unfavorable properties in vivo, another compound may substitute. The inventors have obtained similar potencies and selectivities for inhibition of HTT expression using mismatch-containing RNA duplexes (Hu et al., 2010).

Figure 33:
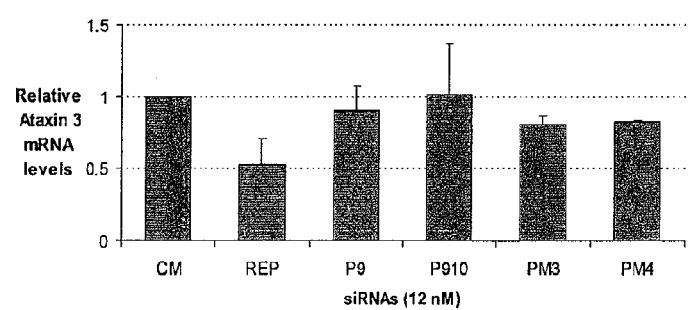
FIG. 33. Selective siRNAs have little effects on ataxin-3 mRNA levels. qPCR analysis of ataxin-3 mRNA levels after treatment with siRNAs at 12 nM concentrations.

To test their hypothesis that the mismatch-containing duplex RNAs function by a mechanism that does not involve RNA cleavage, the inventors we used quantitative PCR (qPCR) to determine the levels of ATX-3 mRNA (FIG. 33). Duplex RNAs P9, P910, PM3, and PM4 caused little or no reduction in amounts of measured ATX-3 mRNA. Fully complementary duplex RNA reduced ATX-3 levels by 50%. These data support the hypothesis that mismatch-containing mRNAs act by blocking translation rather than reducing RNA levels through cleavage of the mRNA target.

TABLE 1

Chemically Modified siRNAs on HTT Expression

| ALNY Name | Lab Name | Sequence | SEQ ID NO: | Tm (° C.) | Mut $IC_{50}$ (nM) | Wt $IC_{50}$ (nM | Selectivity |
|---|---|---|---|---|---|---|---|
| AD 26319-b1 | MP9 | GCUGCUGcAGCUGCUGCUGdTsdT<br>dTdTscGAcGAcGucGAcGAcGAc | 112<br>113 | 89.2 | 2.8 ± 0.2 | >100 | >36 |
| AD 26320-b1 | MP910 | GCUGCUGcAACUGCUGCUGdTsdT<br>dTdTscGAcGAcGuuGAcGAcGAc | 114<br>115 | 85.5 | 2.8 ± 0.3 | >100 | >36 |
| AD 26321-b1 | MP9b | GCUGCUGcAGCUGCUGCUGdTsdT<br>dTdTscGAcGAcGAcGAcGAcGAc | 116<br>117 | 81.1 | 3.3 ± 0.3 | >100 | >30 |
| AD 26322-b1 | MP10b | GCUGCUGCuACUGCUGCUGdTsdT<br>TsTcGAcGAcGAcGAcGAcGAc | 118<br>119 | 79.8 | 6.8 ± 0.7 | >100 | >15 |
| AD 26323-b1 | MP11b | GCUGCUGCUGAUGCUGCUGdTsdT<br>dTdTscGAcGAcGAcGAcGAcGAc | 120<br>121 | 78.4 | 4.9 ± 0.6 | >100 | >20 |
| AD 26324-b1 | MRC/b | CUGCUGCUGAUGCUGCUGCdTsdT<br>dTdTsGAcGAcGAcGAcGAcGAcG | 122<br>123 | 78.2 | 7.1 ± 1.3 | >100 | >14 |
| AD 26325-b1 | MRU/b | UGCUGCUGcAGCUGCUGCUdTsdT<br>dTdTsAcGAcGAcGAcGAcGAcGA | 124<br>125 | 80.2 | 5.1 ± 1.2 | >100 | >20 |
| siRNA with multiple mismatched bases | | | | | | | |
| AD 31197-b1 | G810 | GCUGCUGAuACUGCUGCUGdTsdT<br>dTdTscGAcGAcuAuGACGAcGAc | 126<br>127 | 83.2 | — | — | — |
| AD 31198-b1 | G811 | GCUGCUGAUGAUGCUGCUGdTsdT<br>dTdTsCGAcGAcuAcuAC GAcGAc | 128<br>129 | 82.8 | — | — | — |

TABLE 1-continued

Chemically Modified siRNAs on HTT Expression

| ALNY Name | Lab Name | Sequence | SEQ ID NO: | Tm (°C.) | Mut IC$_{50}$ (nM) | Wt IC$_{50}$ (nM) | Selectivity |
|---|---|---|---|---|---|---|---|
| AD 31199-b1 | G8910 | GCUGCUG*AAA*CUGCUGCUGdTsdT dTdTsCGAcGAcuuuGACGAcGAc | 130 131 | 82.1 | — | — | — |
| AD 31200-b1 | G8911 | GCUGCUGAAGAUGCUGCUGdTsdT dTdTsCGAcGAcuucuAC GAcGAc | 132 133 | 82.9 | 3.3 ± 0.7 | 67 ± 12 | 20 |
| AD 31201-b1 | G91011 | GCUGCUGc*AAA*UGCUGCUGdTsdT dTdTsCGAcGAcG*uuu*ACGAcGAc | 134 135 | 82.2 | 1.4 ± 0.5 | >100 | >71 |
| AD 31202-b1 | G891011 | GCUGCUG*AAAA*UGCUGCUGdTsdT dTdTsCGAcGAc*uuuu*ACGAcGAc | 136 137 | 78.6 | 3.6 ± 1.3 | >100 | >28 |
| AD 31203-b1 | C8910 | CUGCUGc*AAA*UGCUGCUGCdTsdT dTdTsGAcGAcG*uuu*AcGAcGAcG | 138 139 | 82.0 | 20 ± 2.7 | >100 | >5 |
| AD 31204-b1 | C8911 | CUGCUGcAAcAGCUGCUGCdTsdT dTdTsGAcGAcG*uu*GucGAcGAcG | 140 141 | 85.7 | — | — | — |
| AD 31205-b1 | C91011 | CUGCUGCu*AAA*GCUGCUGCdTsdT dTdTsGAcGAcGA*uuu*cGAcGAcG | 142 143 | 82.7 | — | — | — |
| AD 31206-b1 | C891011 | CUGCUGc*AAAA*GCUGCUGCdTsdT dTdTsGAcGAcG*uuuu*cGAcGAcG | 144 145 | 82.7 | 19 ± 4.2 | >100 | >5 |
| AD 31207-b1 | U89 | UGCUGCu*AA*UGCUGCUGCUdTsdT dTdTsACGAcGA*uu*AcGAC GAcGA | 146 147 | 81.6 | — | — | — |
| AD 31208-b1 | U911 | UGCUGCUGAu*A*CUGCUGCUdTsdT dTdTsACGAcGAcu*A*uGAC GAcGA | 148 149 | 81.8 | — | — | — |
| AD 31209-b1 | U8910 | UGCUGCu*AAA*GCUGCUGCUdTsdT dTdTsACGAcGA*uuu*cGAC GAcGA | 150 151 | 81.9 | 2.8 ± | >100 | >36 |
| AD 31210-b1 | U8911 | UGCUGCu*AA*u*A*CUGCUGCUdTsdT dTdTsACGAcGA*uu*A*u*GACGAcGA | 152 153 | 79.7 | 8.6 ± 4.1 | >100 | >120 |
| AD 31211-b1 | U91011 | UGCUGCUGAAACUGCUGCUdTsdT dTdTsACGAcGAcGAc *uuu*GACGAcGA | 154 155 | 83.5 | 2.7 ± 1.1 | >100 | >37 |
| AD 31212-b1 | U891011 | UGCUGCu*AAAA*CUGCUGCUdTsdT dTdTsACGAcGA*uuuu*GAC GAcGA | 156 157 | 79.3 | 7.9 ± 3.2 | >100 | >13 |

The antisense strand of the siRNA is shown from 5' to 3' and the sense strand is from 3' to 5'.
Mismatched bases are underlined and in italics. siRNAs were tested in HD patient fibroblasts GM04281 (mutant allele/69 CAG, wild type/17 CAG repeats). Selectivity is calculated by comparign the IC$_{50}$ for inhibition wild-type versus the IC$_{50}$ for inhibition the mutant HTT protein.

TABLE 2

Chemically-Modified siRNAs with Abasic Bases on HTT Expression

| ALNY Name | Lab Name | Sequence | SEQ ID NO: | Modification | Tm (° C.) | Mut IC$_{50}$ (nM) | Wt IC$_{50}$ (nM) | Selectivity |
|---|---|---|---|---|---|---|---|---|
| AD 36760.1 | MREP | GCUGCUGcUGCUGCUGCUGdTsdT dTdTscGAcGAcGAcGAcGAcGAc | 158 159 | 2'-OMe | 87.9 | — | — | — |
| AD 36761.1 | MP10-1 | GCUGCUGcUACUGCUGCUGdTsdT dTsdTcGAcGAcGAuGAcGAcGAc | 160 161 | 2'-OMe | 84.3 | — | — | — |
| AD 36762.1 | MP11-1 | GCUGCUGcUGAUGCUGCUGdTsdT dTsT cGAcGAcGAcuAcGAcGAc | 162 163 164 | 2'-OMe Y34 | 85.0 79.8 | — — | — — | — — |
| AD 36763.1 | MRU-34 | UGCUGCUGcY34GCUGCUGCUdTsdT dTdTs AcGAcGAcGAcGAcGAcGA | 165 | | | | | |
| AD 36764.1 | MRU-33 | UGCUGCUGcY33GCUGCUGCUdTsdT dTdTsAcGAcGAcGAcGAcGAcGAcGA | 166 167 | Y33 | 78.4 | — | — | — |
| AD 36765.1 | MP9/b-34 | GCUGCUGcY34GCUGCUGCUGdTsdT dTdTscGAcGAcGAcGAcGAcGAc | 168 169 | Y34 | 79.9 | 3.0 ± 0.4 | 75 ± 30 | >25 |
| AD 36766.1 | MP10-34 | GCUGCUGcUY34CUGCUGCUGdTsdT dTdTscGAcGAcGAuGAcGAcGAc | 170 171 | Y34 | 73.9 | 3.7 ± | >100 | >27 |
| AD 36767.1 | MP11-34 | GCUGCUGcUGY34UGCUGCUGdTsdT dTdTscGAcGAcGAcuAcGAc GAc | 172 173 | Y34 | 74.3 | 2.5 ± | >100 | >40 |
| AD 36768.1 | MP9/b-33 | GCUGCUGcY33GCUGCUGCUGdTsdT dTdTscGAcGAcGAcGAcGAcGAc | 174 175 | Y33 | 79.8 | 2.8 ± | >100 | >36 |
| AD 36769.1 | MP10-33 | GCUGCUGcUY33CUGCUGCUGdTsdT dTdTs cGAcGAcGAuGAcGAcGAc | 176 177 | Y33 | 75.3 | 5.8 ± 4.0 | >100 | >17 |
| AD 36770.1 | MP11-33 | GCUGCUGcUGY33UGCUGCUGdTsdT dTdTs cGAcGAcGAcuAcGAcGAc | 178 179 | Y33 | 75.8 | 3.3 ± 0.6 | >100 | >30 |

The antisense strand of the siRNA is shown from 5' to 3' and the sense strand is from 3' to 5'.
Mismatched bases are underlined and in italics. siRNAs were tested in HD patient fibroblasts GM04281 (mutant allele/69 CAG, wild type/17 CAG repeats). Selectivity is calculated by comparing the IC$_{50}$ for inhibition wild-type versus the IC$_{50}$ for inhibition the mutant HTT prot

TABLE 3 siRNAs targeting the ATXN3 CAG repeat region

| siRNA | Sequence | SEQ ID NO: | Position of mismatch | mutIC$_{50}$ (nM) | wtIC$_{50}$ (nM) | Selectivity (fold) |
|---|---|---|---|---|---|---|
| siREP | GCUGCUGCUGCUGCUGCUGTT | 180 | | 12 ± 4 | 24 ± 9 | 2 |
| siP4 | GCUACUGCUGCUGCUGCUGTT | 181 | 4 | — | — | — |
| siP5 | GCUGAUGCUGCUGCUGCUGTT | 182 | 5 | — | — | — |
| siP6 | GCUGCAGCUGCUGCUGCUGTT | 183 | 6 | — | — | — |

TABLE 3 -continued siRNAs targeting the ATXN3 CAG repeat region

| siRNA | Sequence | SEQ ID NO: | Position of mismatch | mutIC$_{50}$ (nM) | wtIC$_{50}$ (nM) | Selectivity (fold) |
|---|---|---|---|---|---|---|
| siP7 | GCUGCUACUGCUGCUGCUGTT | 184 | 7 | — | — | — |
| siP8 | GCUGCUGAUGCUGCUGCUGTT | 1 | 8 | — | — | — |
| siP9 | GCUGCUGCAGCUGCUGCUGTT | 3 | 9 | 4.6 | >50 | 11 |
| siP10 | GCUGCUGCUACUGCUGCUGTT | 5 | 10 | — | — | — |
| siP10R | GCUGCUGCUUCUGCUGCUGTT | 7 | 10 | — | — | — |
| siP11 | GCUGCUGCUGAUGCUGCUGTT | 9 | 11 | 5.4 ± 3.9 | >50 | 9 |
| siP12 | GCUGCUGCUGCAGCUGCUGTT | 185 | 12 | — | — | — |
| siP13 | GCUGCUGCUGCUACUGCUGTT | 186 | 13 | — | — | — |
| siP16 | GCUGCUGCUGCUGCUACUGTT | 187 | 16 | — | — | — |
| siP910 | GCUGCUGCAACUGCUGCUGTT | 11 | 9, 10 | 3.1 ± 0.9 | >50 | 16 |
| siPM3 | GCUGCUGCAAAUGCUGCUGTT | 106 | 9, 10, 11 | 5.2 ± 1.1 | >50 | 10 |
| siPM4 | GCUGCUGAAAAUGCUGCUGTT | 108 | 8, 9, 10, 11 | 6.5 ± 2.8 | >50 | 8 |
| siRM4 | GCAGCUGUUGCUACUGUUGTT | 188 | 3, 8, 13, 17 | — | — | — |
| siCM | GCUAUACCAGCGUCGUCAUTT | 189 | — | — | — | — |

All sequences are listed from 5' to 3'. Only the guide strand of siRNA is showed. Mismatched bases are underlined and in bold letters. Selectivity is calculated by comparing the IC$_{50}$ for inhibition wild-type versus the IC$_{50}$ for inhibition the mutant ataxin-3 protein. siCM is a noncomplementary negative control siRNA. Error is standard deviation. "—" indicates not tested.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. REFERENCES

The following references, to the extent that they provide exemplary procedural or other details supplementary to those set forth herein, are specifically incorporated herein by reference.

U.S. Pat. No. 4,529,561
U.S. Pat. No. 4,737,323
U.S. Pat. No. 4,981,957
U.S. Pat. No. 5,118,800
U.S. Pat. No. 5,319,080
U.S. Pat. No. 5,359,044
U.S. Pat. No. 5,393,878
U.S. Pat. No. 5,446,137
U.S. Pat. No. 5,466,786
U.S. Pat. No. 5,514,785
U.S. Pat. No. 5,519,134
U.S. Pat. No. 5,567,811
U.S. Pat. No. 5,576,427
U.S. Pat. No. 5,591,722
U.S. Pat. No. 5,597,909
U.S. Pat. No. 5,610,300
U.S. Pat. No. 5,627,053
U.S. Pat. No. 5,639,873
U.S. Pat. No. 5,646,265
U.S. Pat. No. 5,658,873
U.S. Pat. No. 5,670,633
U.S. Pat. No. 5,700,920
U.S. Pat. No. 5,792,747
U.S. Pat. No. 6,268,490
U.S. Pat. No. 6,525,191
U.S. Pat. No. 6,531,584
U.S. Pat. No. 6,600,032
U.S. Pat. No. 6,670,461
U.S. Pat. No. 6,747,014
U.S. Pat. No. 6,753,423
U.S. Pat. No. 6,770,748

U.S. Pat. No. 6,794,499
U.S. Pat. No. 7,034,133
U.S. Pat. No. 7,053,207
U.S. Patent Publn. 2003/0082807
U.S. Patent Publn. 2003/0207841
U.S. Patent Publn. 2004/0014959
U.S. Patent Publn. 2004/0143114
U.S. Patent Publn. 2004/0171570
U.S. Patent Publn. 2004/0219565
U.S. Patent Publn. 2008/0015162
Allerson et al., *J. Med. Chem.*, 48:901-904, 2005.
Alves et al., *PLoS One*, 3(10):e3341, 2008.
Bloomfield, *Ann. Rev. Biophys. Bioeng.*, 10:421-450, 1981.
Boado et al., *J. Pharmacol. Exp. Ther.*, 295:239-243, 2002.
Borrell-Pages et al., *Cell. Mol. Life Sci.*, 63:2642-2660, 2004.
Braasch et al., *Chem. Biol.*, 8:1-7, 2001.
Browne and Beal, *Neurochem Res.*, 29(3):531-546, 2004.
Burnett et al., *Hum. Mol. Genet.*, 12(23):3195-3205, 2003.
Chai et al., *J. Biol. Chem.*, 279(5):3605-3611, 2004.
Choung et al., *Biochem. Biophys. Res. Commun.*, 342:919-927, 2006.
Denovan-Wright and Davidson, *Gene Therapy*, 13:525-531, 2006.
DiFiglia et al., *Proc. Natl. Acad. Sci. USA*, 104:17204-17209, 2007.
Donaldson et al., *Curr. Biol.*, 13(3):258-262, 2003.
Dunah et al., *Science*, 296(5576):2238-2243, 2002.
Elayadi et al., *Curr. Opinion Invens. Drugs*, 2:558-561, 2001.
Frieden et al., *Nucleic Acids Res.*, 21:6365-6372, 2003.
Gregoriadis, In: *Liposome Technology*, Vols. 1-3, CRC Press, Boca Raton, Fla., 1993.
Gunawardena and Goldstein, *Arch. Neurol.*, 62(1):46-51, 2005.
Gusella and MacDonald, *Trends. Biochem. Sci.*, 31:533-540, 2006.
Haeberli et al., *Nucleic Acids Res.*, 33:3965-3975, 2005.
Hall et al., *Nucleic Acids Res.*, 32:5991-6000, 2004.
Hall et al., *Nucleic Acids Res.*, 34:2773-2781, 2006.
Harper et al., *Proc. Natl. Acad. USA*, 102:5820-5825, 2005.
Hasholt et al., *J. Gene. Med.*, 5:528-538, 2003.
Hope et al., *Biochim. Biophys. Acta*, 812:55-65, 1985.
Hoshika et al., *Nucleic Acids Res.*, 32:3815-3825, 2004.
Hu et al., *Annals New York Acad. Sci.*, 2009 (in Press).
Hu et al., *Nat. Biotech.*, 27:478, 2009.
Hu et al., *Ann. NY Acad. Sci.*, 1175:24-31, 2009.
Hughes, *Curr. Biol.*, 12(4):R141-143, 2002.
Irwin et al., *J. Cell Sci.*, 118(Pt 1):233-242, 2005.
Janoff, In: *Liposomes: Rational Design*, Marcel Dekker, NY, 1999.
Kaur et al., *Biochemistry*, 45:7347-55, 2006.
Kazantsev et al., *Proc. Natl. Acad. Sci. USA*, 96(20):11404-11409, 1999.
Klement et al., *Cell*, 95(1):41-53, 1998.
Koshkin et al., *Tetrahedron*, 54:3607-3630, 1998.
Kumar et al., *Bioorg. Med. Chem. Lett.*, 8:2219-2222, 1998.
Li et al., *J Biol Chem.*, 277(31):28212-28221, 2002.
Li et al., *Nat. Med.*, 11:944-951, 2005.
Mao et al., *Proc. Natl. Acad. Sci. USA*, 102(36):12700-12705, 2005.
Morita et al., *Bioorganic Medicinal Chem.*, 11:2211-2226, 2003.
Nasir et al., *Cell*, 81:811-823, 1995.
Nicastro et al., *Proc. Natl. Acad. Sci. USA*, 102(30):10493-10498, 2005.
Nucifora et al., *Science*, 291(5512):2423-2428, 2001.
Orum et al., *Curr. Opinion Mol. Ther.*, 3:239-243, 2001.
PCT Appln. WO 2005/021570
PCT Appln. WO 2005/121371
PCT Appln. WO 2005/115481
PCT Appln. WO 94/14226
PCT Appln. WO 98/39352
PCT Appln. WO 99/14226
Prakash et al., *J. Med. Chem.*, 48:4247-4253, 2005.
Rand et al., *Cell*, 123:621-629, 2005.
Remington's Pharmaceutical Sciences, 15$^{th}$ ed., pages 1035-1038 and 1570-1580, Mack Publishing Company, Easton, Pa., 1980.
Rodriguez-Lebrón et al., *Mol. Ther.*, 17(9):1563-73, 2009.
Rodriguez-Lebrón and Paulson, *Gene Therapy*, 13:576-581, 2006.
Scheel et al., *Hum. Mol. Genet.*, 12(21):2845-2852, 2003.
Schwarz et al., *PLOS Genetics*, 2:1307-1318, 2006.
Scholefield & Wood, *Trends Genetics*, 26(1):29-38, 2009.
Servadio et al., *Nat. Genet.*, 10(1):94-98, 1995.
Shah, In: *Micelles, Microemulsions, and Monolayers: Science and Technology*, Marcel Dekker, NY, 1998.
Singh et al., *Chem. Commun.*, 4:455-456, 1998.
Singh et al., *J. Org. Chem.*, 63:10035-10039, 1998.
Soutschek et al., *Nature*, 432(7014):173-178, 2004.
Steffan et al., *Nature*, 413(6857):739-743, 2001.
Szoka and Papahadjopoulos, *Proc. Natl. Acad. Sci. USA*, 75:4194 4198, 1978.
van Bielsen et al., *Hum. Gene Ther.*, 19(7):710-9, 2008.
Wahlestedt et al., *Proc. Natl. Acad. Sci. USA*, 97:5633-5638, 2000.
Walker, *Lancet*, 369:218-228, 2007.
Warrick et al., *Mol. Cell*, 18(1):37-48, 2005.
White et al., *Nat. Genetics*, 17:404-410, 1997.
You et al., *Nucl. Acids Res.*, 34:e60, 2006.
Yue et al., *Hum. Mol. Genet.*, 10(1):25-30, 2001.
Zhai et al. *Cell*, 123(7):1241-53, 2005.
Zimmerman et al., *Nature*, 441:111-114, 2006.

---

What is claimed:

1. A method for selectively inhibiting expression of a disease protein encoded by an mRNA having expanded CAG repeat region comprising contacting a cell that produces said disease protein with a double-stranded RNA of 15-30 bases that targets said expanded CAG repeat region of a disease protein mRNA, and said double-stranded RNA further contains 1, 2, 3, 4 or 5 base mismatches as compared to the targeted expanded CAG repeat, wherein (i) inhibiting is selective for said disease protein expression over expression of a normal form of said disease protein, an mRNA for said normal form which lacks said expanded CAG repeat region, (ii) said double-stranded RNA contains no more than one base mismatch in a seed sequence, and (iii) said double-stranded RNA contains the same number of mismatches to the disease protein mRNA as it does to the normal form of said disease protein mRNA, further comprising wherein one strand of the double-stranded RNA has one of the following sequences:

GCUGCUGAUGCUGCUGCUGTT (SEQ ID NO 1),
GCUGCUGCAGCUGCUGCUGTT (SEQ ID NO 3),
GCUGCUGCUACUGCUGCUGTT (SEQ ID NO 5),
GCUGCUGCUUCUGCUGCUGTT (SEQ ID NO 7),
GCUGCUGCUGAUGCUGCUGTT (SEQ ID NO 9), or
UGCUGCUGCAGCUGCUGCUTT (SEQ ID NO 25).

2. A method for selectively inhibiting expression of a disease protein encoded by an mRNA having expanded CAG repeat region comprising contacting a cell that produces said disease protein with a double-stranded RNA of 15-30 bases that targets said expanded CAG repeat region of a disease protein mRNA, and said double-stranded RNA further contains 1, 2, 3, 4 or 5 base mismatches as compared to the targeted expanded CAG repeat, wherein (i) inhibiting is selective for said disease protein expression over expression of a normal form of said disease protein, an mRNA for said normal form which lacks said expanded CAG repeat region, (ii) said double-stranded RNA contains no more than one base mismatch in a seed sequence, and (iii) said double-stranded RNA contains the same number of mismatches to the disease protein mRNA as it does to the normal form of said disease protein mRNA, further comprising wherein one strand of the double-stranded RNA has one of the following sequences:

GCUGCUGCAACUGCUGCUGTT (SEQ ID NO 11),
GCUGCUGCAAAUGCUGCUGTT (SEQ ID NO 106), or
GCUGCUGAAAAUGCUGCUGTT (SEQ ID NO 108).

* * * * *

SEQUENCE LISTING

```
<160> NUMBER OF SEQ ID NOS: 202

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
gcugcugaug cugcugcugt t                                               21
```

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
ttcgacgacu acgacgacga c                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
gcugcugcag cugcugcugt t                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
ttcgacgacg ucgacgacga c                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
gcugcugcua cugcugcugt t                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
ttcgacgacg augacgacga c                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
gcugcugcuu cugcugcugt t                                              21

<210> SEQ ID NO 8
<211> LENGTH: 21
<212> TYPE: DNA
<213> ORGANISM: Artificial Sequence
<220> FEATURE:

<223> OTHER INFORMATION: Synthetic primer

<400> SEQUENCE: 8
ttcgacgacg aagacgacga c					21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
gcugcugcug augcugcugt t					21

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
ttcgacgacg acuacgacga c					21

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
gcugcugcaa cugcugcugt t					21

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
ttcgacgacg uugacgacga c					21

<210> SEQ ID NO 13
<211> LENGTH: 21
<212> TYPE: DNA
<213> ORGANISM: Artificial Sequence
<220> FEATURE:
<223> OTHER INFORMATION: Synthetic primer

<400> SEQUENCE: 13
gcugcugcag cugcugcugt t					21

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
ttcgacgacg acgacgacga c					21

```
<210> SEQ ID NO 15
<211> LENGTH: 21
<212> TYPE: DNA
<213> ORGANISM: Artificial Sequence
<220> FEATURE:
<223> OTHER INFORMATION: Synthetic primer

<400> SEQUENCE: 15
gcugcugcua cugcugcugt t                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
ttcgacgacg acgacgacga c                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic primer

<400> SEQUENCE: 17
gcugcugcuu cugcugcugt t                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
ttcgacgacg acgacgacga c                                              21

<210> SEQ ID NO 19
<211> LENGTH: 21
<212> TYPE: DNA
<213> ORGANISM: Artificial Sequence
<220> FEATURE:
<223> OTHER INFORMATION: Synthetic primer

<400> SEQUENCE: 19
gcugcugcug augcugcugt t                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetic primer

<400> SEQUENCE: 20
ttcgacgacg acgacgacga c                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic primer
```

```
<400> SEQUENCE: 21
gcugcugcaa cugcugcugt t                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic primer

<400> SEQUENCE: 22
ttcgacgacg acgacgacga c                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic primer

<400> SEQUENCE: 23
cugcugcuga ugcugcugct t                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic primer

<400> SEQUENCE: 24
ttgacgacga cgacgacgac g                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic primer

<400> SEQUENCE: 25
ugcugcugca gcugcugcut t                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic primer

<400> SEQUENCE: 26
ttacgacgac gacgacgacg a                                              21

<210> SEQ ID NO 27
<211> LENGTH: 22
<212> TYPE: DNA
<213> ORGANISM: Artificial Sequence
<220> FEATURE:
<223> OTHER INFORMATION: Synthetic primer

<400> SEQUENCE: 27
gcugcugcag cugcugcugt st                                             22

<210> SEQ ID NO 28
<211> LENGTH: 22
```

<212> TYPE: DNA
<213> ORGANISM: Artificial Sequence
<220> FEATURE:
<223> OTHER INFORMATION: Synthetic primer

<400> SEQUENCE: 28
tstcgacgac gucgacgacg ac                                           22

<210> SEQ ID NO 29
<211> LENGTH: 22
<212> TYPE: DNA
<213> ORGANISM: Artificial Sequence
<220> FEATURE:
<223> OTHER INFORMATION: Synthetic primer

<400> SEQUENCE: 29
gcugcugcaa cugcugcugt st                                           22

<210> SEQ ID NO 30
<211> LENGTH: 22
<212> TYPE: DNA
<213> ORGANISM: Artificial Sequence
<220> FEATURE:
<223> OTHER INFORMATION: Synthetic primer

<400> SEQUENCE: 30
tstcgacgac guugacgacg ac                                           22

<210> SEQ ID NO 31
<211> LENGTH: 22
<212> TYPE: DNA
<213> ORGANISM: Artificial Sequence
<220> FEATURE:
<223> OTHER INFORMATION: Synthetic primer

<400> SEQUENCE: 31
gcugcugcag cugcugcugt st                                           22

<210> SEQ ID NO 32
<211> LENGTH: 22
<212> TYPE: DNA
<213> ORGANISM: Artificial Sequence
<220> FEATURE:
<223> OTHER INFORMATION: Synthetic primer

<400> SEQUENCE: 32
tstcgacgac gacgacgacg ac                                           22

<210> SEQ ID NO 33
<211> LENGTH: 22
<212> TYPE: DNA
<213> ORGANISM: Artificial Sequence
<220> FEATURE:
<223> OTHER INFORMATION: Synthetic primer

<400> SEQUENCE: 33
gcugcugcua cugcugcugt st                                           22

<210> SEQ ID NO 34
<211> LENGTH: 22
<212> TYPE: DNA
<213> ORGANISM: Artificial Sequence
<220> FEATURE:
<223> OTHER INFORMATION: Synthetic primer

<400> SEQUENCE: 34
tstcgacgac gacgacgacg ac                                              22

<210> SEQ ID NO 35
<211> LENGTH: 22
<212> TYPE: DNA
<213> ORGANISM: Artificial Sequence
<220> FEATURE:
<223> OTHER INFORMATION: Synthetic primer

<400> SEQUENCE: 35
gcugcugcug augcugcugt st                                              22

<210> SEQ ID NO 36
<211> LENGTH: 22
<212> TYPE: DNA
<213> ORGANISM: Artificial Sequence
<220> FEATURE:
<223> OTHER INFORMATION: Synthetic primer

<400> SEQUENCE: 36
tstcgacgac gacgacgacg ac                                              22

<210> SEQ ID NO 37
<211> LENGTH: 22
<212> TYPE: DNA
<213> ORGANISM: Artificial Sequence
<220> FEATURE:
<223> OTHER INFORMATION: Synthetic primer

<400> SEQUENCE: 37
cugcugcuga ugcugcugct st                                              22

<210> SEQ ID NO 38
<211> LENGTH: 22
<212> TYPE: DNA
<213> ORGANISM: Artificial Sequence
<220> FEATURE:
<223> OTHER INFORMATION: Synthetic primer

<400> SEQUENCE: 38
tstgacgacg acgacgacga cg                                              22

<210> SEQ ID NO 39
<211> LENGTH: 22
<212> TYPE: DNA
<213> ORGANISM: Artificial Sequence
<220> FEATURE:
<223> OTHER INFORMATION: Synthetic primer

<400> SEQUENCE: 39
ugcugcugca gcugcugcut st                                              22

<210> SEQ ID NO 40
<211> LENGTH: 22
<212> TYPE: DNA
<213> ORGANISM: Artificial Sequence
<220> FEATURE:
<223> OTHER INFORMATION: Synthetic primer

<400> SEQUENCE: 40
tstacgacga cgacgacgac ga                                              22

<210> SEQ ID NO 41
<211> LENGTH: 10
<212> TYPE: DNA
<213> ORGANISM: Artificial Sequence

```
<220> FEATURE:
<223> OTHER INFORMATION: Synthetic primer

<400> SEQUENCE: 41
atgcatgcat                                                          10

<210> SEQ ID NO 42
<211> LENGTH: 11
<212> TYPE: DNA
<213> ORGANISM: Artificial Sequence
<220> FEATURE:
<223> OTHER INFORMATION: Synthetic primer

<400> SEQUENCE: 42
atgcatgcat g                                                        11

<210> SEQ ID NO 43
<211> LENGTH: 12
<212> TYPE: DNA
<213> ORGANISM: Artificial Sequence
<220> FEATURE:
<223> OTHER INFORMATION: Synthetic primer

<400> SEQUENCE: 43
atgcatgcat gc                                                       12

<210> SEQ ID NO 44
<211> LENGTH: 13
<212> TYPE: DNA
<213> ORGANISM: Artificial Sequence
<220> FEATURE:
<223> OTHER INFORMATION: Synthetic primer

<400> SEQUENCE: 44
atgcatgcat gca                                                      13

<210> SEQ ID NO 45
<211> LENGTH: 14
<212> TYPE: DNA
<213> ORGANISM: Artificial Sequence
<220> FEATURE:
<223> OTHER INFORMATION: Synthetic primer

<400> SEQUENCE: 45
atgcatgcat gcat                                                     14

<210> SEQ ID NO 46
<211> LENGTH: 15
<212> TYPE: DNA
<213> ORGANISM: Artificial Sequence
<220> FEATURE:
<223> OTHER INFORMATION: Synthetic primer

<400> SEQUENCE: 46
atgcatgcat gcatg                                                    15

<210> SEQ ID NO 47
<211> LENGTH: 16
<212> TYPE: DNA
<213> ORGANISM: Artificial Sequence
<220> FEATURE:
<223> OTHER INFORMATION: Synthetic primer

<400> SEQUENCE: 47
atgcatgcat gcatgc                                                   16
```

```
<210> SEQ ID NO 48
<211> LENGTH: 17
<212> TYPE: DNA
<213> ORGANISM: Artificial Sequence
<220> FEATURE:
<223> OTHER INFORMATION: Synthetic primer

<400> SEQUENCE: 48
atgcatgcat gcatgca                                                    17

<210> SEQ ID NO 49
<211> LENGTH: 18
<212> TYPE: DNA
<213> ORGANISM: Artificial Sequence
<220> FEATURE:
<223> OTHER INFORMATION: Synthetic primer

<400> SEQUENCE: 49
atgcatgcat gcatgcat                                                   18

<210> SEQ ID NO 50
<211> LENGTH: 19
<212> TYPE: DNA
<213> ORGANISM: Artificial Sequence
<220> FEATURE:
<223> OTHER INFORMATION: Synthetic primer

<400> SEQUENCE: 50
atgcatgcat gcatgcatg                                                  19

<210> SEQ ID NO 51
<211> LENGTH: 20
<212> TYPE: DNA
<213> ORGANISM: Artificial Sequence
<220> FEATURE:
<223> OTHER INFORMATION: Synthetic primer

<400> SEQUENCE: 51
atgcatgcat gcatgcatgc                                                 20

<210> SEQ ID NO 52
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 52
gcugcugaua cugcugcugt st                                              22

<210> SEQ ID NO 53
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 53
ttscgacgac uaugacgacg ac                                              22
```

<210> SEQ ID NO 54
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 54
gcugcugaug augcugcugt st                                    22

<210> SEQ ID NO 55
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 55
ttscgacgac uacuacgacg ac                                    22

<210> SEQ ID NO 56
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 56
gcugcugaaa cugcugcugt st                                    22

<210> SEQ ID NO 57
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 57
ttscgacgac uuugacgacg ac                                    22

<210> SEQ ID NO 58
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 58
gcugcugaag augcugcugt st                                                22

<210> SEQ ID NO 59
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 59
ttscgacgac uucuacgacg ac                                                22

<210> SEQ ID NO 60
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 60
gcugcugcaa augcugcugt st                                                22

<210> SEQ ID NO 61
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 61
ttscgacgac guuuacgacg ac                                                22

<210> SEQ ID NO 62
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 62
gcugcugaaa augcugcugt st                                                22

<210> SEQ ID NO 63
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 63
ttscgacgac uuuuacgacg ac                                              22

<210> SEQ ID NO 64
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 64
cugcugcaaa ugcugcugct st                                              22

<210> SEQ ID NO 65
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 65
ttsgacgacg uuuacgacga cg                                              22

<210> SEQ ID NO 66
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 66
cugcugcaac agcugcugct st                                              22

<210> SEQ ID NO 67
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 67
ttsgacgacg uugucgacga cg                                              22

<210> SEQ ID NO 68
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 68
cugcugcuaa agcugcugct st                                                      22

<210> SEQ ID NO 69
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 69
ttsgacgacg auuucgacga cg                                                      22

<210> SEQ ID NO 70
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 70
cugcugcaaa agcugcugct st                                                      22

<210> SEQ ID NO 71
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 71
ttsgacgacg uuuucgacga cg                                                      22

<210> SEQ ID NO 72
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 72
ugcugcuaau gcugcugcut st                                                      22

<210> SEQ ID NO 73
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

```
<400> SEQUENCE: 73
ttsacgacga uuacgacgac ga                                              22

<210> SEQ ID NO 74
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 74
ugcugcugau acugcugcut st                                              22

<210> SEQ ID NO 75
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 75
ttsacgacga cuaugacgac ga                                              22

<210> SEQ ID NO 76
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 76
ugcugcuaaa gcugcugcut st                                              22

<210> SEQ ID NO 77
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 77
ttsacgacga uuucgacgac ga                                              22

<210> SEQ ID NO 78
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
```

<223> OTHER INFORMATION: This is combined DNA/RNA sequence.

<400> SEQUENCE: 78
ugcugcuaau acugcugcut st                                            22

<210> SEQ ID NO 79
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 79
ttsacgacga uuaugacgac ga                                            22

<210> SEQ ID NO 80
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 80
ugcugcugaa acugcugcut st                                            22

<210> SEQ ID NO 81
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 81
ttsacgacga cuuugacgac ga                                            22

<210> SEQ ID NO 82
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 82
ugcugcuaaa acugcugcut st                                            22

<210> SEQ ID NO 83
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature

```
<222> LOCATION: (1)..(22)
<223> OTHER INFORMATION: This is combined DNA/RNA sequence.

<400> SEQUENCE: 83
ttsacgacga uuuugacgac ga                                              22

<210> SEQ ID NO 84
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 84
gcugcugcug cugcugcugt st                                              22

<210> SEQ ID NO 85
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 85
ttscgacgac gacgacgacg ac                                              22

<210> SEQ ID NO 86
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 86
gcugcugcua cugcugcugt st                                              22

<210> SEQ ID NO 87
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 87
tstcgacgac gaugacgacg ac                                              22

<210> SEQ ID NO 88
<211> LENGTH: 22
<212> TYPE: DNA
<213> ORGANISM: Artificial Sequence
<220> FEATURE:
<223> OTHER INFORMATION: Synthetic primer
<220> FEATURE:
```

```
<221> NAME/KEY: misc_feature
<222> LOCATION: (1)..(22)
<223> OTHER INFORMATION: This is combined DNA/RNA sequence.

<400> SEQUENCE: 88
gcugcugcug augcugcugt st                                                  22

<210> SEQ ID NO 89
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 89
tstcgacgac gacuacgacg ac                                                  22

<210> SEQ ID NO 90
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 90
ugcugcugcg cugcugcuts t                                                   21

<210> SEQ ID NO 91
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 91
ttsacgacga cgacgacgac ga                                                  22

<210> SEQ ID NO 92
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 92
ugcugcugcg cugcugcuts t                                                   21

<210> SEQ ID NO 93
<211> LENGTH: 22
<212> TYPE: DNA
<213> ORGANISM: Artificial Sequence
<220> FEATURE:
<223> OTHER INFORMATION: Synthetic primer
```

```
<220> FEATURE:
<221> NAME/KEY: misc_feature
<222> LOCATION: (1)..(22)
<223> OTHER INFORMATION: This is combined DNA/RNA sequence.

<400> SEQUENCE: 93
ttsacgacga cgacgacgac ga                                              22

<210> SEQ ID NO 94
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 94
gcugcugcgc ugcugcugts t                                               21

<210> SEQ ID NO 95
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 95
ttscgacgac gacgacgacg ac                                              22

<210> SEQ ID NO 96
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 96
gcugcugcuc ugcugcugts t                                               21

<210> SEQ ID NO 97
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 97
ttscgacgac gaugacgacg ac                                              22

<210> SEQ ID NO 98
<211> LENGTH: 21
<212> TYPE: DNA
<213> ORGANISM: Artificial Sequence
<220> FEATURE:
```

<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 98
gcugcugcug ugcugcugts t                                              21

<210> SEQ ID NO 99
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 99
ttscgacgac gacuacgacg ac                                             22

<210> SEQ ID NO 100
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 100
gcugcugcgc ugcugcugts t                                              21

<210> SEQ ID NO 101
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 101
ttscgacgac gacgacgacg ac                                             22

<210> SEQ ID NO 102
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 102
gcugcugcuc ugcugcugts t                                              21

<210> SEQ ID NO 103
<211> LENGTH: 22
<212> TYPE: DNA
<213> ORGANISM: Artificial Sequence

```
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 103
ttscgacgac gaugacgacg ac                                              22

<210> SEQ ID NO 104
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 104
gcugcugcug ugcugcugts t                                               21

<210> SEQ ID NO 105
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 105
ttscgacgac gacuacgacg ac                                              22

<210> SEQ ID NO 106
<211> LENGTH: 21
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(21)
<223> OTHER INFORMATION: This is combined DNA/RNA sequence

<400> SEQUENCE: 106
gcugcugcaa augcugcugt t                                               21

<210> SEQ ID NO 107
<211> LENGTH: 21
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(21)
<223> OTHER INFORMATION: This is combined DNA/RNA sequence

<400> SEQUENCE: 107
ttcgacgacg acgacgacga c                                               21

<210> SEQ ID NO 108
<211> LENGTH: 21
<212> TYPE: DNA
```

<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(21)
<223> OTHER INFORMATION: This is combined DNA/RNA sequence

<400> SEQUENCE: 108
gcugcugaaa augcugcugt t                                              21

<210> SEQ ID NO 109
<211> LENGTH: 21
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(21)
<223> OTHER INFORMATION: This is combined DNA/RNA sequence

<400> SEQUENCE: 109
ttcgacgacg acgacgacga c                                              21

<210> SEQ ID NO 110
<211> LENGTH: 20
<212> TYPE: DNA
<213> ORGANISM: Artificial Sequence
<220> FEATURE:
<223> OTHER INFORMATION: Synthetic Primer

<400> SEQUENCE: 110
ggaaatatgg atgacagtgg                                                20

<210> SEQ ID NO 111
<211> LENGTH: 20
<212> TYPE: DNA
<213> ORGANISM: Artificial Sequence
<220> FEATURE:
<223> OTHER INFORMATION: Synthetic Primer

<400> SEQUENCE: 111
atcctgagcc tctgatactc                                                20

<210> SEQ ID NO 112
<211> LENGTH: 24
<212> TYPE: DNA
<213> ORGANISM: Artificial Sequence
<220> FEATURE:
<223> OTHER INFORMATION: Synthetic Primer

<400> SEQUENCE: 112
gcugcugcag cugcugcugd tsdt                                           24

<210> SEQ ID NO 113
<211> LENGTH: 24
<212> TYPE: DNA
<213> ORGANISM: Artificial Sequence
<220> FEATURE:
<223> OTHER INFORMATION: Synthetic Primer

<400> SEQUENCE: 113
dtdtscgacg acgucgacga cgac                                           24

<210> SEQ ID NO 114
<211> LENGTH: 24

```
<212> TYPE: DNA
<213> ORGANISM: Artificial Sequence
<220> FEATURE:
<223> OTHER INFORMATION: Synthetic Primer

<400> SEQUENCE: 114
gcugcugcaa cugcugcugd tsdt                                              24

<210> SEQ ID NO 115
<211> LENGTH: 24
<212> TYPE: DNA
<213> ORGANISM: Artificial Sequence
<220> FEATURE:
<223> OTHER INFORMATION: Synthetic Primer

<400> SEQUENCE: 115
dtdtscgacg acguugacga cgac                                              24

<210> SEQ ID NO 116
<211> LENGTH: 24
<212> TYPE: DNA
<213> ORGANISM: Artificial Sequence
<220> FEATURE:
<223> OTHER INFORMATION: Synthetic Primer

<400> SEQUENCE: 116
gcugcugcag cugcugcugd tsdt                                              24

<210> SEQ ID NO 117
<211> LENGTH: 24
<212> TYPE: DNA
<213> ORGANISM: Artificial Sequence
<220> FEATURE:
<223> OTHER INFORMATION: Synthetic Primer

<400> SEQUENCE: 117
dtdtscgacg acgacgacga cgac                                              24

<210> SEQ ID NO 118
<211> LENGTH: 24
<212> TYPE: DNA
<213> ORGANISM: Artificial Sequence
<220> FEATURE:
<223> OTHER INFORMATION: Synthetic Primer

<400> SEQUENCE: 118
gcugcugcua cugcugcugd tsdt                                              24

<210> SEQ ID NO 119
<211> LENGTH: 22
<212> TYPE: DNA
<213> ORGANISM: Artificial Sequence
<220> FEATURE:
<223> OTHER INFORMATION: Synthetic Primer

<400> SEQUENCE: 119
tstcgacgac gacgacgacg ac                                                22

<210> SEQ ID NO 120
<211> LENGTH: 24
<212> TYPE: DNA
<213> ORGANISM: Artificial Sequence
<220> FEATURE:
<223> OTHER INFORMATION: Synthetic Primer

<400> SEQUENCE: 120
```

```
gcugcugcug augcugcugd tsdt                                              24
```

<210> SEQ ID NO 121
<211> LENGTH: 24
<212> TYPE: DNA
<213> ORGANISM: Artificial Sequence
<220> FEATURE:
<223> OTHER INFORMATION: Synthetic Primer

<400> SEQUENCE: 121

```
dtdtscgacg acgacgacga cgac                                              24
```

<210> SEQ ID NO 122
<211> LENGTH: 24
<212> TYPE: DNA
<213> ORGANISM: Artificial Sequence
<220> FEATURE:
<223> OTHER INFORMATION: Synthetic Primer

<400> SEQUENCE: 122

```
cugcugcuga ugcugcugcd tsdt                                              24
```

<210> SEQ ID NO 123
<211> LENGTH: 24
<212> TYPE: DNA
<213> ORGANISM: Artificial Sequence
<220> FEATURE:
<223> OTHER INFORMATION: Synthetic Primer

<400> SEQUENCE: 123

```
dtdtsgacga cgacgacgac gacg                                              24
```

<210> SEQ ID NO 124
<211> LENGTH: 24
<212> TYPE: DNA
<213> ORGANISM: Artificial Sequence
<220> FEATURE:
<223> OTHER INFORMATION: Synthetic Primer

<400> SEQUENCE: 124

```
ugcugcugca gcugcugcud tsdt                                              24
```

<210> SEQ ID NO 125
<211> LENGTH: 24
<212> TYPE: DNA
<213> ORGANISM: Artificial Sequence
<220> FEATURE:
<223> OTHER INFORMATION: Synthetic Primer

<400> SEQUENCE: 125

```
dtdtsacgac gacgacgacg acga                                              24
```

<210> SEQ ID NO 126
<211> LENGTH: 24
<212> TYPE: DNA
<213> ORGANISM: Artificial Sequence
<220> FEATURE:
<223> OTHER INFORMATION: Synthetic Primer

<400> SEQUENCE: 126

```
gcugcugaua cugcugcugd tsdt                                              24
```

<210> SEQ ID NO 127
<211> LENGTH: 24
<212> TYPE: DNA
<213> ORGANISM: Artificial Sequence

```
<220> FEATURE:
<223> OTHER INFORMATION: Synthetic Primer

<400> SEQUENCE: 127
dtdtscgacg acuaugacga cgac                                              24

<210> SEQ ID NO 128
<211> LENGTH: 24
<212> TYPE: DNA
<213> ORGANISM: Artificial Sequence
<220> FEATURE:
<223> OTHER INFORMATION: Synthetic Primer

<400> SEQUENCE: 128
gcugcugaug augcugcugd tsdt                                              24

<210> SEQ ID NO 129
<211> LENGTH: 24
<212> TYPE: DNA
<213> ORGANISM: Artificial Sequence
<220> FEATURE:
<223> OTHER INFORMATION: Synthetic Primer

<400> SEQUENCE: 129
dtdtscgacg acuacuacga cgac                                              24

<210> SEQ ID NO 130
<211> LENGTH: 24
<212> TYPE: DNA
<213> ORGANISM: Artificial Sequence
<220> FEATURE:
<223> OTHER INFORMATION: Synthetic Primer

<400> SEQUENCE: 130
gcugcugaaa cugcugcugd tsdt                                              24

<210> SEQ ID NO 131
<211> LENGTH: 24
<212> TYPE: DNA
<213> ORGANISM: Artificial Sequence
<220> FEATURE:
<223> OTHER INFORMATION: Synthetic Primer

<400> SEQUENCE: 131
dtdtscgacg acuuugacga cgac                                              24

<210> SEQ ID NO 132
<211> LENGTH: 24
<212> TYPE: DNA
<213> ORGANISM: Artificial Sequence
<220> FEATURE:
<223> OTHER INFORMATION: Synthetic Primer

<400> SEQUENCE: 132
gcugcugaag augcugcugd tsdt                                              24

<210> SEQ ID NO 133
<211> LENGTH: 24
<212> TYPE: DNA
<213> ORGANISM: Artificial Sequence
<220> FEATURE:
<223> OTHER INFORMATION: Synthetic Primer

<400> SEQUENCE: 133
dtdtscgacg acuucuacga cgac                                              24
```

```
<210> SEQ ID NO 134
<211> LENGTH: 24
<212> TYPE: DNA
<213> ORGANISM: Artificial Sequence
<220> FEATURE:
<223> OTHER INFORMATION: Synthetic Primer

<400> SEQUENCE: 134
gcugcugcaa augcugcugd tsdt                                            24

<210> SEQ ID NO 135
<211> LENGTH: 24
<212> TYPE: DNA
<213> ORGANISM: Artificial Sequence
<220> FEATURE:
<223> OTHER INFORMATION: Synthetic Primer

<400> SEQUENCE: 135
dtdtscgacg acguuuacga cgac                                            24

<210> SEQ ID NO 136
<211> LENGTH: 24
<212> TYPE: DNA
<213> ORGANISM: Artificial Sequence
<220> FEATURE:
<223> OTHER INFORMATION: Synthetic Primer

<400> SEQUENCE: 136
gcugcugaaa augcugcugd tsdt                                            24

<210> SEQ ID NO 137
<211> LENGTH: 24
<212> TYPE: DNA
<213> ORGANISM: Artificial Sequence
<220> FEATURE:
<223> OTHER INFORMATION: Synthetic Primer

<400> SEQUENCE: 137
dtdtscgacg acuuuacga cgac                                             24

<210> SEQ ID NO 138
<211> LENGTH: 24
<212> TYPE: DNA
<213> ORGANISM: Artificial Sequence
<220> FEATURE:
<223> OTHER INFORMATION: Synthetic Primer

<400> SEQUENCE: 138
cugcugcaaa ugcugcugcd tsdt                                            24

<210> SEQ ID NO 139
<211> LENGTH: 24
<212> TYPE: DNA
<213> ORGANISM: Artificial Sequence
<220> FEATURE:
<223> OTHER INFORMATION: Synthetic Primer

<400> SEQUENCE: 139
dtdtsgacga cguuuacgac gacg                                            24

<210> SEQ ID NO 140
<211> LENGTH: 24
<212> TYPE: DNA
<213> ORGANISM: Artificial Sequence
<220> FEATURE:
<223> OTHER INFORMATION: Synthetic Primer
```

```
<400> SEQUENCE: 140
cugcugcaac agcugcugcd tsdt                                              24

<210> SEQ ID NO 141
<211> LENGTH: 24
<212> TYPE: DNA
<213> ORGANISM: Artificial Sequence
<220> FEATURE:
<223> OTHER INFORMATION: Synthetic Primer

<400> SEQUENCE: 141
dtdtsgacga cguugucgac gacg                                              24

<210> SEQ ID NO 142
<211> LENGTH: 24
<212> TYPE: DNA
<213> ORGANISM: Artificial Sequence
<220> FEATURE:
<223> OTHER INFORMATION: Synthetic Primer

<400> SEQUENCE: 142
cugcugcuaa agcugcugcd tsdt                                              24

<210> SEQ ID NO 143
<211> LENGTH: 24
<212> TYPE: DNA
<213> ORGANISM: Artificial Sequence
<220> FEATURE:
<223> OTHER INFORMATION: Synthetic Primer

<400> SEQUENCE: 143
dtdtsgacga cgauuucgac gacg                                              24

<210> SEQ ID NO 144
<211> LENGTH: 24
<212> TYPE: DNA
<213> ORGANISM: Artificial Sequence
<220> FEATURE:
<223> OTHER INFORMATION: Synthetic Primer

<400> SEQUENCE: 144
cugcugcaaa agcugcugcd tsdt                                              24

<210> SEQ ID NO 145
<211> LENGTH: 24
<212> TYPE: DNA
<213> ORGANISM: Artificial Sequence
<220> FEATURE:
<223> OTHER INFORMATION: Synthetic Primer

<400> SEQUENCE: 145
dtdtsgacga cguuuucgac gacg                                              24

<210> SEQ ID NO 146
<211> LENGTH: 24
<212> TYPE: DNA
<213> ORGANISM: Artificial Sequence
<220> FEATURE:
<223> OTHER INFORMATION: Synthetic Primer

<400> SEQUENCE: 146
ugcugcuaau gcugcugcud tsdt                                              24

<210> SEQ ID NO 147
```

<210> SEQ ID NO 148
<211> LENGTH: 24
<212> TYPE: DNA
<213> ORGANISM: Artificial Sequence
<220> FEATURE:
<223> OTHER INFORMATION: Synthetic Primer

<400> SEQUENCE: 147
dtdtsacgac gauuacgacg acga                                          24

<210> SEQ ID NO 148
<211> LENGTH: 24
<212> TYPE: DNA
<213> ORGANISM: Artificial Sequence
<220> FEATURE:
<223> OTHER INFORMATION: Synthetic Primer

<400> SEQUENCE: 148
ugcugcugau acugcugcud tsdt                                          24

<210> SEQ ID NO 149
<211> LENGTH: 24
<212> TYPE: DNA
<213> ORGANISM: Artificial Sequence
<220> FEATURE:
<223> OTHER INFORMATION: Synthetic Primer

<400> SEQUENCE: 149
dtdtsacgac gacuaugacg acga                                          24

<210> SEQ ID NO 150
<211> LENGTH: 24
<212> TYPE: DNA
<213> ORGANISM: Artificial Sequence
<220> FEATURE:
<223> OTHER INFORMATION: Synthetic Primer

<400> SEQUENCE: 150
ugcugcuaaa gcugcugcud tsdt                                          24

<210> SEQ ID NO 151
<211> LENGTH: 24
<212> TYPE: DNA
<213> ORGANISM: Artificial Sequence
<220> FEATURE:
<223> OTHER INFORMATION: Synthetic Primer

<400> SEQUENCE: 151
dtdtsacgac gauuucgacg acga                                          24

<210> SEQ ID NO 152
<211> LENGTH: 24
<212> TYPE: DNA
<213> ORGANISM: Artificial Sequence
<220> FEATURE:
<223> OTHER INFORMATION: Synthetic Primer

<400> SEQUENCE: 152
ugcugcuaau acugcugcud tsdt                                          24

<210> SEQ ID NO 153
<211> LENGTH: 24
<212> TYPE: DNA
<213> ORGANISM: Artificial Sequence
<220> FEATURE:
<223> OTHER INFORMATION: Synthetic Primr

<400> SEQUENCE: 153
dtdtsacgac gauuaugacg acga          24

<210> SEQ ID NO 154
<211> LENGTH: 24
<212> TYPE: DNA
<213> ORGANISM: Artificial Sequence
<220> FEATURE:
<223> OTHER INFORMATION: Synthetic Primer

<400> SEQUENCE: 154
ugcugcugaa acugcugcud tsdt          24

<210> SEQ ID NO 155
<211> LENGTH: 24
<212> TYPE: DNA
<213> ORGANISM: Artificial Sequence
<220> FEATURE:
<223> OTHER INFORMATION: Synthetic Primer

<400> SEQUENCE: 155
dtdtsacgac gacuuugacg acga          24

<210> SEQ ID NO 156
<211> LENGTH: 24
<212> TYPE: DNA
<213> ORGANISM: Artificial Sequence
<220> FEATURE:
<223> OTHER INFORMATION: Synthetic Primer

<400> SEQUENCE: 156
ugcugcuaaa acugcugcud tsdt          24

<210> SEQ ID NO 157
<211> LENGTH: 24
<212> TYPE: DNA
<213> ORGANISM: Artificial Sequence
<220> FEATURE:
<223> OTHER INFORMATION: Synthetic Primer

<400> SEQUENCE: 157
dtdtsacgac gauuuugacg acga          24

<210> SEQ ID NO 158
<211> LENGTH: 24
<212> TYPE: DNA
<213> ORGANISM: Artificial Sequence
<220> FEATURE:
<223> OTHER INFORMATION: Synthetic Primer

<400> SEQUENCE: 158
gcugcugcug cugcugcugd tsdt          24

<210> SEQ ID NO 159
<211> LENGTH: 24
<212> TYPE: DNA
<213> ORGANISM: Artificial Sequence
<220> FEATURE:
<223> OTHER INFORMATION: Synthetic Primer

<400> SEQUENCE: 159
dtdtscgacg acgacgacga cgac          24

<210> SEQ ID NO 160
<211> LENGTH: 24
<212> TYPE: DNA

```
<213> ORGANISM: Artificial Sequence
<220> FEATURE:
<223> OTHER INFORMATION: Synthetic Primer

<400> SEQUENCE: 160
gcugcugcua cugcugcugd tsdt                                              24

<210> SEQ ID NO 161
<211> LENGTH: 24
<212> TYPE: DNA
<213> ORGANISM: Artificial Sequence
<220> FEATURE:
<223> OTHER INFORMATION: Synthetic Primer

<400> SEQUENCE: 161
dtsdtcgacg acgaugacga cgac                                              24

<210> SEQ ID NO 162
<211> LENGTH: 24
<212> TYPE: DNA
<213> ORGANISM: Artificial Sequence
<220> FEATURE:
<223> OTHER INFORMATION: Synthetic Primer

<400> SEQUENCE: 162
gcugcugcug augcugcugd tsdt                                              24

<210> SEQ ID NO 163
<211> LENGTH: 23
<212> TYPE: DNA
<213> ORGANISM: Artificial Sequence
<220> FEATURE:
<223> OTHER INFORMATION: Synthetic Primer

<400> SEQUENCE: 163
dtstcgacga cgacuacgac gac                                               23

<210> SEQ ID NO 164
<211> LENGTH: 24
<212> TYPE: DNA
<213> ORGANISM: Artificial Sequence
<220> FEATURE:
<223> OTHER INFORMATION: Synthetic Primer

<400> SEQUENCE: 164
ugcugcugcy gcugcugcud tsdt                                              24

<210> SEQ ID NO 165
<211> LENGTH: 24
<212> TYPE: DNA
<213> ORGANISM: Artificial Sequence
<220> FEATURE:
<223> OTHER INFORMATION: Synthetic Primer

<400> SEQUENCE: 165
dtdtsacgac gacgacgacg acga                                              24

<210> SEQ ID NO 166
<211> LENGTH: 24
<212> TYPE: DNA
<213> ORGANISM: Artificial Sequence
<220> FEATURE:
<223> OTHER INFORMATION: Synthetic Primer

<400> SEQUENCE: 166
ugcugcugcy gcugcugcud tsdt                                              24
```

<210> SEQ ID NO 167
<211> LENGTH: 24
<212> TYPE: DNA
<213> ORGANISM: Artificial Sequence
<220> FEATURE:
<223> OTHER INFORMATION: Synthetic Primer

<400> SEQUENCE: 167
dtdtsacgac gacgacgacg acga                                            24

<210> SEQ ID NO 168
<211> LENGTH: 24
<212> TYPE: DNA
<213> ORGANISM: Artificial Sequence
<220> FEATURE:
<223> OTHER INFORMATION: Synthetic Primer

<400> SEQUENCE: 168
gcugcugcyg cugcugcugd tsdt                                            24

<210> SEQ ID NO 169
<211> LENGTH: 24
<212> TYPE: DNA
<213> ORGANISM: Artificial Sequence
<220> FEATURE:
<223> OTHER INFORMATION: Synthetic Primer

<400> SEQUENCE: 169
dtdtscgacg acgacgacga cgac                                            24

<210> SEQ ID NO 170
<211> LENGTH: 24
<212> TYPE: DNA
<213> ORGANISM: Artificial Sequence
<220> FEATURE:
<223> OTHER INFORMATION: Synthetic Primer

<400> SEQUENCE: 170
gcugcugcuy cugcugcugd tsdt                                            24

<210> SEQ ID NO 171
<211> LENGTH: 24
<212> TYPE: DNA
<213> ORGANISM: Artificial Sequence
<220> FEATURE:
<223> OTHER INFORMATION: Synthetic Primer

<400> SEQUENCE: 171
dtdtscgacg acgaugacga cgac                                            24

<210> SEQ ID NO 172
<211> LENGTH: 24
<212> TYPE: DNA
<213> ORGANISM: Artificial Sequence
<220> FEATURE:
<223> OTHER INFORMATION: Synthetic Primer

<400> SEQUENCE: 172
gcugcugcug yugcugcugd tsdt                                            24

<210> SEQ ID NO 173
<211> LENGTH: 24
<212> TYPE: DNA
<213> ORGANISM: Artificial Sequence
<220> FEATURE:

<223> OTHER INFORMATION: Synthetic Primer

<400> SEQUENCE: 173
dtdtscgacg acgacuacga cgac							24

<210> SEQ ID NO 174
<211> LENGTH: 24
<212> TYPE: DNA
<213> ORGANISM: Artificial Sequence
<220> FEATURE:
<223> OTHER INFORMATION: Synthetic Primer

<400> SEQUENCE: 174
gcugcugcyg cugcugcugd tsdt							24

<210> SEQ ID NO 175
<211> LENGTH: 24
<212> TYPE: DNA
<213> ORGANISM: Artificial Sequence
<220> FEATURE:
<223> OTHER INFORMATION: Synthetic Primer

<400> SEQUENCE: 175
dtdtscgacg acgacgacga cgac							24

<210> SEQ ID NO 176
<211> LENGTH: 24
<212> TYPE: DNA
<213> ORGANISM: Artificial Sequence
<220> FEATURE:
<223> OTHER INFORMATION: Synthetic Primer

<400> SEQUENCE: 176
gcugcugcuy cugcugcugd tsdt							24

<210> SEQ ID NO 177
<211> LENGTH: 24
<212> TYPE: DNA
<213> ORGANISM: Artificial Sequence
<220> FEATURE:
<223> OTHER INFORMATION: Synthetic Primer

<400> SEQUENCE: 177
dtdtscgacg acgaugacga cgac							24

<210> SEQ ID NO 178
<211> LENGTH: 24
<212> TYPE: DNA
<213> ORGANISM: Artificial Sequence
<220> FEATURE:
<223> OTHER INFORMATION: Synthetic Primer

<400> SEQUENCE: 178
gcugcugcug yugcugcugd tsdt							24

<210> SEQ ID NO 179
<211> LENGTH: 24
<212> TYPE: DNA
<213> ORGANISM: Artificial Sequence
<220> FEATURE:
<223> OTHER INFORMATION: Synthetic Primer

<400> SEQUENCE: 179
dtdtscgacg acgacuacga cgac							24

-continued

<210> SEQ ID NO 180
<211> LENGTH: 21
<212> TYPE: DNA
<213> ORGANISM: Artificial Sequence
<220> FEATURE:
<223> OTHER INFORMATION: Synthetic Primer

<400> SEQUENCE: 180
gcugcugcug cugcugcugt t                                              21

<210> SEQ ID NO 181
<211> LENGTH: 21
<212> TYPE: DNA
<213> ORGANISM: Artificial Sequence
<220> FEATURE:
<223> OTHER INFORMATION: Synthetic Primer

<400> SEQUENCE: 181
gcuacugcug cugcugcugt t                                              21

<210> SEQ ID NO 182
<211> LENGTH: 21
<212> TYPE: DNA
<213> ORGANISM: Artificial Sequence
<220> FEATURE:
<223> OTHER INFORMATION: Synthetic Primer

<400> SEQUENCE: 182
gcugaugcug cugcugcugt t                                              21

<210> SEQ ID NO 183
<211> LENGTH: 21
<212> TYPE: DNA
<213> ORGANISM: Artificial Sequence
<220> FEATURE:
<223> OTHER INFORMATION: Synthetic Primer

<400> SEQUENCE: 183
gcugcagcug cugcugcugt t                                              21

<210> SEQ ID NO 184
<211> LENGTH: 21
<212> TYPE: DNA
<213> ORGANISM: Artificial Sequence
<220> FEATURE:
<223> OTHER INFORMATION: Synthetic Primer

<400> SEQUENCE: 184
gcugcuacug cugcugcugt t                                              21

<210> SEQ ID NO 185
<211> LENGTH: 21
<212> TYPE: DNA
<213> ORGANISM: Artificial Sequence
<220> FEATURE:
<223> OTHER INFORMATION: Synthetic Primer

<400> SEQUENCE: 185
gcugcugcug cagcugcugt t                                              21

<210> SEQ ID NO 186
<211> LENGTH: 21
<212> TYPE: DNA
<213> ORGANISM: Artificial Sequence
<220> FEATURE:
<223> OTHER INFORMATION: Synthetic Primer

```
<400> SEQUENCE: 186
gcugcugcug cuacugcugt t                                              21

<210> SEQ ID NO 187
<211> LENGTH: 21
<212> TYPE: DNA
<213> ORGANISM: Artificial Sequence
<220> FEATURE:
<223> OTHER INFORMATION: Synthetic Primer

<400> SEQUENCE: 187
gcugcugcug cugcuacugt t                                              21

<210> SEQ ID NO 188
<211> LENGTH: 21
<212> TYPE: DNA
<213> ORGANISM: Artificial Sequence
<220> FEATURE:
<223> OTHER INFORMATION: Synthetic Primer

<400> SEQUENCE: 188
gcagcuguug cuacuguugt t                                              21

<210> SEQ ID NO 189
<211> LENGTH: 21
<212> TYPE: DNA
<213> ORGANISM: Artificial Sequence
<220> FEATURE:
<223> OTHER INFORMATION: Synthetic Primer

<400> SEQUENCE: 189
gcuauaccag cgucgucaut t                                              21

<210> SEQ ID NO 190
<211> LENGTH: 21
<212> TYPE: DNA
<213> ORGANISM: Artificial Sequence
<220> FEATURE:
<223> OTHER INFORMATION: Synthetic Primer

<400> SEQUENCE: 190
gcuacugcua cugcuacugt t                                              21

<210> SEQ ID NO 191
<211> LENGTH: 21
<212> TYPE: DNA
<213> ORGANISM: Artificial Sequence
<220> FEATURE:
<223> OTHER INFORMATION: Synthetic Primer

<400> SEQUENCE: 191
gcuacugcug cugcugcugt t                                              21

<210> SEQ ID NO 192
<211> LENGTH: 21
<212> TYPE: DNA
<213> ORGANISM: Artificial Sequence
<220> FEATURE:
<223> OTHER INFORMATION: Synthetic Primer

<400> SEQUENCE: 192
cugcugcugc ugcugcugct t                                              21

<210> SEQ ID NO 193
<211> LENGTH: 21
```

```
<212> TYPE: DNA
<213> ORGANISM: Artificial Sequence
<220> FEATURE:
<223> OTHER INFORMATION: Synthetic Primer

<400> SEQUENCE: 193
ugcugcugcu gcugcugcut t                                      21

<210> SEQ ID NO 194
<211> LENGTH: 21
<212> TYPE: DNA
<213> ORGANISM: Artificial Sequence
<220> FEATURE:
<223> OTHER INFORMATION: Synthetic Primer

<400> SEQUENCE: 194
cugcugcuga ugcugcugct t                                      21

<210> SEQ ID NO 195
<211> LENGTH: 21
<212> TYPE: DNA
<213> ORGANISM: Artificial Sequence
<220> FEATURE:
<223> OTHER INFORMATION: Synthetic Primer

<400> SEQUENCE: 195
ttcgaugacg acgacgacga c                                      21

<210> SEQ ID NO 196
<211> LENGTH: 21
<212> TYPE: DNA
<213> ORGANISM: Artificial Sequence
<220> FEATURE:
<223> OTHER INFORMATION: Synthetic Primer

<400> SEQUENCE: 196
ttcgacgucg acgacgacga c                                      21

<210> SEQ ID NO 197
<211> LENGTH: 21
<212> TYPE: DNA
<213> ORGANISM: Artificial Sequence
<220> FEATURE:
<223> OTHER INFORMATION: Synthetic Primer

<400> SEQUENCE: 197
ttcgacgaug acgacgacga c                                      21

<210> SEQ ID NO 198
<211> LENGTH: 21
<212> TYPE: DNA
<213> ORGANISM: Artificial Sequence
<220> FEATURE:
<223> OTHER INFORMATION: Synthetic Primer

<400> SEQUENCE: 198
ttcgacgacg acgucgacga c                                      21

<210> SEQ ID NO 199
<211> LENGTH: 21
<212> TYPE: DNA
<213> ORGANISM: Artificial Sequence
<220> FEATURE:
<223> OTHER INFORMATION: Synthetic Primer

<400> SEQUENCE: 199
```

```
ttcgacgacg acgaugacga c                                              21

<210> SEQ ID NO 200
<211> LENGTH: 21
<212> TYPE: DNA
<213> ORGANISM: Artificial Sequence
<220> FEATURE:
<223> OTHER INFORMATION: Synthetic Primer

<400> SEQUENCE: 200
ttcgacgacg acgacgauga c                                              21

<210> SEQ ID NO 201
<211> LENGTH: 21
<212> TYPE: DNA
<213> ORGANISM: Artificial Sequence
<220> FEATURE:
<223> OTHER INFORMATION: Synthetic Primer

<400> SEQUENCE: 201
ttcgaugacg augacgauga c                                              21

<210> SEQ ID NO 202
<211> LENGTH: 21
<212> TYPE: DNA
<213> ORGANISM: Artificial Sequence
<220> FEATURE:
<223> OTHER INFORMATION: Synthetic Primer

<400> SEQUENCE: 202
ttcgucgaca acgaugacaa c                                              21
```